United States Patent
Hogan et al.

(10) Patent No.: US 11,851,705 B2
(45) Date of Patent: *Dec. 26, 2023

(54) MICROARRAY BASED MULTIPLEX PATHOGEN ANALYSIS FOR PLANTS, AGRICULTURE, FOOD, AND WATER

(71) Applicants: Michael Edward Hogan, Stony Brook, NY (US); Melissa Rose May, Tucson, AZ (US); Frederick Henry Eggers, Sahuarita, AZ (US)

(72) Inventors: Michael Edward Hogan, Stony Brook, NY (US); Melissa Rose May, Tucson, AZ (US); Frederick Henry Eggers, Sahuarita, AZ (US)

(73) Assignee: PathogenDX Inc, Scottsdale, AZ (US)

( * ) Notice: Subject to any disclaimer, the term of this patent is extended or adjusted under 35 U.S.C. 154(b) by 63 days.

This patent is subject to a terminal disclaimer.

(21) Appl. No.: 16/819,564

(22) Filed: Mar. 16, 2020

(65) Prior Publication Data
US 2020/0283845 A1 Sep. 10, 2020

Related U.S. Application Data

(63) Continuation of application No. 15/388,561, filed on Dec. 22, 2016, now abandoned.

(60) Provisional application No. 62/271,371, filed on Dec. 28, 2015.

(51) Int. Cl.
*C12Q 1/6874* (2018.01)

(52) U.S. Cl.
CPC .................. *C12Q 1/6874* (2013.01)

(58) Field of Classification Search
CPC ...................................................... C12Q 1/689
See application file for complete search history.

(56) References Cited

U.S. PATENT DOCUMENTS

| | | | |
|---|---|---|---|
| 10,272,409 B2 | 4/2019 | Hogan et al. | |
| 2009/0035767 A1* | 2/2009 | Suzuki | C12Q 1/689 435/6.15 |
| 2011/0245094 A1* | 10/2011 | Washburn | C07K 14/24 506/9 |
| 2012/0122719 A1* | 5/2012 | Hogan | C12Q 1/686 435/5 |
| 2017/0327599 A1 | 11/2017 | Hogan | |

FOREIGN PATENT DOCUMENTS

| | | |
|---|---|---|
| WO | 1989011548 A1 | 11/1989 |
| WO | 199905321 A1 | 2/1999 |
| WO | 2003043402 A2 | 5/2003 |

OTHER PUBLICATIONS

Beyer et al. Easy Daylight Fabricated Hydrogel Array for Colorimetric DNA Analysis, Macromol. Biosci., 2014, 14(6):889-898.
Conzone, Samuel D. and Patano, Carlo G., Glass Slides to DNA Microarrays, Materialstoday, Mar. 1, 2004, 7(3):20-26.
Dufva, Martin, Fabrication of High Quality Microarrays, Biomolecular Engineering, 2005, 22:173-184.
Mumford et al. Advances in Molecular Phytodiagnostics—New Solutions for Old Problems, European Journal of Plant Pathology, 2006, 116:1-19.
Nikitin et al. Matrix Approach to the Simultaneous Detection of Multiple Potato Pathogens by Real-Time PCR, Journal of Applied Microbiology, Feb. 11, 2018, 124(3):797-809.
Tang, Jing and Xiao, Pengfeng, Polymerizing Immobilization of Acrylamide-Modified Nucleic Acids and Its Application, Biosensors and Bioelectronics, 2009, 24:1817-1824.
Wang et al. Development of Multiplex Reverse Transcription-Ligase Detection Reaction-Polymerase Chain Reaction (MRLP) Mediated Universal DNA Microarray for Diagnostic Platform, Biosensors and Bioelectronics, 2011, 26:3719-3724.
Wu et al. An Activated GOPS-poly-L-Lysine-Coated Glass Surface for the Immobilization of 60mer Oligonucleotides, Eng. Life Sci., 2005, 5(5):466-470.

* cited by examiner

*Primary Examiner* — Joseph G. Dauner
(74) *Attorney, Agent, or Firm* — Benjamin Aaron Adler

(57) ABSTRACT

Provided is a method for a two-step multiplex DNA amplification reaction which allows bacterial or fungal DNA analysis without first extracting DNA from the sample, nor without need to enrich microbes by laboratory culture prior to analysis. Without additional DNA purification or analysis, the PCR amplified DNA is administered directly to a microarray designed to interrogate a large panel of meaningful bacteria or fungi as a single multiplex test. Microarray analysis is then performed at ambient temperature, thus enabling substantial simplification of the testing process. It is contemplated that analysis may be conducted on unprocessed and processed leaf wash and similar surface sampling of plant material, *cannabis*, vegetables, fruit, nuts, spices, grains, other agriculture samples, food samples, or water samples, so as to detect bacterial, yeast, mold or viral, plant or human pathogen contamination.

12 Claims, 43 Drawing Sheets

Specification includes a Sequence Listing.

16S rDNA Locus (All Bacteria)

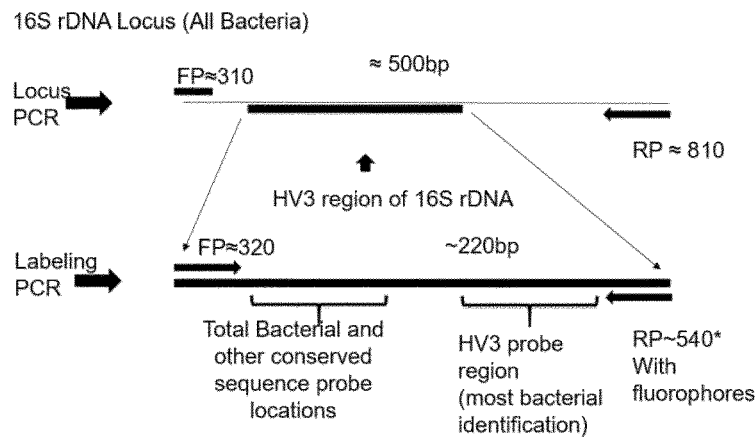

PCR Primers for amplification of the 16S rDNA HV3 Locus

| Primer name | Seq 5'-3' | SEQ ID NO |
|---|---|---|
| 1-PDX-16S-FP | TTTCACAYTGGRACTGAGACACG | 1 |
| 1-PDX-16S-RP | TTTGACTACCAGGGTATCTCTAATCCTGT | 2 |

PCR Primers for the labeling amplification rxn. of the 16S rDNA HV3 Locus

| Primer name | Seq 5'-3' | SEQ ID NO |
|---|---|---|
| 2-PDX-16S-FP | TTTACTGAGACACGGYCCARACTC | 3 |
| 2-PDX-16S-RP | TTTGTATTACCGCGGCTGCTGGCA | 4 |

Stx1 Locus (Pathogenic E.coli)

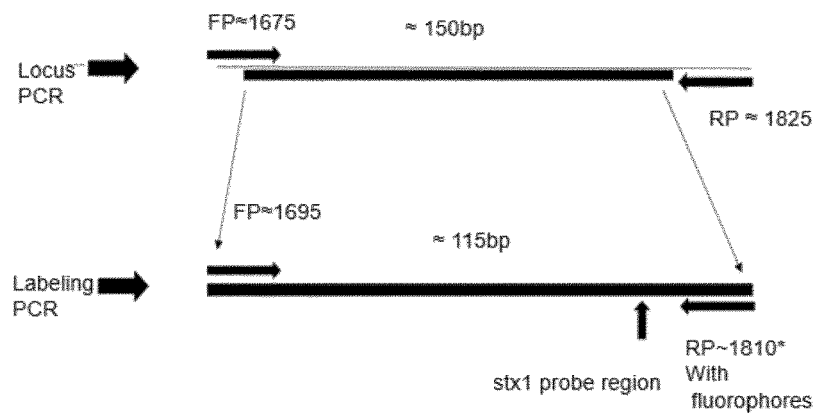

PCR Primers for amplification of the 16S rDNA HV3 Locus

| Primer name | Seq 5'-3' | SEQ ID NO |
|---|---|---|
| 1-PDX-STX1-FP | TTTATAATCTACGGCTTATTGTTGAACG | 5 |
| 1-PDX-STX-RP | TTTGGTATAGCTACTGTCACCAGACAATG | 6 |

PCR Primers for the labeling amplification rxn. of the 16S rDNA HV3 Locus

| Primer name | Seq 5'-3' | SEQ ID NO |
|---|---|---|
| 2-PDX-STX-FP | TTTATGTGACAGGATTTGTTAACAGGAC | 7 |
| 2-PDX-STX-RP | TTTCTGTCACCAGACAATGTAACCGCTG | 8 |

Figure 1

Stx2 Locus (Pathogenic E.coli)

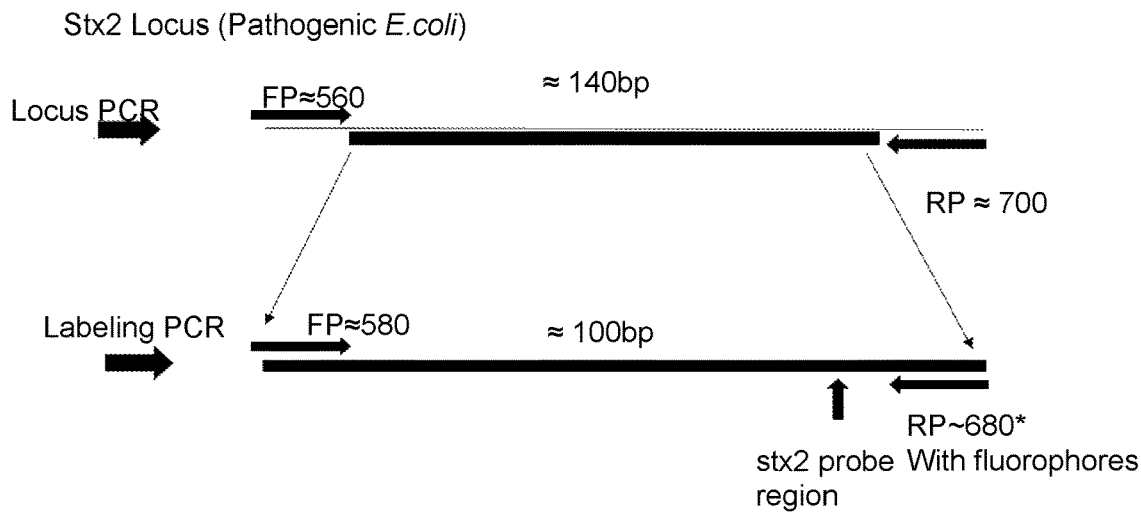

PCR Primers for amplification of the Stx2 Locus
| Primer name | seq 5'-3' | SEQ ID NO |
|---|---|---|
| 1-PDX-STX2-FP | TTTGATGCATCCAGAGCAGTTCTGCG | 9 |
| 1-PDX-STX2-RP | TTTGTGAGGTCCACGTCTCCCGGGCGTC | 10 |

PCR Primers for the labeling amplification rxn. Of the Stx2 Locus
| Primer name | seq 5'-3' | SEQ ID NO |
|---|---|---|
| 2-PDX-STX2-FP | TTTTGTCACTGTCACAGCAGAAG | 11 |
| 2-PDX-STX2-RP | TTTGCGTCATCGTATACACAGGAGC | 12 | invA Locus (All Salmonella)

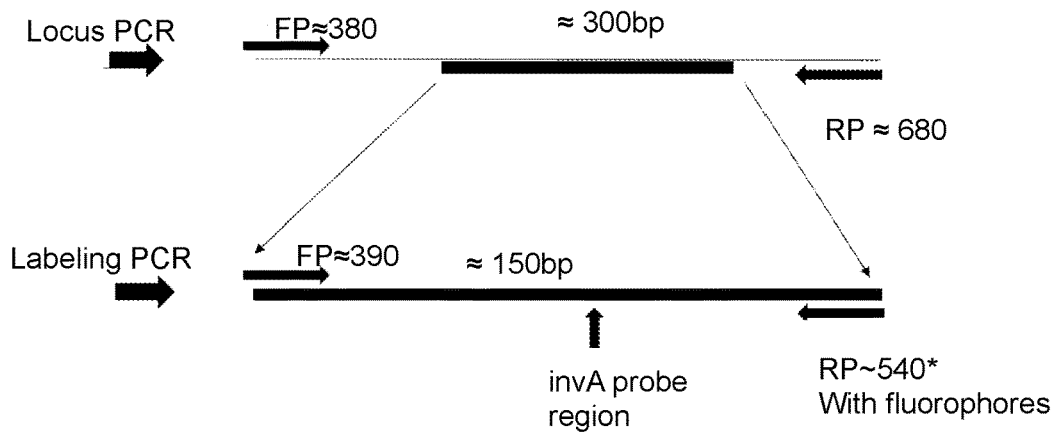

PCR Primers for amplification of the InvA Locus
| Primer name | seq 5'-3' | SEQ ID NO |
|---|---|---|
| 1-PDX-InvA-FP | TTTATTATCGCCACGTTCGGGCAATTCG | 13 |
| 1-PDX-InvA-RP | TTTCTTCATCGCACCGTCAAAGGAACCG | 14 |

PCR Primers for the labeling amplification rxn. Of the Stx2 Locus
| Primer name | seq 5'-3' | SEQ ID NO |
|---|---|---|
| 2-PDX-InvA-FP | TTTTATCGTTATTACCAAAGGTTCAG | 15 |
| 2-PDX-InvA-RP | TTTCCTTTCCAGTACGCTTCGCCGTTCG | 16 |

FIG. 2

PCR Primers for amplification of the tuf Locus

| Primer name | seq 5'-3' | SEQ ID NO |
|---|---|---|
| 1-PDX-Etuf-FP | *TTTCAGAGTGGGAAGCGAAAATCCTG | 17 |
| 1-PDX-Etuf-RP | TTTACGCCAGTACAGGTAGACTTCTG | 18 |

PCR Primers for the labeling amplification rxn. of the tuf Locus

| Primer name | seq 5'-3' | SEQ ID NO |
|---|---|---|
| 2-PDX-Etuf-FP | TTTGTTGTTACCGGTCGTGTAGAAC | 19 |
| 2-PDX-Etuf-RP | TTTCTTCTGAGTCTCTTTGATACCAACG | 20 |

PCR Primers for amplification of the ITS2 Locus
| Primer name | seq 5'-3' | SEQ ID NO |
|---|---|---|
| 1-PDX-ITS2 -FP | TTTACTTTYAACAAYGGATCTCTTGG | 21 |
| 1-PDX-ITS2 -RP | TTTCTTTTCCTCCGCTTATTGATATG | 22 |

PCR Primers for the labeling amplification rxn. of the ITS2 Locus
| Primer name | seq 5'-3' | SEQ ID NO |
|---|---|---|
| 2-PDX-ITS2 -FP | TTTGCATCGATGAAGARCGYAGC | 23 |
| 2-PDX-ITS2 -RP | TTTCCTCCGCTTATTGATATGC | 24 |

| Bacterial organism/group | Oligonucleotide probe sequence for the 16S locus | SEQ ID NO |
|---|---|---|
| Salmonella enterica/Enterobactor | TTTTTTTGTTGTGGTTAATAACCGATTTTT | 37 |
| | TTTTTTTAACCGCAGCAATTGACTCTTTTT | 38 |
| | TTTTTTCTGTTAATAACCGCAGCTTTTTT | 39 |
| E.coli/Shigella | TTTTCTAATACCTTTGCTCATTGACTCTTT | 40 |
| | TTTTTTAAGGGAGTAAAGTTAATATTTTTT | 41 |
| | TTTTCTCCTTTGCTCATTGACGTTATTTTT | 42 |
| Pseudomonas spp | TTTTTTGTTACCRACAGAATAAGCATTTTT | 43 |
| | TTTTTTAAGCACTTTAAGTTGGGATTTTTT | 44 |
| Salmonella bongori | TTTTTTTAATAACCTTGTTGATTGTTTTTT | 45 |
| Pseudomonas aeruginosa | TTTTTGCAGTAAGTTAATACCTTGTCTTTT | 46 |
| Pseudomonas cannabina | TTTTTTTACGTATCTGTTTTGACTCTTTTT | 47 |
| Xanthomonas spp. | TTTTTTGTTAATACCCGATTGTTCTTTTTT | 48 |
| Listeria spp. | TTTTCTAAGTACTGTTGTTAGAGAATTTTT | 49 |
| Campylobactor spp. | TTTTTTATGACATTTTCGGAGCTCTTTTT | 50 |
| Aeromonas salmonicida/hydrophiia | TTTTTGCCTAATACGRTCAACTGCTTTTT | 51 |
| Aeromonas spp. | TTATTTTCTGTGACGTTACTCGCTTTTATT | 52 |
| Vibrio spp. | TTTTTTGAAGGTGGTTAGCTAATTTTTTT | 53 |
| Staphylococcus aureus | TTTTTTCATATGTGTAAGTAACTATTTTTT | 54 |
| Bacillus spp. Group 1 | TTTTTCAGTTGAATAAGCTGGCACTCTTTT | 55 |
| Bacillus spp. Group 2 | TTTTTTCAAGTACCGTTCGAATAGTTTTTT | 56 |
| Alkanindinges spp. | TTTTTAGGCTACTGRTACTAATATCTTTTT | 57 |
| Citrobacter spp. Group 1 | TTTTTTCCTTAGCCATTGACGTTATTTTTT | 58 |
| Clostridium spp. | TTTTCTGGAMGATAATGACGGTACAGTTTT | 59 |
| Yersinia pestis | TTTTTTTGAGTTTAATACGCTCAACTTTTT | 60 |
| Panteoa agglomerans | TTTTTTAACCCTGTCGATTGACGCCTTTTT | 61 |
| Panteoa stewartii | TTTTTTAACCTCATCAATTGACGCCTTTTT | 62 |
| Hafni spp. | TTTTTTCTAACCGCAGTGATTGATCTTTTT | 63 |
| Klebsiella pneumoniae | TTTTTTCTAACCTTGGCGATTGATCTTTTT | 64 |
| Serratia spp. | TTTATTCTGTGAACTTAATACGTTCATTTTATT | 65 |
| Klebsiella oxytoca | TTTTTTCTAACCTTATTCATTGATCTTTTT | 66 |
| Chromobacterium spp. | TTTTATTTCCCGCTGGTTAATACCCITTATITT | 67 |
| Bacillus pumilus | TTTATTTAAGTGCRAGAGTAACTGCTATTTTATT | 68 |
| Streptomyces spp. | TTTTATTTTAAGAAGCGAGAGTGACTITTATTT | 69 |
| Legionella spp. | TTTATTCTGATAGGTTAAGAGCGATCTTTATTT | 70 |
| Total Aerobic Bacteria (Hi Sensitivity) | TTTTTTTTCCCTACGGGAGGCATTTTTTT | 71 |
| Total Aerobic Bacteria (Md sensitivity) | TTTTTTTTCCCTACGGGAGGCATTTTTTT | 72 |
| Total Aerobic Bacteria (Lo sensitivity) | TTTATTTTCCCTACGGGAGGCTTTTATTTT | 73 |
| Bile-Tolerant Gram-neg (Hi sensitivity) | TTTTTCTATGCAGTCATGCTGTGTGTRTGTCTTTT | 74 |
| Bile-Tolerant Gram-neg (Md sensitivity) | TTTTTCTATGCAGCCARGCTGTGTGTRTTTTTTT | 75 |
| Bile-Tolerant Gram-neg (Lo sensitivity) | TTTTTCTATGCAGTCATGCTGCGTGTRTTTTTTT | 76 |
| Enterobacteriaceae (HI sensitivity) | TTTTTTCTATTGACGTTACCCGCTTTTTTT | 77 |
| Enterobacteriaceae (Md sensitivity) | TTTTTTCTATTGACGTTACCCGTTTTTTTT | 78 |
| Enterobacteriaceae (Lo sensitivity) | TTTATTCTATTGACGTTACCCATTTATTTT | 79 |

Figure 6A

| Fungal organism/ group | Oligonucleotide probe sequence for the ITS2 locus | SEQ ID NO |
|---|---|---|
| Aspergillus fumigatus | TTTTTTTGCCAGCCGACACCCATTCTTTTT | 80 |
| | TTTCTTTTCGACACCCAACTTTATTTCCTTATTT | 81 |
| Aspergillus flavus | TTTTTTCGCAAATCAATCTTTTCCAGTCTTTTT | 82 |
| | TTTTTTTCTTGCCGAACGCAAATCTTTTTTTTTTT | 83 |
| Aspergillus niger | TTTTTTTTCGACGTTTTCCAACCATTTCTTTTTT | 84 |
| | TTTTTTTCGCCGACGTTTTCCAATTTTTTT | 85 |
| Aspergillus terreus | TTTTTCGACGCATTTATTTGCAACCCTTTT | 86 |
| Aspergillu nidulans | TTTTTTGGCGTCTCCAACCTTACCCTTTTT | 87 |
| Botrytis spp. | TTTTTTTCATCTCTCGTTACAGGTTCTCGGTTCTTTTTTT | 88 |
| Penicillium spp. | TTTTTTCAACCCAAATTTTATCCAGGCCTTTTT | 89 |
| Penicillium paxilli | TTTTTTCCCCTCAATCTTTAACCAGGCCTTTTT | 90 |
| Penivillium oxalicum | TTTTTTACACCATCAATCTTTAACCAGGCCTTTTT | 91 |
| Fusarium solani | TTTTTTTTAACACCTCGCRACTGGAGATTTTTTT | 92 |
| Mucor spp. | TTTTCTCCAWTGAGYACGCCTGTTTCTTTT | 93 |
| Histoplasma capsulatum | TTTATTTTTGTCGAGTTCCGGTGCCCTTTTATTT | 94 |
| Monocillium spp. | TTTCTTTTGAGCGACGACGGGCCCAATTTTCTTTT | 95 |
| Trichoderma spp. | TTTTTCCTCCTGCGCAGTAGTTTGCACATCTTTT | 96 |
| Chaetomium Spp. | TTTCTTTTGGTTCCGGCCGTTAAACCATTTTTTT | 97 |
| Stachybotrys spp. | TTTCTTCTGCATCGGAGCTCAGCGCGTTTATTT | 98 |
| Alternaria spp. | TTTTTTCAAAGGTCTAGCATCCTTAAGTTTTTT | 99 |
| Phama/Epicoccum spp. | TTTTTTTGCAGTACATCTCGCGCTTTGATTTTTT | 100 |
| Erysiphe spp. | TTTCTTTTTACGATTCTCGCGACAGAGTTTTTT | 101 |
| Podosphaera spp. | TTTTTTTTAGTCAYGTATCTCGCGACAGTTTTTT | 102 |
| Podosphaera macularis | TTTTTTGACCTGCCAAAACCCACATACCATTTTT | 103 |
| Oidiodendron spp. | TTTTTTTGCGTAGTACATCTCTCGCTCATTTTTT | 104 |
| Rhodotorula spp. | TTTTTCTCGTTCGTAATGCATTAGCACTTTTT | 105 |
| Cladosporium spp. | TTTTTTTGTGGAAACTATTCGCTAAAGTTTTTT | 106 |
| Fusarium oxysporum | TTTTTTTCTCGTTACTGGTAATCGTCGTTTTTTT | 107 |
| Candida spp. grp1 | TTTTTTTGTTTGGTGTTGAGCRATACGTATTTTT | 108 |
| Candida spp. grp2 | TTTTACTGTTTGGTAATGAGTGATACTCTCATTTT | 109 |
| Candida albicans | TTTTTTTTGAAAGACGGTAGTGGTAAGTTTTTT | 110 |
| Isaria spp. | TTTATTTTTCCGCGGCGACCTCTGCTCTTTATTT | 111 |
| Myrothecium spp. | TTTATTTTCGGTGGCCATGCCGTTAAATTTATTT | 112 |
| Pythium oligandrum | TTTTATTTAAAGGAGACAACACCAATTTTTATTT | 113 |
| Total yeast and Mold (Hi sensitivity) | TTTTTTTTGAATCATCGARTCTTTGAACGCATTTTTTT | 114 |
| Total yeast and Mold (Md sensitivity) | TTTTTTTTGAATCATCGARTCTTTGAACGTTTTTTT | 115 |
| Total yeast and Mold (Lo sensitivity) | TTTTTTTTGAATCATCGARTCTCCTTTTTTTT | 116 |

Figure 6B

| Target/group | | SEQ ID NO |
|---|---|---|
| Stx1 | TTTTTTCTTTCCAGGTACAACAGCTTTTTT | 117 |
| Stx2 | TTTTTTGCACTGTCTGAAACTGCCTTTTTT | 118 |
| invA | TTTTTTATTGATGCCGATTTGAAGGCCTTTTTT | 119 |
| tuf | TTTTTTCCATCAAAGTTGGTGAAGAATCTTTTTT | 120 |
| Cannabis spp. | TTTTTTAATCTGCGCCAAGGAACAATATTTTTTT | 121 |

Figure 7

Sample Processing Overview

- Wash the plant sample or tape pull in 1x PBS
- Remove plant material/tape
- Centrifuge to pellet cells & discard supernatant
- Resuspend in PDx sample Prep Buffer pre-mixed with Sample Digestion Buffer
- Heat at 55°C for 45 minutes
- Vortex to dislodge the pellet
- Heat at 95°C for 15 minutes
- Vortex and centrifuge briefly before use in PCR Representative Image of a DNA Microarray

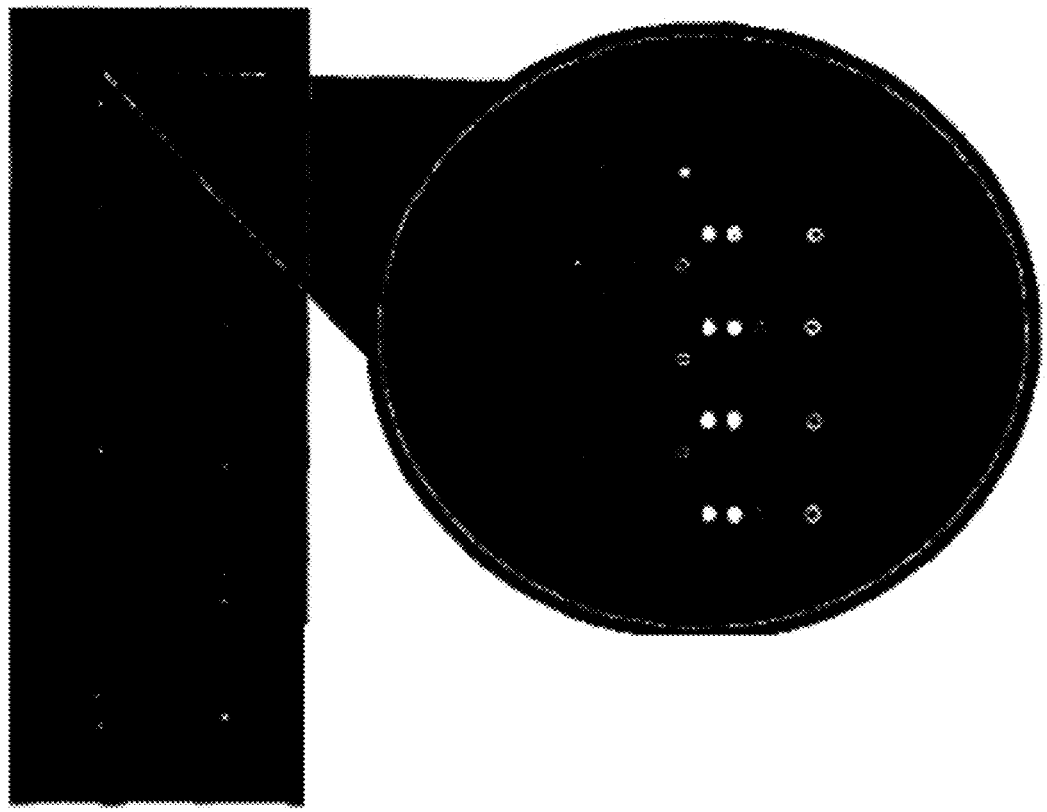

- Representative Image of a PathogenDx slide after hybridization where each microarray queries the full pathogen detection panel in quadruplicate.
- During the DNA binding step (hybridization), the dye labeled PCR product is placed onto the microarray for 30 minutes at room temperature.
- Green fluorescent spots indicate positive detection of pathogen.

Figure 9

Microaary Analysis of Raw Cannabis Wash

| Identification Panel | | | | | |
|---|---|---|---|---|---|
| Sample | 1 | 2 | 3 | 4 | 5 |
| Cannabis DNA control | 29348 | 18804 | 17983 | 14549 | 14960 |
| Aeromonas | 137 | 145 | 245 | 138 | 382 |
| E.coli | 132 | 145 | 144 | 124 | 389 |
| E.coli specific gene | 563 | 471 | 461 | 1205 | 6408 |
| Enterobacteriacea | 136 | 14805 | 14246 | 149 | 24071 |
| Listeria | 142 | 163 | 142 | 133 | 311 |
| Pseudomonas | 112 | 1895 | 2033 | 102 | 1579 |
| Pseudomonas aeruginosa | 153 | 1140 | 992 | 121 | 2290 |
| Salmonella/Enterobacter | 125 | 285 | 616 | 126 | 742 |
| Salmonella specific gene | 199 | 201 | 207 | 164 | 320 |
| Xanthomonas | 119 | 151 | 141 | 106 | 213 |
| Aspergillus fumigatus | 33335 | 9241 | 3861 | 3676 | 6224 |
| Aspergillus flavus | 1228 | 112 | 1198 | 136 | 2955 |
| Aspergillus niger | 139 | 119 | 161 | 142 | 691 |
| Botrytis | 159 | 142 | 182 | 120 | 181 |
| Penicillium | 154 | 182 | 153 | 100 | 2504 |
| Fusarium solani | 132 | 115 | 127 | 111 | 135 |
| Mucor | 122 | 139 | 129 | 130 | 129 |
| Candida | 286 | 173 | 415 | 108 | 129 |

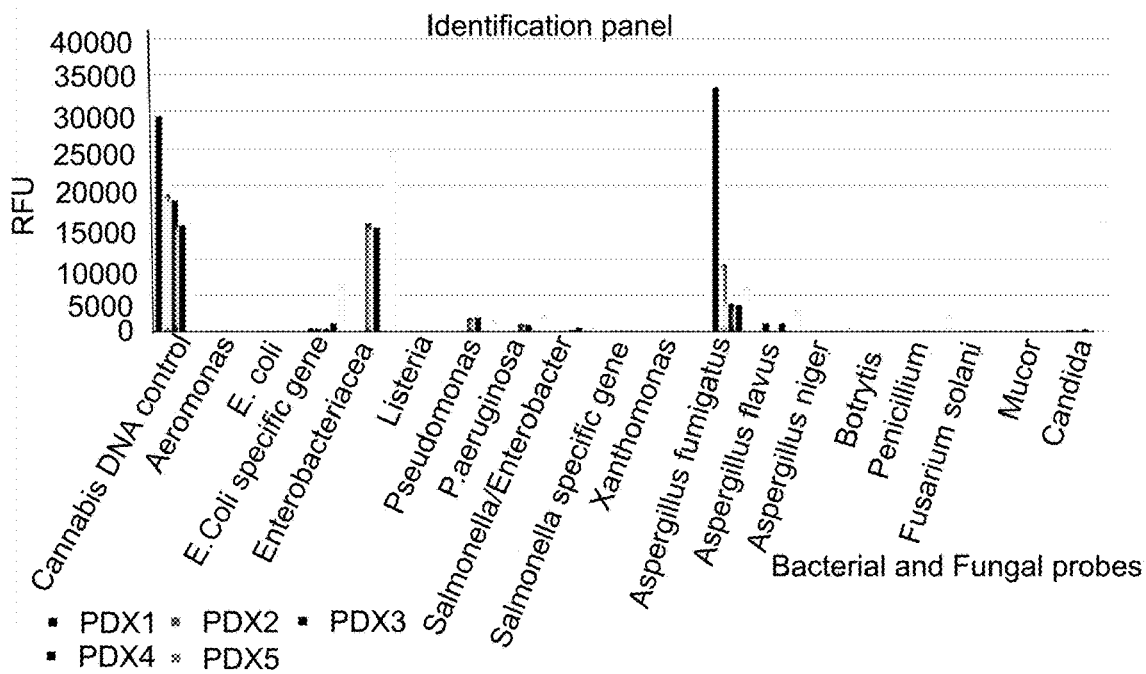

Figure 11

Raw Vitroid vs Raw Cannabis Wash Data

| Cannabis DNA control | Cannabis Wash | Candida albicans Vitriod |
|---|---|---|
| Cannabis DNA control 1 | 1810 | 113 |
| Cannabis DNA control 2 | 9203 | 124 |
| Low Pan Fungal Control | 9526 | 14051 |
| Medium Pan Fungal Control | 21814 | 37310 |
| High Pan Fungal Control | 41190 | 65000 |
| Negative control | 45 | 131 |
| Aspergillus fumigatus | 292 | 152 |
| Aspergillus flavus | 39 | 135 |
| Aspergillus niger | 37 | 130 |
| Botrytis | 29 | 228 |
| Penicillium | 34 | 118 |
| Fusarium solani | 42 | 126 |
| Mucor | 39 | 121 |
| Candida Group 1 | 2695 | 6885 |
| Candida albicans | 37 | 10386 |
| Isaria Biofoliar | 29 | 126 |
| Myrothesium Biofoliar | 135 | 121 |
| Pythium Biofoliar | 153 | 189 |

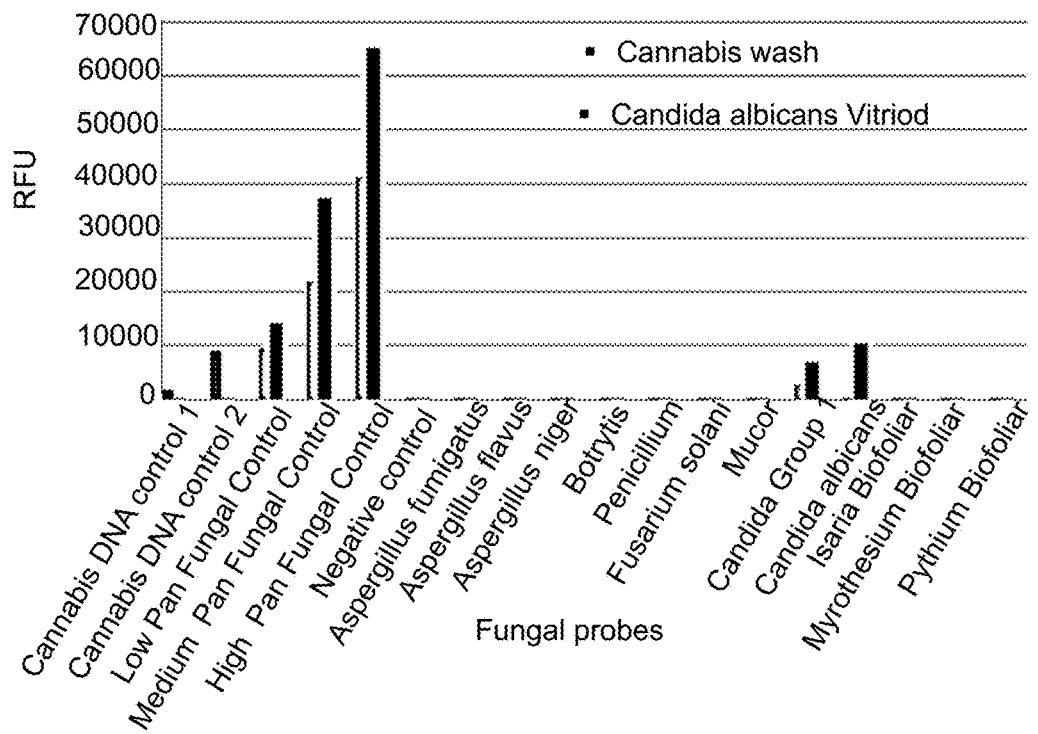

Figure 12

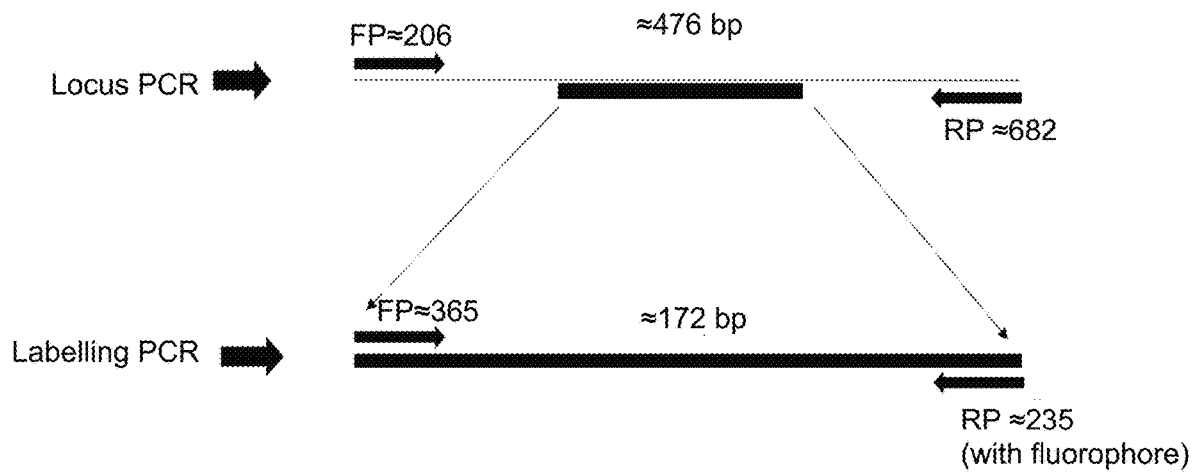

16S rDNA Locus- Low CFU Enterobacteriaceae specific assay

PCR Primers for amplification of the 16S rDNA Enterobacteriaceae HV3 Locus

| Primer name | seq 5'-3' | SEQ ID NO |
|---|---|---|
| 1-PDX-ENT-FP | TTACCTTCGGGCCTCTTGCCATCRGATGTG | 29 |
| 1-PDX-ENT-RP | TTGGAATTCTACCCCCCTCTACRAGACTCAAGC | 30 |

PCR Primers for the labeling amplification rxn. of the 16S rDNA Enterobacteriaceae HV3 Locus

| Primer name | seq 5'-3' | SEQ ID NO |
|---|---|---|
| 2-PDX-ENT-FP | TTATATTGCACAATGGGCGCAAGCCTGATG | 31 |
| 2-PDX-ENT-RP | TTTTGTATTACCGCGGCTGCTGGCA | 32 |

Figure 13A

Data for Produce Tape Pulls and Washed
Hybridization Signal Intensity: Lemon & Bluberry Wash Test

| Sample | Blueberry | | Lemon | |
|---|---|---|---|---|
| Collection Type | Produce Wash | | | |
| Slide | Slide 13 | | | |
| Well | Well 9 | Well 10 | Well 11 | Well 12 |
| Protocol | Wash 1 blueberry in 2 mL 20mM Borate, vortex 30 seconds | | Wash 1 piece moldy lemon in 2ml 20mM Borate, vortex 30 seconds | |
| Dilution Factor | None | 1:20 | None | 1:20 |
| AFum1-ITS2-S-A2 | 65 | 61 | 62 | 57 |
| AFum1-ITS2-S-A3 | 66 | 61 | 58 | 131 |
| AFum1-ITS2-S-A4 | 69 | 78 | 55 | 127 |
| AFum1-ITS2-S-A5 | 80 | 198 | 63 | 161 |
| AFum1-ITS2-S-A6 | 98 | 68 | 59 | 70 |
| AFla1-ITS2-S-A2 | 111 | 65 | 197 | 58 |
| AFla1-ITS2-S-A3 | 64 | 66 | 71 | 49 |
| AFla1-ITS2-S-A4 | 72 | 79 | 54 | 49 |
| AFla1-ITS2-S-A5 | 95 | 71 | 66 | 125 |
| AFla1-ITS2-S-A6 | 59 | 55 | 45 | 47 |
| ANig1-ITS2-S-A2 | 91 | 75 | 61 | 61 |
| ANig1-ITS2-S-A3 | 185 | 68 | 61 | 57 |
| ANig1-ITS2-S-A4 | 93 | 66 | 62 | 61 |
| ANig1-ITS2-S-A5 | 1134 | 74 | 75 | 64 |
| Botr1-ITS2-S-A2 | 26671 | 27605 | 60 | 55 |
| Botr1-ITS2-S-A3 | 26668 | 35611 | 59 | 57 |
| Peni1-ITS2-S-A2 | 63 | 69 | 2444 | 4236 |
| Peni1-ITS2-S-A3 | 71 | 69 | 4905 | 7426 |
| Fusa1-ITS2-S-A2 | 175 | 69 | 59 | 78 |
| Fusa1-ITS2-S-A3 | 71 | 73 | 84 | 62 |
| Muco1-ITS2-S-A2 | 71 | 57 | 58 | 61 |
| Muco1-ITS2-S-A3 | 61 | 290 | 66 | 61 |
| Fung1-ITS2-S-A2 | 20052 | 21412 | 8734 | 7335 |
| Fung1-ITS2-S-A3 | 17626 | 8454 | 5509 | 5030 |

Blueberry is positive for Botrytis, as expected.
Lemon is positive for Penicillium as expected.
Differences in signal intensity for the ON probes are likely due to slide quality.
Simply washing the produce and vortexing for 30 seconds was adequate to obtain hybridization signal.

Figure 17B

Hybridization Signal Intensity: Blueberry Tape Pull Test

| Sample | Moldy Blueberry | | | | | | | | | | | |
|---|---|---|---|---|---|---|---|---|---|---|---|---|
| Collection Type | Tape Pull | | | | | | | | | | | |
| ID | 1A1 | 1A1 | 1A2 | 1A2 | 1A3 | 1A3 | 1B1 | 1B1 | 1B2 | 1B2 | 1B3 | 1B3 |
| Well | Well 1 | Well 4 | Well 2 | Well 5 | Well 3 | Well 6 | Well 7 | Well 10 | Well 8 | Well 11 | Well 9 | Well 12 |
| Collection Point 1 | 500 ul 20 mM Borate Buffer, vortex 30 seconds | | | | | | 500ul 20mM Borate + Triton Buffer, vortex 30 seconds | | | | | |
| Collection Point 2 | | | Add 15 mg zirconia beads, vortex, Heat 5 min 95°C, Vortex 15 seconds | | | | | | Add 15 mg zirconia beads, vortex, Heat 5 min 95°C, Vortex 15 seconds | | | |
| Collection Point 3 | | | | | Heat 5 min 95°C vortex 15 seconds | | | | | | Heat 5 min 95°C vortex 15 seconds | |
| Dilution Factor | NONE | 1:20 | NONE | 1:20 | NONE | 1:20 | NONE | 1:20 | NONE | 1:20 | NONE | 1:20 |
| AFum1-ITS2-S-A2 | 66 | 388 | 83 | 77 | 97 | 313 | 95 | 68 | 76 | 55 | 75 | 60 |
| AFum1-ITS2-S-A3 | 97 | 100 | 82 | 118 | 69 | 56 | 87 | 67 | 185 | 76 | 58 | 52 |
| AFum1-ITS2-S-A4 | 77 | 94 | 82 | 1083 | 87 | 61 | 93 | 84 | 75 | 378 | 73 | 64 |
| AFum1-ITS2-S-A5 | 84 | 151 | 94 | 118 | 96 | 80 | 115 | 85 | 85 | 93 | 190 | 88 |
| AFum1-ITS2-S-A6 | 63 | 75 | 96 | 71 | 78 | 61 | 98 | 74 | 68 | 98 | 70 | 533 |
| AFla1-ITS2-A2 | 200 | 107 | 113 | 61 | 204 | 58 | 105 | 73 | 62 | 68 | 64 | 65 |
| AFla1-ITS2-A3 | 70 | 104 | 64 | 57 | 133 | 281 | 111 | 78 | 377 | 314 | 57 | 50 |
| AFla1-ITS2-A4 | 83 | 90 | 94 | 150 | 99 | 90 | 96 | 222 | 1162 | 86 | 80 | 73 |
| AFla1-ITS2-A5 | 76 | 125 | 92 | 146 | 87 | 174 | 241 | 78 | 115 | 69 | 105 | 85 |
| AFla1-ITS2-A6 | 80 | 153 | 77 | 72 | 78 | 439 | 71 | 86 | 280 | 58 | 62 | 57 |
| ANig1-ITS2-S-A2 | 409 | 178 | 122 | 72 | 80 | 70 | 76 | 71 | 152 | 117 | 65 | 53 |
| ANig1-ITS2-S-A3 | 78 | 292 | 79 | 65 | 715 | 666 | 74 | 70 | 68 | 731 | 70 | 54 |
| ANig1-ITS2-S-A4 | 86 | 76 | 87 | 558 | 78 | 60 | 70 | 81 | 96 | 63 | 478 | 58 |
| ANig1-ITS2-S-A5 | 164 | 70 | 92 | 108 | 197 | 69 | 130 | 75 | 76 | 148 | 73 | 65 |
| Botr1-ITS-S-A2 | 41904 | 26549 | 29181 | 29354 | 25304 | 25685 | 57424 | 33783 | 57486 | 49803 | 33176 | 32153 |
| Botr1-ITS-S-A3 | 36275 | 25518 | 29222 | 27076 | 26678 | 27675 | 49480 | 32899 | 52817 | 34322 | 29693 | 32026 |
| Peri1-ITS-S-A2 | 80 | 81 | 83 | 64 | 96 | 60 | 79 | 80 | 176 | 60 | 385 | 53 |
| Peri1-ITS-S-A3 | 90 | 93 | 81 | 80 | 114 | 59 | 98 | 69 | 470 | 65 | 478 | 56 |
| Fusa1-ITS-S-A2 | 77 | 71 | 69 | 62 | 112 | 55 | 61 | 274 | 617 | 81 | 59 | 757 |
| Fusa1-ITS-S-A3 | 91 | 82 | 107 | 74 | 101 | 65 | 91 | 66 | 123 | 63 | 71 | 583 |
| Muco1-ITS2-S-A2 | 90 | 314 | 73 | 88 | 105 | 61 | 77 | 79 | 741 | 180 | 172 | 74 |
| Muco1-ITS2-S-A3 | 83 | 69 | 73 | 69 | 91 | 67 | 111 | 102 | 455 | 88 | 70 | 133 |
| Fung1-ITS2-S-A2 | 23637 | 18532 | 15213 | 17668 | 18068 | 19762 | 18784 | 15550 | 20625 | 17525 | 25813 | 18269 |
| Fung1-ITS2-S-A3 | 12410 | 8249 | 9281 | 11526 | 8543 | 13007 | 14180 | 14394 | 9905 | 8972 | 15112 | 12678 |

Figure 17C

Hybridization Signal Intensity: Lemon Tape Pull Test

| Sample | Moldy Lemon | | | | |
|---|---|---|---|---|---|
| Collection Type | Tape Pull | | | | |
| ID | 1A1 Lemon | 1A2 Lemon | 1A3 Lemon | 1B1 Lemon | 1B2 Lemon |
| Slide | Slide 13 | | | | |
| Well | Well 1 | Well 2 | Well 3 | Well 4 | Well 5 |
| Collection Point 1 | 500ul 20mM Borate + Triton Buffer, vortex 30 seconds | | | | |
| Collection Point 2 | | Add 15 mg zirconia beads, vortex, Heat 5 min 95°C, Vortex 15 seconds | | | Add 15 mg zirconia beads, vortex, Heat 5 min 95°C, Vortex 15 seconds |
| Collection Point 3 | | | Heat 5 min 95°C vortex 15 seconds | | |
| Dilution Factor | NONE | | | | |
| AFum1-ITS2-S-A2 | 96 | 83 | 75 | 83 | 64 |
| AFum1-ITS2-S-A3 | 221 | 73 | 71 | 66 | 101 |
| AFum1-ITS2-S-A4 | 87 | 88 | 85 | 92 | 122 |
| AFum1-ITS2-S-A5 | 83 | 85 | 91 | 72 | 97 |
| AFum1-ITS2-S-A6 | 448 | 100 | 84 | 114 | 78 |
| AFla1-ITS2-A2 | 85 | 79 | 70 | 66 | 63 |
| AFla1-ITS2-A3 | 77 | 82 | 77 | 79 | 63 |
| AFla1-ITS2-A4 | 133 | 66 | 86 | 60 | 67 |
| AFla1-ITS2-A5 | 96 | 85 | 81 | 98 | 88 |
| AFla1-ITS2-A6 | 68 | 62 | 65 | 106 | 59 |
| ANig1-ITS2-S-A2 | 73 | 88 | 77 | 73 | 73 |
| ANig1-ITS2-S-A3 | 74 | 84 | 81 | 71 | 103 |
| ANig1-ITS2-S-A4 | 90 | 86 | 87 | 74 | 78 |
| ANig1-ITS2-S-A5 | 82 | 93 | 104 | 86 | 161 |
| Botr1-ITS-S-A2 | 82 | 75 | 75 | 77 | 68 |
| Botr1-ITS-S-A3 | 91 | 74 | 83 | 67 | 62 |
| Peni1-ITS-S-A2 | 3824 | 5461 | 5500 | 4582 | 5290 |
| Peni1-ITS-S-A3 | 7586 | 6380 | 11177 | 6528 | 8167 |
| Fusa1-ITS-S-A2 | 101 | 62 | 61 | 70 | 279 |
| Fusa1-ITS-S-A3 | 77 | 122 | 78 | 68 | 233 |
| Muco1-ITS2-S-A2 | 74 | 110 | 89 | 76 | 57 |
| Muco1-ITS2-S-A3 | 132 | 1302 | 90 | 84 | 61 |
| Fung1-ITS2-S-A2 | 8448 | 12511 | 9249 | 12844 | 8593 |
| Fung1-ITS2-S-A3 | 9275 | 8716 | 11585 | 10758 | 4444 |

Figure 17D

Microarray Analysis of Raw Water Filtrate

| Sample ID | 2H | 2H | 9D | 9D | 21 | 21 | 23 | 23 | 25 | 25 | Neg Cntrl. | Neg Cntrl. |
|---|---|---|---|---|---|---|---|---|---|---|---|---|
| Well Number | 1 | 7 | 2 | 8 | 3 | 9 | 4 | 10 | 5 | 11 | 6 | 12 |
| Primer Set | Bacterial Screening set | | | | | | | | | | | |
| Imager calibration D5 High | 311 | 335 | 322 | 379 | 341 | 348 | 345 | 325 | 354 | 343 | 333 | 377 |
| Imager Calibration D2 Med | 280 | 314 | 268 | 286 | 288 | 231 | 253 | 295 | 287 | 295 | 244 | 267 |
| Imager Calibration D3 Low | 245 | 296 | 302 | 324 | 254 | 268 | 293 | 285 | 271 | 340 | 275 | 318 |
| Cannabis cont. E2 | 310 | 330 | 313 | 255 | 323 | 368 | 313 | 322 | 274 | 332 | 322 | 348 |
| Cannabis cont. G1 | 313 | 237 | 298 | 271 | 298 | 288 | 296 | 280 | 249 | 284 | 297 | 352 |
| Cannabis cont. G2 | 208 | 265 | 276 | 250 | 267 | 327 | 255 | 258 | 253 | 282 | 370 | 315 |
| Total Yeast & Mold D2B | 284 | 324 | 290 | 307 | 272 | 361 | 296 | 288 | 271 | 321 | 469 | 292 |
| Total Yeast & Mold D3B | 251 | 259 | 294 | 290 | 309 | 308 | 285 | 281 | 275 | 299 | 293 | 300 |
| Total Yeast & Mold D8B | 282 | 280 | 294 | 280 | 299 | 284 | 275 | 286 | 299 | 259 | 232 | 298 |
| Total Aerobic bacteria D5 | 40101 | 42007 | 47844 | 47680 | 45102 | 44041 | 43520 | 41901 | 46459 | 46783 | 135 | 2743 |
| Total Aerobic bacteria D6 | 14487 | 12314 | 24189 | 26158 | 19712 | 16210 | 17943 | 15474 | 29524 | 18507 | 157 | 787 |
| Total Aerobic bacteria F2 | 4885 | 5629 | 7625 | 6456 | 5807 | 4505 | 5316 | 6022 | 6264 | 6974 | 159 | 310 |
| Negative Control D2 | 293 | 359 | 303 | 339 | 312 | 329 | 306 | 377 | 307 | 335 | 307 | 352 |
| A. fumigatus A2B | 285 | 291 | 284 | 268 | 289 | 265 | 271 | 281 | 269 | 248 | 228 | 285 |
| Aspergillus flavus A2B | 184 | 211 | 201 | 344 | 237 | 179 | 212 | 213 | 163 | 204 | 171 | 236 |
| Aspergillus niger A2 | 226 | 213 | 228 | 273 | 190 | 195 | 245 | 206 | 222 | 209 | 172 | 222 |
| Botrytis spp. B2 | 219 | 285 | 258 | 302 | 275 | 219 | 202 | 288 | 221 | 248 | 214 | 263 |
| Alternaria spp. B1 | 81 | 97 | 76 | 89 | 58 | 76 | 75 | 175 | 117 | 174 | 167 | 210 |
| Penicillium paxillin G1 | 135 | 162 | 215 | 142 | 127 | 161 | 103 | 115 | 238 | 190 | 200 | 199 |
| Penicillium oxalicum G1 | 119 | 107 | 161 | 131 | 135 | 241 | 178 | 158 | 140 | 143 | 194 | 194 |
| Penicillium spp. G1 | 50 | 123 | 179 | 177 | 128 | 138 | 146 | 163 | 148 | 115 | 184 | 247 |
| Can.alb/trop/dub G1 | 261 | 236 | 235 | 230 | 250 | 213 | 276 | 244 | 245 | 237 | 194 | 232 |
| Can.glab/Sach&Kluv spp. B1 | 146 | 165 | 196 | 128 | 160 | 215 | 185 | 217 | 215 | 177 | 225 | 154 |
| Podosphaera spp. B2 | 111 | 119 | 100 | 122 | 192 | 105 | 95 | 43 | 169 | 27 | 143 | 2465 |

Figure 18A

Microarray Analysis of Raw Water Filtrate

| Sample ID | 2H | 2H | 9D | 9D | 21 | 21 | 23 | 23 | 25 | 25 | Neg Cntrl. | Neg Cntrl. |
|---|---|---|---|---|---|---|---|---|---|---|---|---|
| Well Number | 1 | 7 | 2 | 8 | 3 | 9 | 4 | 10 | 5 | 11 | 6 | 12 |
| Primer Set | Bacterial Screening set | | | | | | | | | | | |
| Bile-tolerant Gram-negative F1 | 16026 | 9203 | 13309 | 8426 | 16267 | 14116 | 10557 | 17558 | 15343 | 14285 | 183 | 1060 |
| Bile-tolerant Gram-negative H4 | 12302 | 11976 | 9259 | 10408 | 13055 | 10957 | 11242 | 8416 | 9322 | 11785 | 196 | 440 |
| Bile-tolerant Gram-negative H3 | 5210 | 7921 | 3818 | 3984 | 7224 | 6480 | 4817 | 6933 | 5021 | 5844 | 240 | 218 |
| Total Enterobacteriaceae D3 | 193 | 248 | 389 | 357 | 215 | 214 | 198 | 220 | 276 | 208 | 210 | 245 |
| Total Enterobacteriaceae D4 | 246 | 214 | 297 | 246 | 244 | 224 | 219 | 245 | 252 | 229 | 207 | 245 |
| Total Enterobacteriaceae F1 | 165 | 140 | 158 | 119 | 151 | 180 | 150 | 167 | 182 | 174 | 132 | 137 |
| Total Coliform H1 | 121 | 148 | 158 | 117 | 129 | 117 | 155 | 157 | 125 | 178 | 152 | 186 |
| Escherichia coli specific gene G1 | 31821 | 115 | 132 | 155 | 127 | 62 | 86 | 121 | 59 | 90 | 234 | 218 |
| stx1 gene | 67 | 0 | 2 | 0 | 0 | 23 | 21 | 28 | 0 | 0 | 116 | 129 |
| stx2 gene | 17 | 36 | 174 | 0 | 61 | 47 | 0 | 51 | 33 | 0 | 85 | 113 |
| Salmonella specific gene I1 | 181 | 172 | 245 | 172 | 178 | 212 | 157 | 243 | 174 | 156 | 146 | 169 |
| Bacillus spp. BB1 | 137 | 135 | 174 | 112 | 164 | 143 | 163 | 182 | 168 | 152 | 149 | 137 |
| Pseudomonas spp. G3 | 271 | 74 | 332 | 56 | 366 | 133 | 91 | 114 | 60 | 179 | 555 | 6574 |
| Escherichia coli/Shigella spp. B2 | 103 | 124 | 221 | 124 | 90 | 144 | 130 | 121 | 137 | 143 | 158 | 195 |
| Salmonella enterica/enterobacter spp. B1 | 124 | 98 | 131 | 119 | 136 | 88 | 121 | 77 | 128 | 140 | 124 | 170 |
| Erysiphe Group 2 | 278 | 221 | 237 | 230 | 245 | 254 | 250 | 220 | 205 | 236 | 233 | 209 |
| Trichoderma spp. B1 | 105 | 157 | 204 | 152 | 180 | 154 | 130 | 161 | 201 | 180 | 150 | 187 |
| Escherichia coli J1 | 429 | 431 | 551 | 576 | 549 | 406 | 407 | 484 | 556 | 551 | 293 | 276 |
| Aspergillus niger 1A5 | 218 | 212 | 216 | 297 | 256 | 312 | 221 | 202 | 238 | 231 | 209 | 231 |
| Escherichia coli/Shigella spp. 4B1 | 163 | 193 | 220 | 202 | 308 | 280 | 121 | 271 | 341 | 317 | 124 | 147 |
| Aspergillus fumigatus 1A6 | 713 | 865 | 862 | 830 | 784 | 657 | 827 | 803 | 746 | 812 | 793 | 1022 |
| Aspergillus flavus 1B3 | 155 | 261 | 198 | 156 | 239 | 171 | 250 | 218 | 210 | 258 | 219 | 241 |
| Salmonella enterica 1A3 | 136 | 98 | 85 | 43 | 109 | 47 | 23 | 123 | 70 | 100 | 135 | 161 |
| Salmonella enterica 3B1 | 68 | 53 | 52 | 41 | 60 | 92 | 26 | 28 | 55 | 81 | 116 | 158 |

Figure 18B

MICROARRAY BASED MULTIPLEX PATHOGEN ANALYSIS FOR PLANTS, AGRICULTURE, FOOD, AND WATER

CROSS-REFERENCE TO RELATED APPLICATIONS

This is a continuation under 35 U.S.C. § 120 of pending non-provisional application U.S. Ser. No. 15/388,561, filed Dec. 22, 2016, which claims benefit of priority under 35 U.S.C. § 119(e) of U.S. Ser. No. 62/271,371, filed Dec. 28, 2015, the entirety of both of which are hereby incorporated by reference.

SEQUENCE LISTING

A sequence listing is electronically submitted in text format in compliance with 37 C.F.R. § 1.821(c) and is incorporated by reference herein. The ASCII text file is named D7550CSEQ, was created on Mar. 13, 2020 and is 24 KB in size.

TECHNICAL FIELD

The present disclosure is in the technical field of DNA based pathogen analysis. More particularly, the present disclosure is in the technical field of pathogen analysis on plant, agriculture, food and water material using DNA based microarray technology.

BACKGROUND-PRIOR ART

Prevailing techniques used to identify microbial pathogens rely upon established clinical microbiology monitoring. Pathogen identification is conducted using standard culture and susceptibility tests. These tests require a substantial investment of time, effort, cost as well as labile products. Further, such techniques are not ideal for testing large numbers of samples. Culture-based testing is fraught with inaccuracies which include both false positives and false negatives, as well as unreliable quantification of colony forming units (CFUs). There are issues with the presence of viable but non-culturable microorganisms which do not show up using conventional culture methods. Certain culture tests are very non-specific in terms of detecting both harmful and harmless species which diminishes the utility of the test to determine if there is a threat present in the sample being tested.

In response to challenges including false positives and culturing of microorganisms, DNA-based diagnostic methods such as polymerase chain reaction (PCR) amplification techniques were developed. For use of PCR, the pathogen DNA to be analyzed is extracted from the material prior to analysis, this is a time-consuming and costly step in the process. In an attempt to eliminate the preanalysis extraction step of PCR, Colony PCR was developed. Using cells directly from colonies from plates or liquid cultures, Colony PCR allows PCR! of bacterial cells without sample preparation. This technique was a partial success, as it was not as sensitive as culture which indicated a possible issue with interference of the PCR by constituents in the specimens. The possible interference issue was deemed not significant enough to invalidate the utility of the testing performed. However, such interference can be significant for highly sensitive detection of pathogens for certain types of tests. Consequently, Colony PCR did not eliminate the pre-analysis extraction step for use of PCR, especially for highly sensitive detection of pathogens.

It is known from the literature that 16S DNA in bacteria and the ITS2 DNA in yeast or mold can be PCR amplified, and once amplified can be analyzed to provide information about the specific bacteria or specific fungal contamination in or on plant material. Further, for certain samples such as blood, fecal matter and others, PCR may be performed on the DNA in such samples absent any extraction of the DNA. However, for blood it is known that the result of such direct PCR is prone to substantial sample to sample variation due to inhibition by blood analytes. Additionally, attempts to perform direct PCR analysis on plant matter have generally been unsuccessful, due to heavy inhibition of PCR by plant constituents.

Over time, additional methods and techniques were developed to improve on the challenges of timely and specific detection and identification of pathogens. Immunoassay techniques provide specific analysis, however, the technique is costly in the use of chemical consumables and has a long response time. Optical sensor technologies produce fast real-time detection, however, such sensors lack identification specificity, as they offer a generic detection capability as the pathogen is usually optically similar to its benign background. Quantitative Polymerase Chain Reaction (qPCR) technique is capable of amplification and detection of a DNA sample in less than an hour. However, qPCR is largely limited to the analysis of a single pathogen. Consequently, if many pathogens are to be analyzed concurrently, as is the case with plant, agriculture, food and water material, a relatively large number of individual tests are performed in parallel.

Biological microarrays have become a key mechanism in a wide range of tools used to detect and analyze DNA. Microarray-based detection combines DNA amplification with the broad screening capability of microarray technology. This results in a specific detection and improved rate of process. DNA microarrays can be fabricated with the capacity to interrogate, by hybridization, certain segments of the DNA in bacteria and eukaryotic cells such as yeast and mold. However, processing a large number of PCR reactions for downstream microarray applications is costly and requires highly skilled individuals with complex organizational support. Because of these challenges, microarray techniques have not led to the development of downstream applications.

We have found, that there is a need for a method of DNA based pathogen analysis that interrogates a large number of samples, uses fewer chemical and labile products, and provides faster results while maintaining accuracy, specificity and reliability.

SUMMARY OF EMBODIMENTS

Embodiments of the present disclosure for a microarray based multiplex pathogen analysis method include two steps. One step is DNA amplification of the pathogen DNA of interest. For example, PCR amplification of the sample is conducted prior to biochemical or physical extraction of the pathogen DNA. In this step, the DNA amplification reaction itself provides enrichment of the pathogen DNA(s) of interest. By bypassing the DNA extraction and purification steps, the test procedure is made markedly faster. Further, the test procedure improves sensitivity as the circumvention of DNA extraction procedures mitigates the DNA loss and DNA dilution that accompany DNA extraction. In short, the embodiments do not require pre-analysis DNA extraction nor purification because a microbial pellet obtained from the material is subjected to DNA amplification without purification, the resulting PCR-amplified material is then suitable for analysis.

A second step is DNA microarray analysis of highly repetitive DNA segments in the plant borne pathogens; DNA segments in bacteria or DNA segments in eukaryotic pathogens (yeast and mold), or amplification of specific sequences from unique single copy gene. The repetitive DNA segments are used primarily for highly sensitive detection of specific organisms or for unique biomarker genes or genomic sequences with significant value towards identifying pathogens or even genetic variations within the genome of the host organism (i.e., a plant). In bacteria, the highly repetitive DNA segments are the 16S rDNA gene.

In eukaryotes, the highly repetitive DNA segments are the Internal Transcribed Spacer—2 region, (ITS2). These two types of highly repetitive DNA are known to harbor DNA sequence changes that can be used to distinguish bacteria from each other (16S) and yeast or mold from each other (ITS2). In the present disclosure, a panel of nucleic acid probes is assembled that are capable of recognizing (by DNA hybridization) those DNA sequence changes in bacteria (within 16S), and also within the genes which encode specific pathogen genes and the corresponding sequence changes in yeast or mold (within ITS2). Therefore, subsequent to DNA amplification of non-extracted samples, the amplified 16S DNA can be interrogated on a single microarray, as a single hybridization test, thereby resolving a panel of bacteria which may be present in the plant, agriculture, food, or water specimens. Similarly, subsequent to DNA amplification of non-extracted samples, the amplified ITS2 DNA can be interrogated on a single microarray, as a single hybridization test, thereby resolving a panel of yeast and mold which may be present in the plant, agriculture, food, or water material. The embodiments of the present disclosure with a microarray component of the present disclosure allow a number of individual tests to be performed as a single multiplex test.

Embodiments of the present disclosure are described herein by reference to a microarray based multiplex pathogen analysis. The disclosure is not, however, limited by the #! advantages of the aforementioned embodiment. The present method may also be applied to many types of material capable of generating DNA based pathogen analysis. Further, it should be understood that the disclosed embodiments may be combined with one another. In addition, features of particular embodiments may be exchanged with features of other embodiments.

BRIEF DESCRIPTION OF THE DRAWINGS

These and other features, aspects, and advantages of the embodiments of the present disclosure will become better understood when the following detailed description is read with reference to the accompanying drawings in which like characters represent like parts throughout the drawing, wherein:

FIG. 1 is a graphical representation of the position of PCR primers employed within the 16S locus (all bacteria, SEQ ID NOS: 1-4) and also in the stx1 locus (pathogenic *E. coli*, SEQ ID NOS: 5-8) to be used to PCR amplify unpurified bacterial contamination obtained from *cannabis* wash and related plant wash. These PCR primers are used to amplify and dye label DNA from such samples for bacterial analysis via microarray hybridization.

FIG. 2 is a graphical representation of the position of PCR primers employed within the stx2 locus (pathogenic *E. coli*, SEQ ID NOS: 9-12) and also in the invA locus (all *Salmonella*, SEQ ID NOS: 13-16) to be used to PCR amplify unpurified bacterial contamination obtained from *cannabis* wash and related plant wash. These PCR primers are used to amplify and dye label DNA from such samples for bacterial analysis via microarray hybridization.

FIGS. 6A-6B are Tables which list representative oligonucleotide hybridization probes employed within the 16S locus (bacteria, SEQ ID NOS: 37-79) and ITS2 locus (yeast and mold, SEQ ID NOS: 80-116) to be used to detect the PCR products obtained via amplification of unpurified bacteria, yeast, mold and fungi obtained from *cannabis* wash. These microarray hybridization probes are optimized to support hybridization analysis at room temperature. They are linked to microarray supports via modifications, not shown here.

FIG. 7 displays representative oligonucleotide sequences which are used as microarray probes in an embodiment for DNA microarray based analysis of bacterial pathogens (stx1, stx2, invA, tuf; SEQ ID NOS: 117-120, respectively) and for DNA analysis of the presence of host *cannabis* DNA at the ITS1 region (*Cannabis* spp., SEQ ID NO: 121).

FIG. 9 is an image of the microarray format used to implement the hybridization probes. This representative format comprises 12 microarrays printed on a glass slide, each separated by a Teflon divider (left). Also, shown is a blow-up (right) of one such microarray for the analysis of pathogens in *cannabis* and related plant materials or water samples. The Teflon border about each microarray is fit to localize a 50 uL fluid sample for room temperature hybridization analysis, to be followed by washing at room temperature then microarray image scanning of the dye-labelled pathogen and host plant DNA.

FIG. 11 is representative microarray hybridization data obtained from 5 representative raw *cannabis* wash samples. In each case, the raw pathogen complement of these 5 samples is PCR amplified, then hybridized on the microarray via the microarray probes described above. The data show that in this microarray format, specific bacterial, yeast, mold and fungal contaminants can be specifically identified via room temperature hybridization and washing.

FIG. 12 is representative microarray hybridization data obtained from a representative raw *cannabis* wash sample compared to a representative (raw) highly characterized, *candida* sample. In each case, the raw pathogen complement of each sample is PCR amplified, then hybridized on the microarray via the microarray probes described above. The data show that in this microarray format, specific fungal contaminants can be specifically identified via room temperature hybridization and washing on either raw *cannabis* wash or cloned fungal reference sample.

FIGS. 13A-13B are graphical representations of the position of PCR primers employed in a variation of an embodiment for low level detection of Enterobacteriaceae (SEQ ID NOS: 29-32) and *Aspergillus* spp. (SEQ ID NOS: 33-36). These PCR primers are used to selectively amplify and dye label DNA from targeted organisms for analysis via microarray hybridization.

FIG. 17B is representative microarray hybridization data obtained from blueberry and lemon washes. Both sample types were found to be positive for fungal microbes demonstrating the use of an embodiment for recovery of yeast and mold microbes on fruit surfaces.

FIGS. 17C-17D are representative microarray hybridization data obtained from blueberry (FIG. 17C) and lemon tape (FIG. 17D) pulls. Both the blueberry and lemon washes and tape pulls produced the same yeast and mold microbial profiles demonstrating that either method for recovering microbes from a fruit's surface may be used to obtain a useful analysis of potential pathogens.

FIGS. 18A-18B are representative microarray data from raw water filtrate. Microbes collected via filtration from 5 well-water samples were washed from the water filters much as the surface of plant leaves or fruit surfaces are washed and were found to contain aerobic and bile-tolerant gram negative bacteria in this embodiment. The data in FIGS. 18A-18B demonstrate the same combination of raw sample genotyping, PCR, and microarray analysis used for *cannabis* and fruit washes may also be used to screen for microbial contamination in environmental water samples.

DETAILED DESCRIPTION OF SPECIFIC EMBODIMENTS

Figure 3:
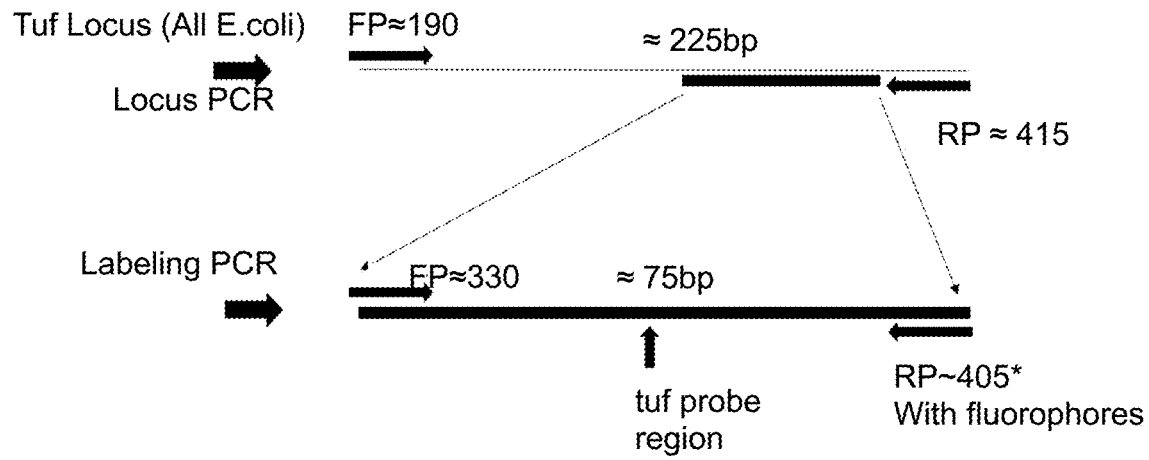
FIG. 3 is a graphical representation of the position of PCR primers employed within the tuf locus (All *E. coli*, SEQ ID NOS: 17-20) to be used to PCR amplify unpurified bacterial contamination obtained from *cannabis* wash and related plant wash. These PCR primers are used to amplify and dye label DNA from such samples for bacterial analysis via microarray hybridization.

The present disclosure provides an improved method for DNA based pathogen analysis. The embodiments of the present disclosure contemplate the use of DNA amplification methodologies, including but not limited to loop-mediated isothermal amplification (LAMP) or polymerase chain reaction (PCR) tests that can selectively amplify the DNA complement of that plant material using unpurified plant and pathogen material. The embodiments are also based on the use of aforementioned PCR-amplified DNA as the substrate for microarray-based hybridization analysis, wherein the hybridization is made simple because the DNA probes used to interrogate the DNA of such pathogens is optimized to function at room temperature. This enables the use of the above mentioned microarray test at ambient temperature, thus bypassing the previously established requirement that testing be supported by an exogenous temperature-regulating device.

Turning now to the Drawings, and referring first to FIG. 1, an exemplar of the first PCR step is shown. As is standard, such PCR reactions are initiated by the administration of PCR Primers. Primers define the start and stopping point of the PCR based DNA amplification reaction. In this embodiment, a pair of PCR reactions is utilized to support the needed DNA amplification. In general, such PCR amplification is performed in series: a first pair of PCRs, with the suffix "P1" in FIG. 1 are used to amplify about 1 µL of any unpurified DNA sample, such as a raw *cannabis* leaf wash for example. About 1 µL of the product of that first PCR reaction is used as the substrate for a second PCR reaction that is used to affix a fluorescent dye label to the DNA, so that the label may be used to detect the PCR product when it binds by hybridization to the microarray. The role of this two-step reaction is to avert the need to purify the pathogen DNA to be analyzed: the first PCR reaction, with primers "P1" is optimized to accommodate the raw starting material, while the second PCR primer pair "P2" are optimized to obtain maximal DNA yield, plus dye labeling from the product of the first reaction. Taken in the aggregate, the sum of the two reactions obviates the need to either purify or characterize the pathogen DNA of interest.

Two types of such two-step PCR reaction are shown in FIG. 1. The top section reveals at low resolution the 16SrDNA region which is amplified in an embodiment, to isolate and amplify a region which may be subsequently interrogated by hybridization. The DNA sequence of this 16S rDNA region is known to vary greatly among different bacterial species. Consequently, having amplified this region by two step PCR, that sequence variation may be interrogated by the subsequent microarray hybridization step.

The bottom section of FIG. 1 displays the stx1 gene locus which is present in the most important pathogenic strains of *E. coli* and which encodes Shigatoxin 1. Employing the same two-step PCR approach, we have designed a set of two PCR primer pairs which, in tandem, can be used to amplify and label unprocessed bacterial samples so as to present the stx1 locus for analysis by microarray based DNA hybridization.

The top section of FIG. 2 displays the stx2 gene locus which is also present in the most important pathogenic strains of *E. coli* and which encodes Shigatoxin 2. Employing the same two-step PCR approach, we have designed a set of two PCR primer pairs which, in tandem, can be used to amplify and label unprocessed bacterial samples so as to present the stx2 locus for analysis by microarray based DNA hybridization.

The bottom section of FIG. 2 displays the invA gene locus which is present in all strains of *Salmonella* and which encodes the Invasion A gene product. Employing the same two-step PCR approach, we have designed a set of two PCR primer pairs which, in tandem, can be used to amplify and label unprocessed bacterial samples so as to present the invA locus for analysis by microarray based DNA hybridization.

FIG. 3 displays the tuf gene locus which is present in all strains of *E. coli* and which encodes the ribosomal elongation factor Tu. Employing the same two-step PCR approach, we have designed a set of two PCR primer pairs which, in tandem, can be used to amplify and label unprocessed bacterial samples so as to present the tuf locus for analysis by microarray based DNA hybridization.

Figure 4:
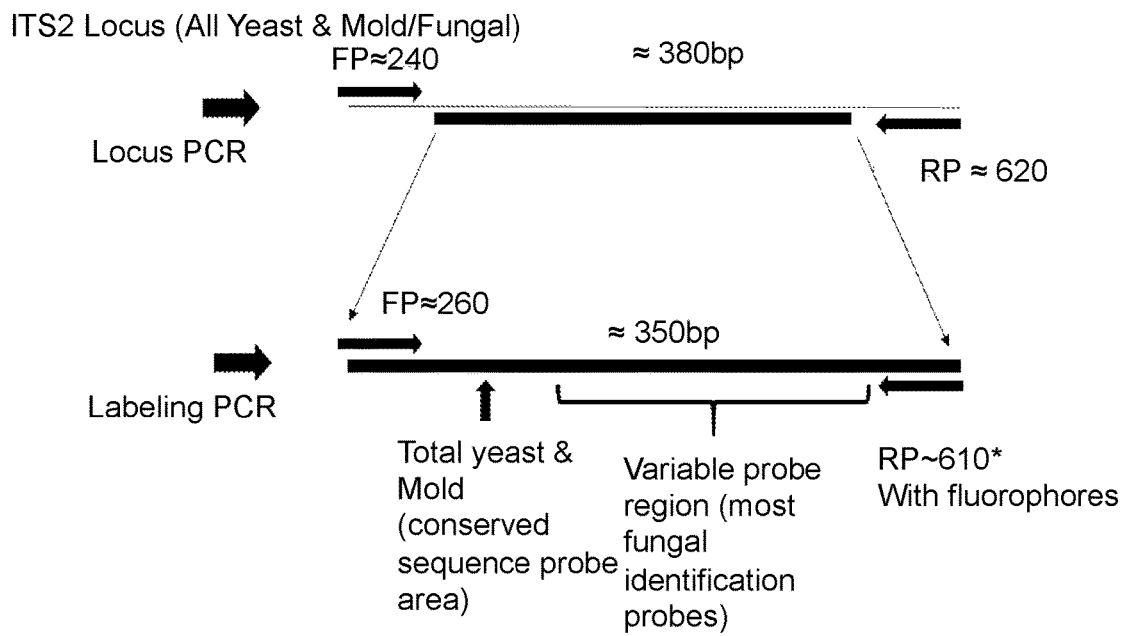
FIG. 4 is a graphical representation of the position of PCR primers employed within the ITS2 locus (All yeast and mold, SEQ ID NOS: 21-24) to be used to PCR amplify unpurified yeast and mold contamination obtained from *cannabis* wash and related plant wash. These PCR primers are used to amplify and dye label DNA from such samples for yeast and mold analysis via microarray hybridization.

FIG. 4 displays the ITS2 region which is present in all eukaryotes, including all strains of yeast and mold and which encodes the intergenic region between ribosomal genes 5.8S and 28S. ITS2 is highly variable in sequence and that sequence variation can be used to resolve strain differences in yeast and mold. Employing the same two-step PCR approach, we have designed a set of two PCR primer pairs which, in tandem, can be used to amplify and label unprocessed yeast and mold samples so as to present the ITS2 region for analysis by microarray based DNA hybridization.

Figure 5:
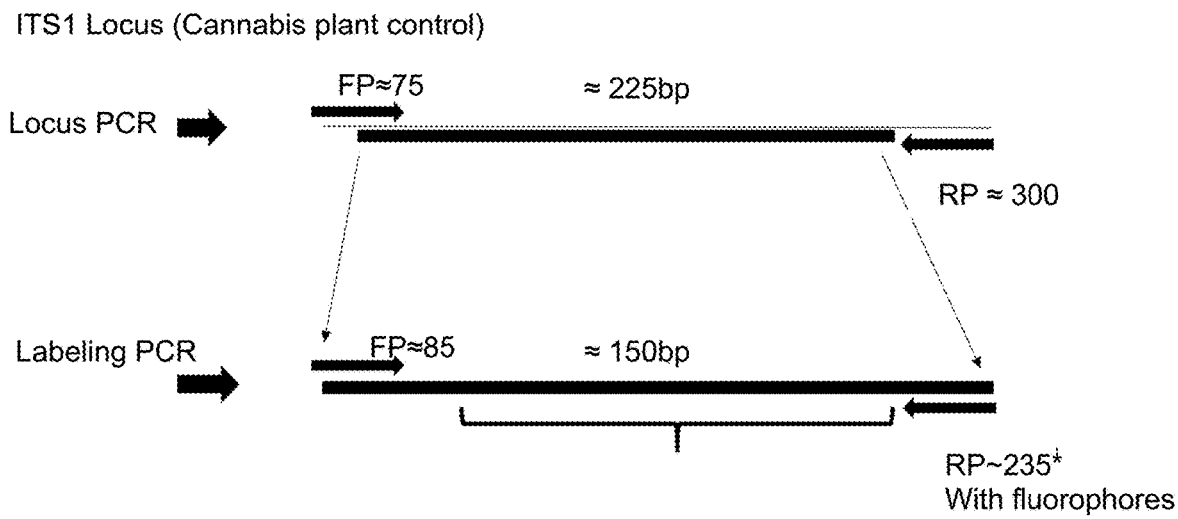
FIG. 5 is a graphical representation of the position of PCR primers employed within the ITS1 locus (*Cannabis* Plant Control, SEQ ID NOS: 25-28) to be used to PCR amplify unpurified DNA obtained from *cannabis* wash. These PCR primers are used to amplify and dye label DNA from such samples for DNA analysis via microarray hybridization. This PCR reaction is used to generate an internal plant host control signal, via hybridization, to be used to normalize bacterial, yeast, mold and fungal signals obtained by microarray analysis on the same microarray.

FIG. 5 displays the ITS1 region which is present in all eukaryotes, including all plants and animals, which encodes the intergenic region between ribosomal genes 18S and 5.8S. ITS1 is highly variable in sequence among higher plants and that sequence variation can be used to identify plant species, and in many cases, animal species as well. Employing the same two-step PCR approach, we have designed a set of two PCR primer pairs which, in tandem, can be used to amplify and label unprocessed *cannabis* samples so as to present the ITS1 region for analysis by microarray based DNA hybridization. The identification and quantitation of the *cannabis* sequence variant of ITS1 is used as an internal normalization standard in the analysis of pathogens recovered from the same *cannabis* samples.

FIG. 6A displays representative oligonucleotide sequences which are used as microarray probes in an embodiment for DNA microarray based analysis of bacterial pathogens. FIG. 6A lists the sequences of a number of representative oligonucleotide probe sequences that have been designed to analyze bacteria, via PCR products obtained by 2 step amplification of the 16S locus in bacteria, as described in FIG. 1. The sequence of those probes has been varied to accommodate the cognate sequence variation which occurs as a function of species difference among bacteria.

FIG. 6B displays representative oligonucleotide sequences which are used as microarray probes in an embodiment for DNA microarray based analysis of fungal pathogens. FIG. 6B lists the sequence of a number of representative oligonucleotide probe sequences that have been designed to analyze fungi, via PCR products obtained by 2 step amplification of the ITS2 region in bacteria, as described in FIG. 4. The sequences of those probes has been varied to accommodate the cognate sequence variation which occurs as a function of species difference among fungi.

FIG. 7 displays representative oligonucleotide sequences which are used as microarray probes in an embodiment for DNA microarray based analysis of bacterial pathogens (stx1, stx2, invA, tuf) and for DNA analysis of the presence of host *cannabis* DNA at the ITS1 region (*Cannabis* spp).

Figure 8:
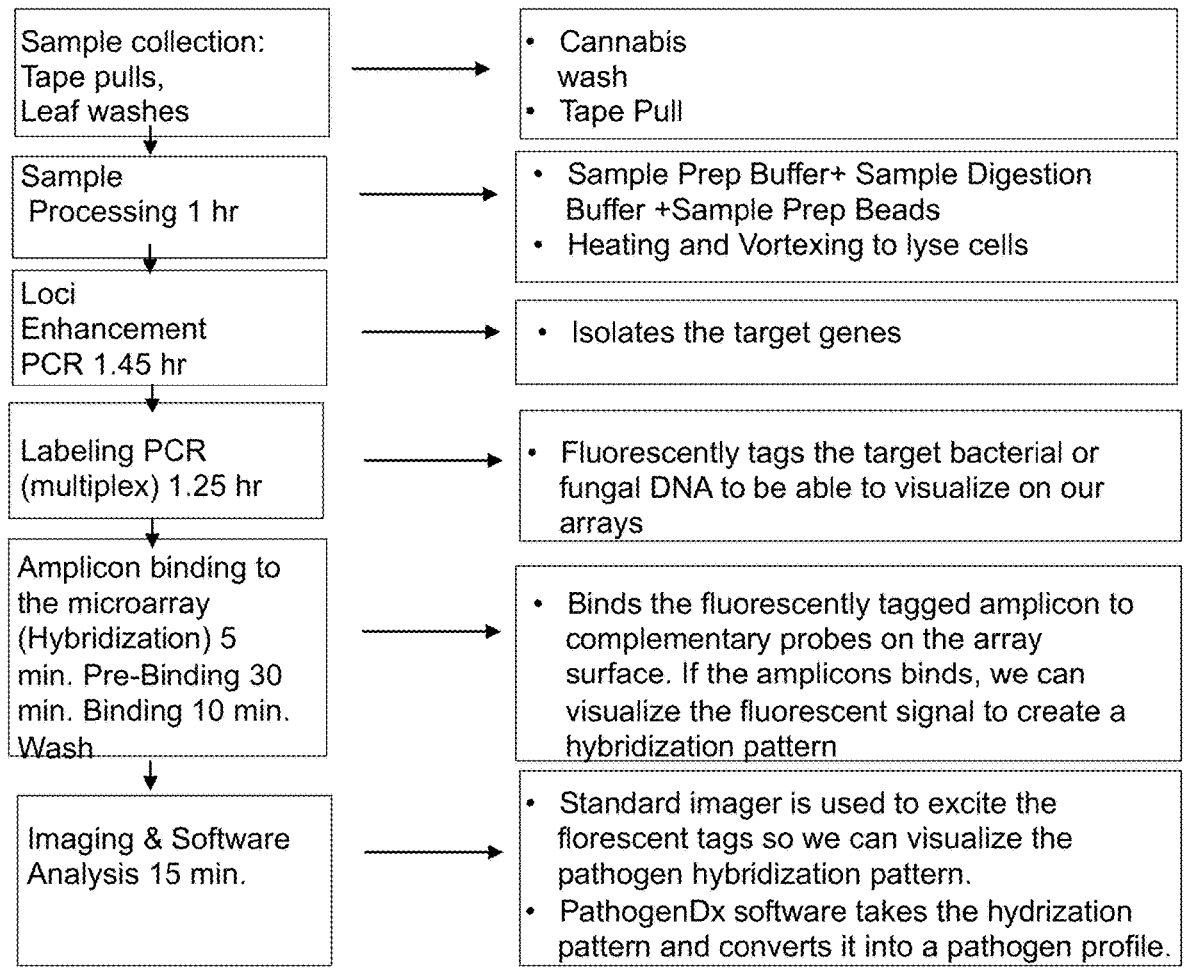
FIG. 8 is a flow diagram to demonstrate the acceptance of unpurified *cannabis* wash or other surface sampling from *cannabis* (and related plant material or water sample) then to PCR amplify the raw *cannabis* or related plant material or water sample, then to perform microarray analysis on that material so as to interrogate the pathogen complement of those plant or water samples.

In FIG. 8, we display a flow diagram to describe how an embodiment is used to analysis the bacterial pathogen or yeast and mold complement of a *cannabis* or related plant sample. Pathogen samples can be harvested from *cannabis* plant material by tape pulling if surface bound pathogen or by simple washing of the leaves or buds or stems, followed by a single multiplex "Loci Enhancement" Multiplex PCR reaction, then followed by a single multiplex "Labelling PCR". A different pair of two step PCR reactions is used to analyze bacteria, than the pair of two step PCR reactions used to analyze yeast and mold. In all cases, the DNA of the target bacteria or yeast or mold of fungi are PCR amplified without extraction or characterization of the DNA prior to two step PCR. Subsequent to the Loci Enhancement and Labelling PCR steps, the resulting PCR product is simply diluted into binding buffer and then applied to the microarray test. The subsequent microarray steps required for analysis (hybridization and washing) are performed at lab ambient temperature.

FIG. 9 provides images of a representative implementation of microarrays used in an embodiment. In this implementation, all oligonucleotide probes required for bacterial analysis along with *cannabis* DNA controls (as in FIG. 6A) are fabricated into a single 144 element (12×12) microarray, along with additional bacterial probes such as those in FIG. 7. In this implementation, all oligonucleotide probes required for yeast and mold analysis along with *cannabis* DNA controls (as in FIG. 6B) are fabricated into a single 144 element (12×12) microarray, along with additional fungal probes such as those in FIG. 7. The arrays are manufactured on PTFE coated glass slides as two columns of 6 identical microarrays. Each of the 12 identical microarrays is capable of performing, depending on the oligonucleotide probes employed, a complete microarray based analysis bacterial analysis or a complete microarray based analysis of yeast and mold. Oligonucleotide probes are linked to the glass support via microfluidic printing, either piezoelectric or contact based or an equivalent. The individual microarrays are fluidically isolated from the other 11 in this case, by the hydrophobic PTFE coating, but other methods of physical isolation can be employed.

Figure 10A:
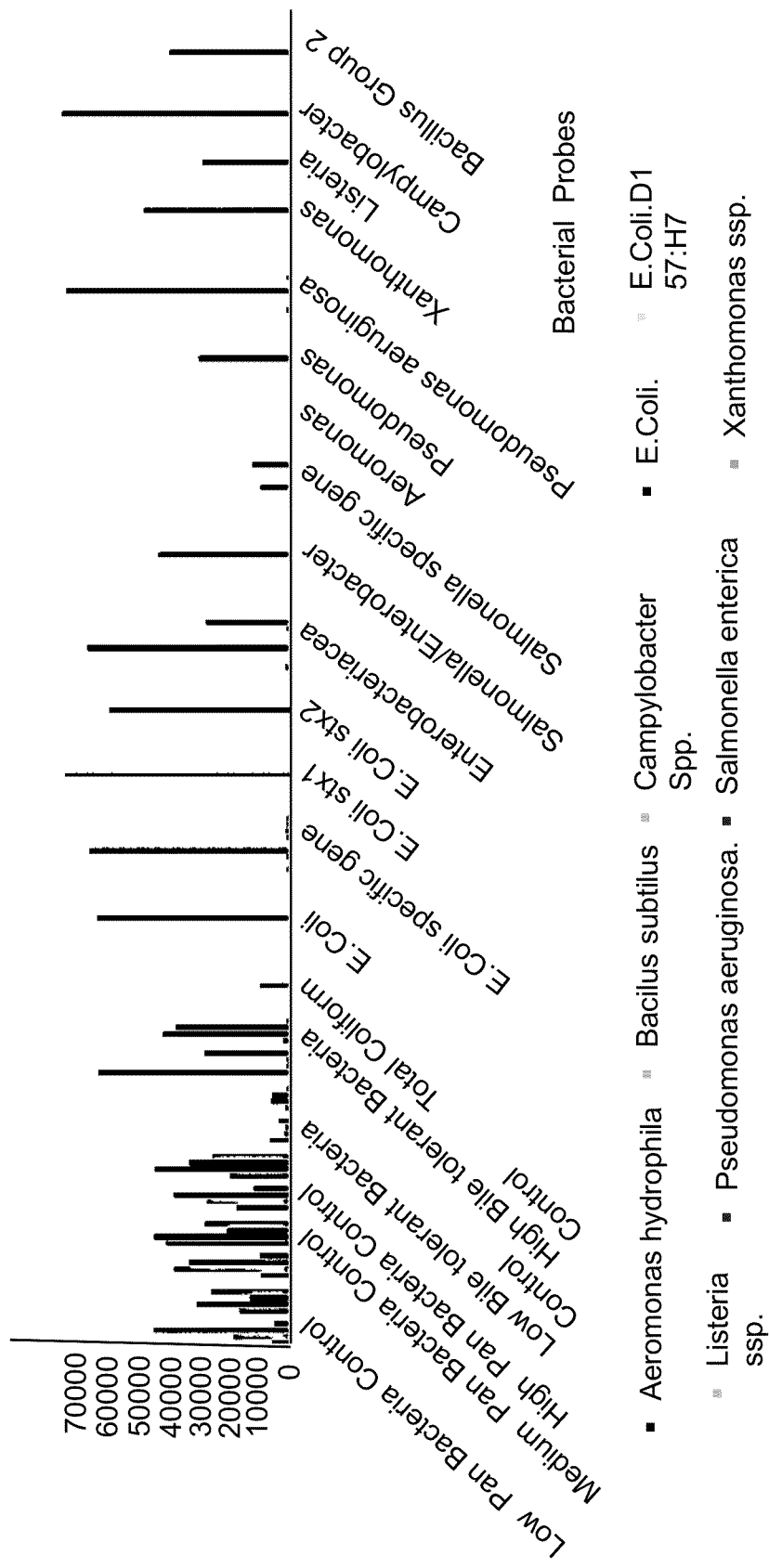
FIGS. 10A-10B are representative microarray hybridization data obtained from purified bacterial DNA standards (FIG. 10A) and purified fungal DNA standards (FIG. 10B). In each case, the purified bacterial DNA (FIG. 10A) is PCR amplified as though it were an unpurified DNA, then hybridized on the microarray via the microarray probes described above. The data show that in this microarray format, each of the bacteria can be specifically identified via room temperature hybridization and washing. Similarly, the purified fungal DNA (FIG. 10B) is PCR amplified as though it were an unpurified DNA, then hybridized on the microarray via the microarray probes described above. The data show that in this microarray format, each of the fungal DNAs can be specifically identified via room temperature hybridization and washing.
Figure 10B:
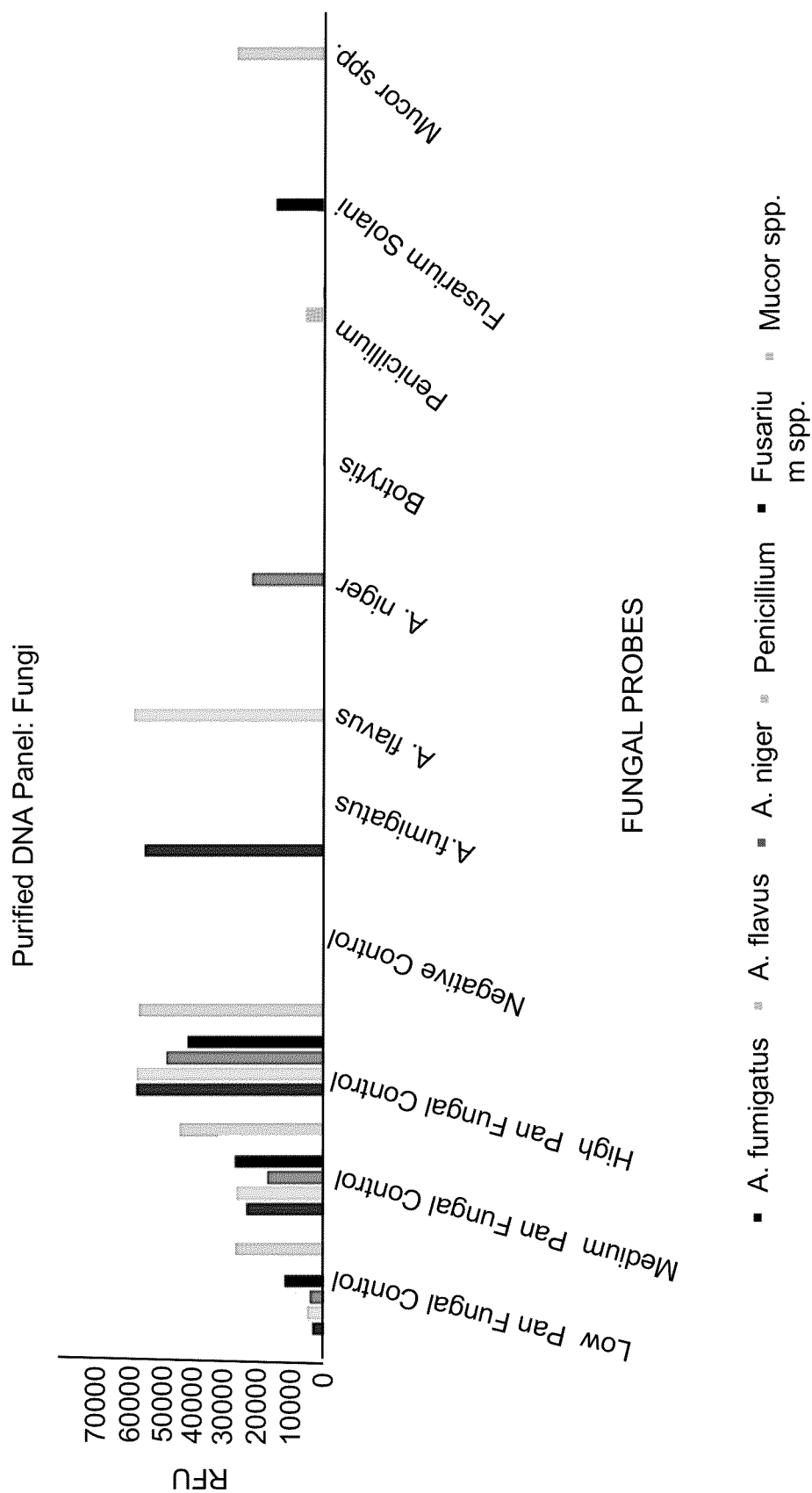

FIGS. 10A-10B display representative DNA microarray analysis of an embodiment. In this case, purified bacterial DNA or purified fungal DNA has been used, to test for affinity and specificity subsequent to the two-step PCR reaction and microarray based hybridization analysis. As can be seen, the oligonucleotide probes designed to detect each of the test bacterial DNA (FIG. 10A) of test fungal DNA (FIG. 10B) have bound to the target DNA correctly via hybridization and thus have correctly detected the bacterium or yeast. Representative microarray hybridization data obtained from purified bacterial DNA standards

PURIFIED DNA BACTERIA PANEL

| | Aeromonas hydrophila | Bacillus subtilis | Campylobactor ssp. |
|---|---|---|---|
| Low Pan Bacteria Control | 4434 | 15943 | 38700 |
| Medium Pan Bacteria Control | 7893 | 33069 | 28705 |
| High Pan Bacteria Control | 14934 | 23469 | 32936 |
| Low Bile tolerant gram negative | 5364 | 947 | 867 |
| High Bile tolerant gram negative | 55228 | 339 | 422 |
| Total Coliform | 106 | 101 | 145 |
| E. coli | 104 | 121 | 127 |
| E. Coli specific gene | 318 | 255 | 422 |
| E. Coli Stx1 | 106 | 116 | 158 |
| E. Coli Stx2 | 100 | 100 | 126 |
| Enterobacteriacea | 885 | 125 | 211 |
| Salmonella/Enterobacter | 115 | 99 | 124 |
| Salmonella specific gene | 189 | 175 | 217 |
| Aeromonas | 10335 | 120 | 123 |
| Pseudomonas | 106 | 107 | 120 |
| Pseudomonas aeriginosa | 169 | 228 | 173 |
| Xanthomonas | 98 | 188 | 122 |
| Listeria | 117 | 263 | 144 |
| Campylobacter | 148 | 120 | 65535 |
| Bacillus Group 2 | 143 | 34517 | 121 |

| | E. coli | E. coli 0157:H7 | Listeria ssp. |
|---|---|---|---|
| Low Pan Bacteria Control | 4215 | 1745 | 14140 |
| Medium Pan Bacteria Control | 8349 | 3638 | 35237 |
| High Pan Bacteria Control | 9827 | 4327 | 16726 |
| Low Bile tolerant gram negative | 2803 | 1801 | 817 |
| High Bile tolerant gram negative | 24172 | 14746 | 1482 |
| Total Coliform | 8276 | 9175 | 139 |
| E. coli | 55419 | 47805 | 151 |
| E. Coli specific gene | 57638 | 57112 | 521 |
| E. Coli Stx1 | 134 | 65535 | 151 |
| E. Coli Stx2 | 169 | 52041 | 135 |
| Enterobacteriacea | 58323 | 36641 | 179 |
| Salmonella/Enterobacter | 190 | 160 | 144 |
| Salmonella specific gene | 208 | 392 | 212 |
| Aeromonas | 127 | 139 | 163 |
| Pseudomonas | 130 | 126 | 133 |
| Pseudomonas aeriginosa | 318 | 1217 | 208 |
| Xanthomonas | 133 | 143 | 143 |
| Listeria | 136 | 128 | 24783 |
| Campylobacter | 139 | 153 | 224 |
| Bacillus Group 2 | 128 | 150 | 137 |

| | Pseudomonas aeruginosa | Salmonella enterica | Xanthomonas ssp. |
|---|---|---|---|
| Low Pan Bacteria Control | 26431 | 11167 | 22152 |
| Medium Pan Bacteria Control | 39002 | 17682 | 24141 |
| High Pan Bacteria Control | 38682 | 28596 | 22072 |
| Low Bile tolerant gram negative | 4852 | 4453 | 461 |
| High Bile tolerant gram negative | 36337 | 32579 | 356 |
| Total Coliform | 145 | 204 | 196 |
| E. coli | 144 | 83 | 147 |
| E. Coli specific gene | 695 | 641 | 461 |
| E. Coli Stx1 | 142 | 196 | 145 |
| E. Coli Stx2 | 147 | 117 | 132 |
| Enterobacteriacea | 375 | 23847 | 204 |
| Salmonella/Enterobacter | 138 | 37520 | 144 |
| Salmonella specific gene | 211 | 8124 | 231 |
| Aeromonas | 142 | 99 | 146 |
| Pseudomonas | 25866 | 77 | 153 |
| Pseudomonas aeriginosa | 64437 | 135 | 424 |
| Xanthomonas | 221 | 80 | 41903 |
| Listeria | 144 | 79 | 131 |
| Campylobacter | 144 | 88 | 160 |
| Bacillus Group 2 | 139 | 81 | 134 |

Representative Microarray Hybridization Data Obtained from Purified Bacterial DNA Standards FIG. 11 displays representative DNA microarray analysis of an embodiment. In this case, 5 different unpurified raw *cannabis* leaf wash samples have been used, to test for affinity and specificity subsequent to the two-step PCR reaction and microarray based hybridization analysis. Both bacterial and fungal analysis has been performed on all 5 leaf wash samples, by dividing each sample into halves and subsequently processing them each for analysis of bacteria or for analysis of yeast and mold. The data of FIG. 11 were obtained by combining the outcome of both assays. The data of FIG. 11 show that the combination of two step PCR and microarray hybridization analysis, as described in FIG. 8, can be used to interrogate the pathogen complement of a routine *cannabis* leaf wash. It is expected, but not shown that such washing of any plant material could be performed similarly.

FIG. 12 displays representative DNA microarray analysis of an embodiment. In this case, (1) unpurified raw *cannabis* leaf wash samples was used and was compared to data obtained from a commercially-obtained homogenous vitroid culture of live *Candida*, a fungus (more specifically a type of yeast) to test for affinity and specificity subsequent to the two-step PCR reaction and microarray based hybridization analysis. Both *cannabis* leaf wash and cultured fungal analysis have been performed by processing them each for analysis via probes specific for fungi (see FIGS. 6B and 7). The data of FIG. 12 were obtained by combining the outcome of analysis of both the leaf wash and vitroid culture samples. The data of FIG. 12 show that the combination of two step PCR and microarray hybridization analysis, as described in FIG. 8, can be used to interrogate the fungal complement of a routine *cannabis* leaf wash as adequately as can be done with a pure (live) fungal sample. It is expected, but not shown that fungal analysis via such washing of any plant material could be performed similarly.

Figure 13B:
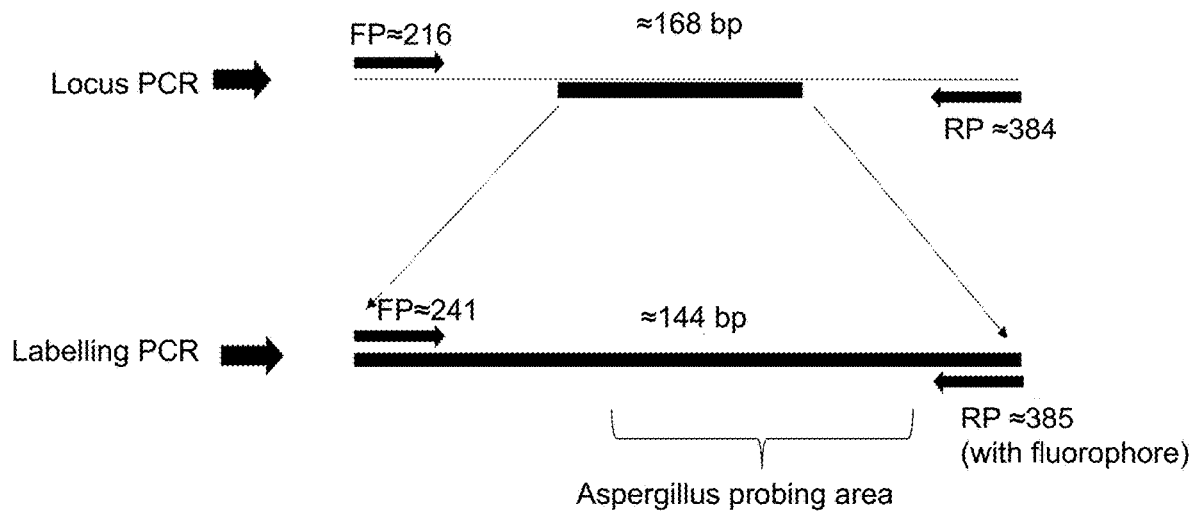

FIGS. 13A-13B are a variation of the assay described in the top section of FIG. 1 as shown in FIG. 13A. This version of the assay was designed to detect the presence of very low levels of pathogenic Enterobacteriaceae. Instead of amplifying the HV3 region of the 16S rDNA loci for all bacteria, the PCR primers are specific for the family Enterobacteriaceae. Increased sensitivity is achieved by the elimination of the testing for background species of bacteria that would lead to reagent exhaustion and potentially mask the detection of low level pathogens. One CFU detection of *E. coli* and *Salmonella enterica* was demonstrated with this version of the assay as shown in FIG. 13A. FIG. 13B shows a variation on the assay described in FIG. 4. This version of the assay replaces the universal fungal PCR primers employed in FIG. 4 with PCR primers specific for the genus *Aspergillus*. As in the corresponding Enterobacteriaceae assay, increased sensitivity is achieved by eliminating the competition for amplification reagents by background species. One CFU detection of *Aspergillus niger, Aspergillus flavus* and *Aspergillus fumigatus* has been demonstrated with this version of the assay, as shown in FIG. 13B.

Figure 14A:
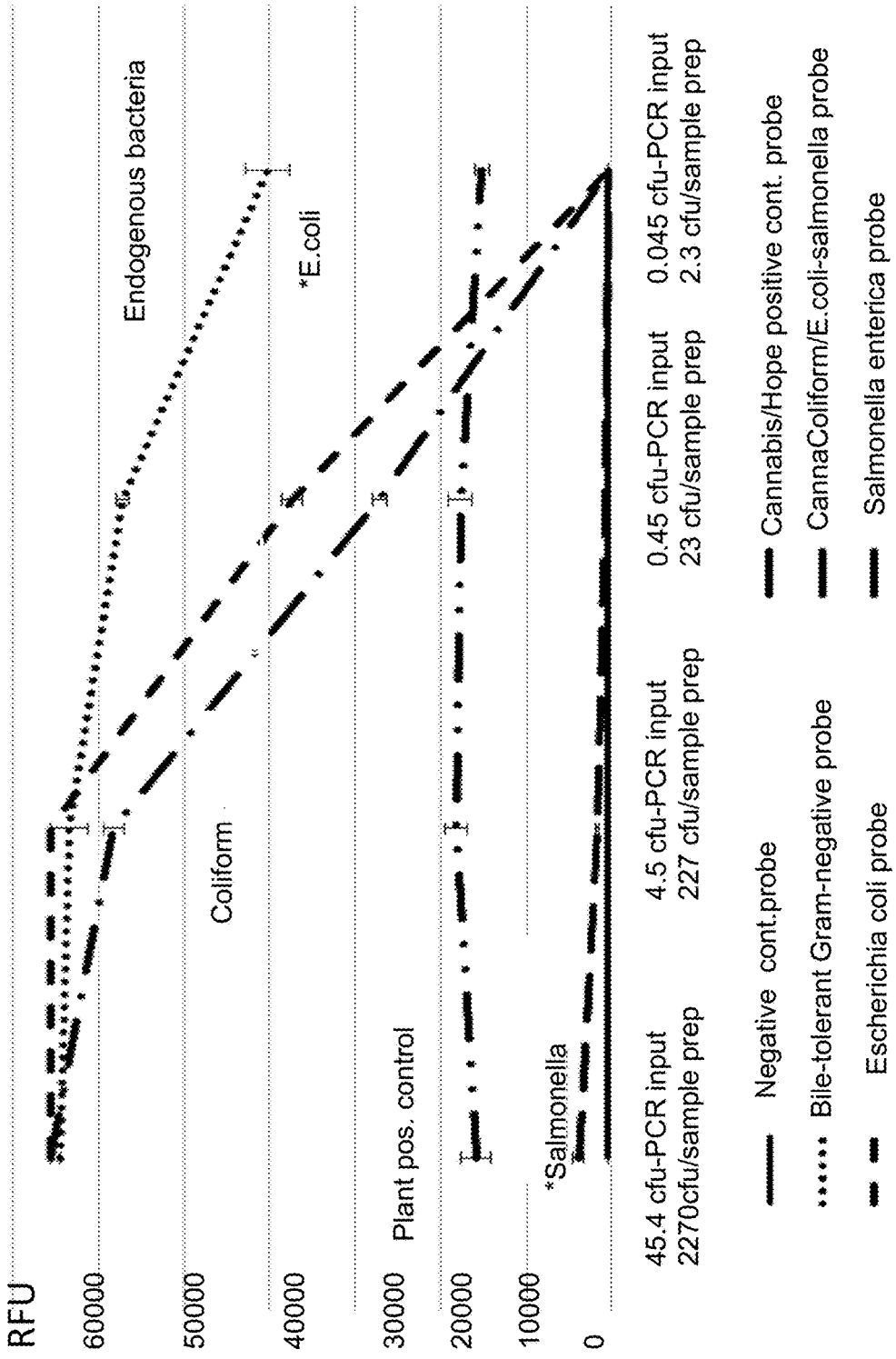
FIGS. 14A-14B are graphical representations of microarray hybridization data demonstrating low level detection of *E. coli* O157:H7 and *E. coli* 0111 from certified reference material consisting of enumerated colonies of specified bacteria spiked onto *Humulus lupulus*, (Hop plant).
Figure 14B:
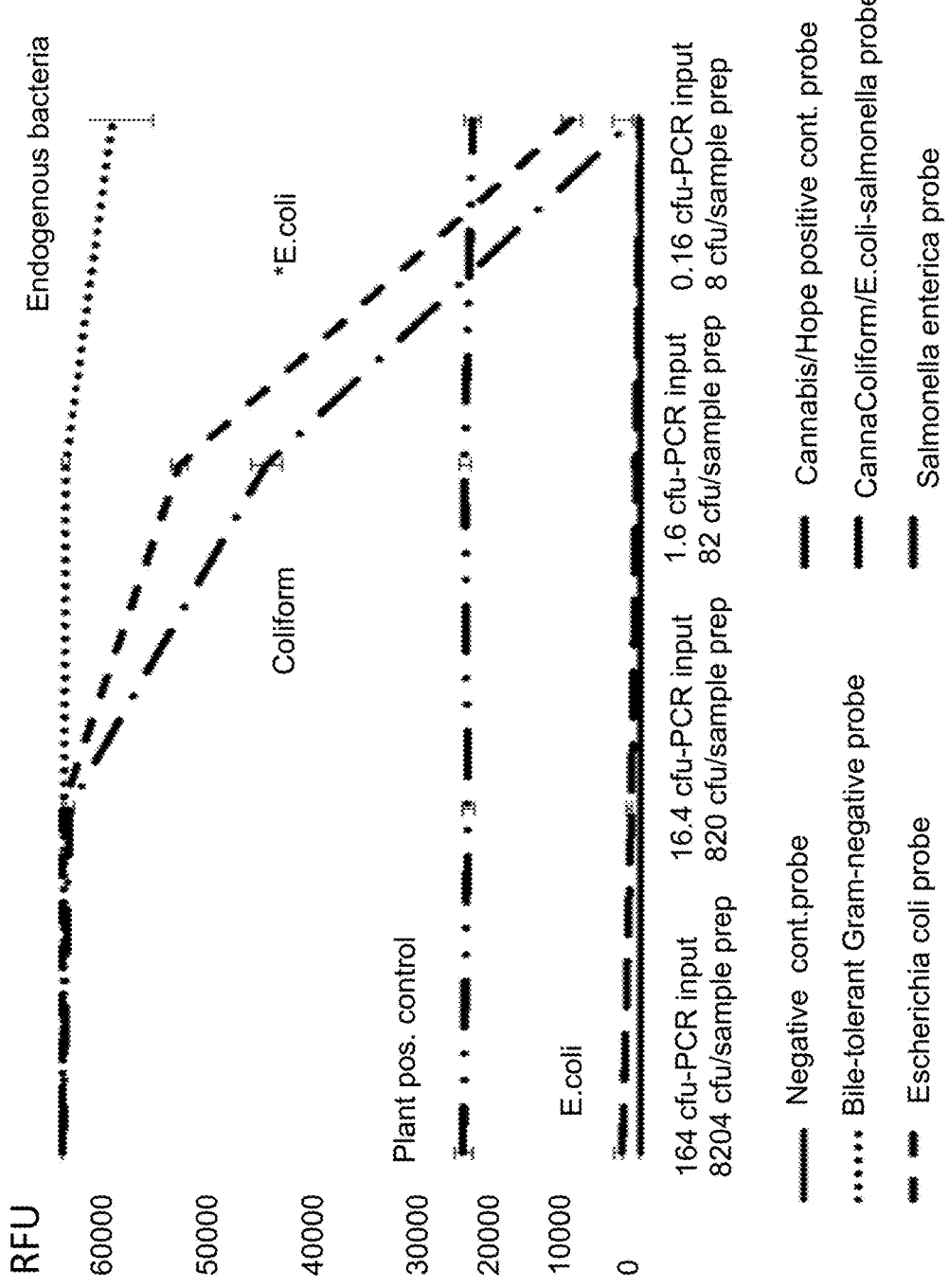
Figure 15:
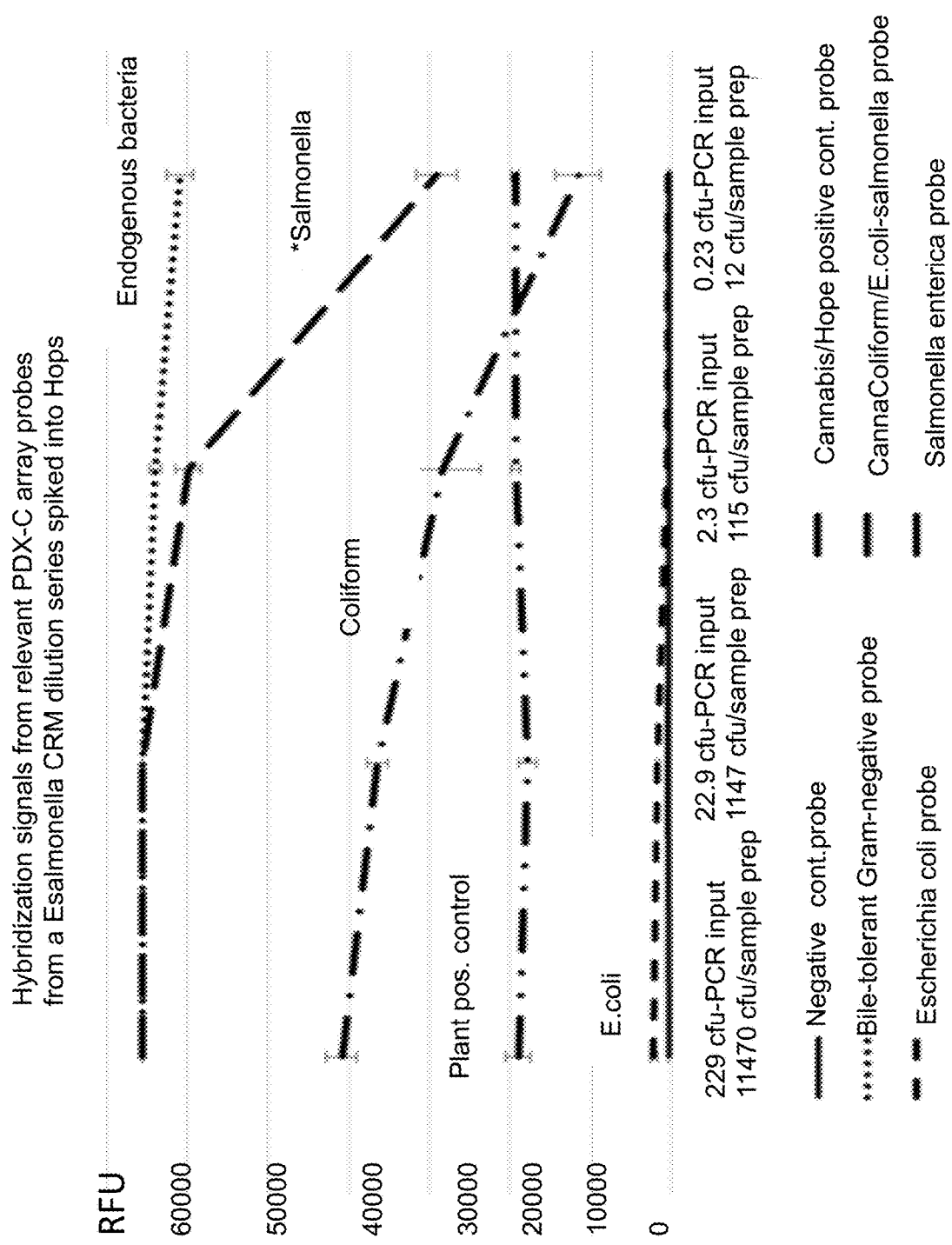
FIG. 15 is a graphical representation of microarray hybridization data demonstrating low level detection of *Salmonella enterica* from certified reference material consisting of enumerated colonies of specified bacteria spiked onto *Humulus lupulus*, (Hop plant).

FIGS. 14 and 15 display representative DNA microarray analysis of an embodiment: to demonstrate assay sensitivity over a range of microbial inputs. In this case, certified reference material consisting of enumerated bacterial colonies of *E. coli* O157:H7, *E. coli* O111 (FIG. 14) and *Salmonella enterica* (FIG. 15) were spiked as a dilution series onto a hops plant surrogate matrix then processed using the assay version described in FIGS. 13A-13B. Hybridization results from relevant probes from FIGS. 6A-6B are shown. The larger numbers on the x-axis represents the total number of bacterial colony forming units (CFU) that were spiked onto each hops plant sample, whereas the smaller numbers on the x-axis represent the number of CFU's of the spiked material that were actually inputted into the assay. Only about $\frac{1}{50}$ of the original spiked hops sample volume was actually analyzed on the microarray. Thus, the smaller numbers upon the x-axis of FIGS. 14 & 15 are exactly $\frac{1}{50}$th that of the total (lower) values. As is seen, FIGS. 14 and 15 both show that the microarray test of an embodiment can detect less than 1 CFU per microarray assay. The nucleic acid targets within the bacterial genomes displayed in FIGS. 14 and 15 comprise 16S rDNA. There are multiple copies of the 16S rDNA gene in each of these bacterial organisms, which enables detection at <1 CFU levels. Since a colony forming unit approximates a single bacterium in many cases, the data of FIGS. 14 and 15 demonstrate that the present microarray assay has sensitivity which approaches the ability to detect a single (or a very small number) of bacteria per assay. Similar sensitivity is expected for all bacteria and eukaryotic microbes in that it is known that they all present multiple copies of the ribosomal rDNA genes per cell.

Figure 16A:
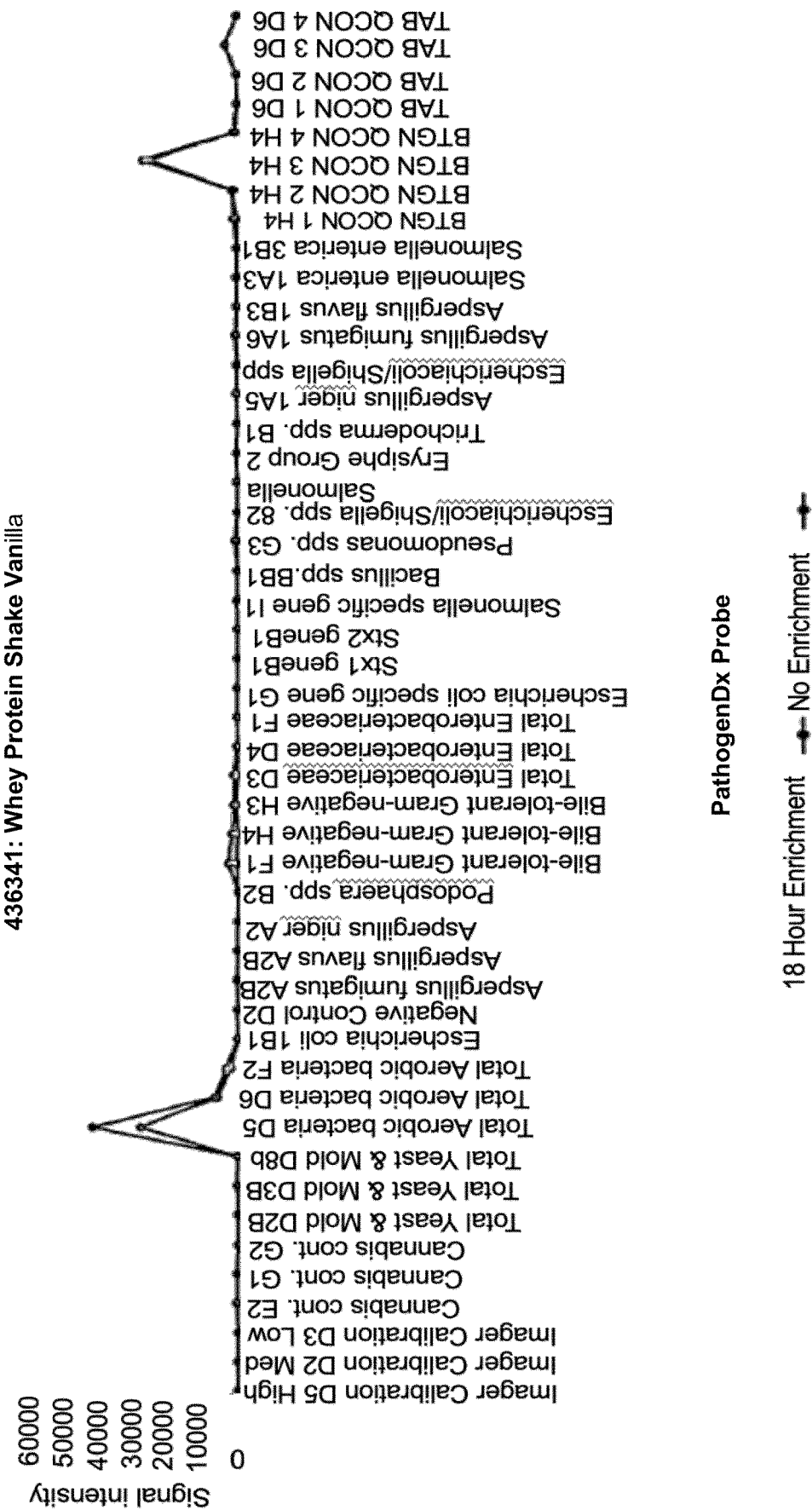
FIGS. 16A-16R are a collection of representative microarray hybridization data obtained from powdered dry food samples with no enrichment and 18 hour enrichment for comparison. The data shows that bacterial microbes were successfully detected without the need for enrichment.
Figure 16B:
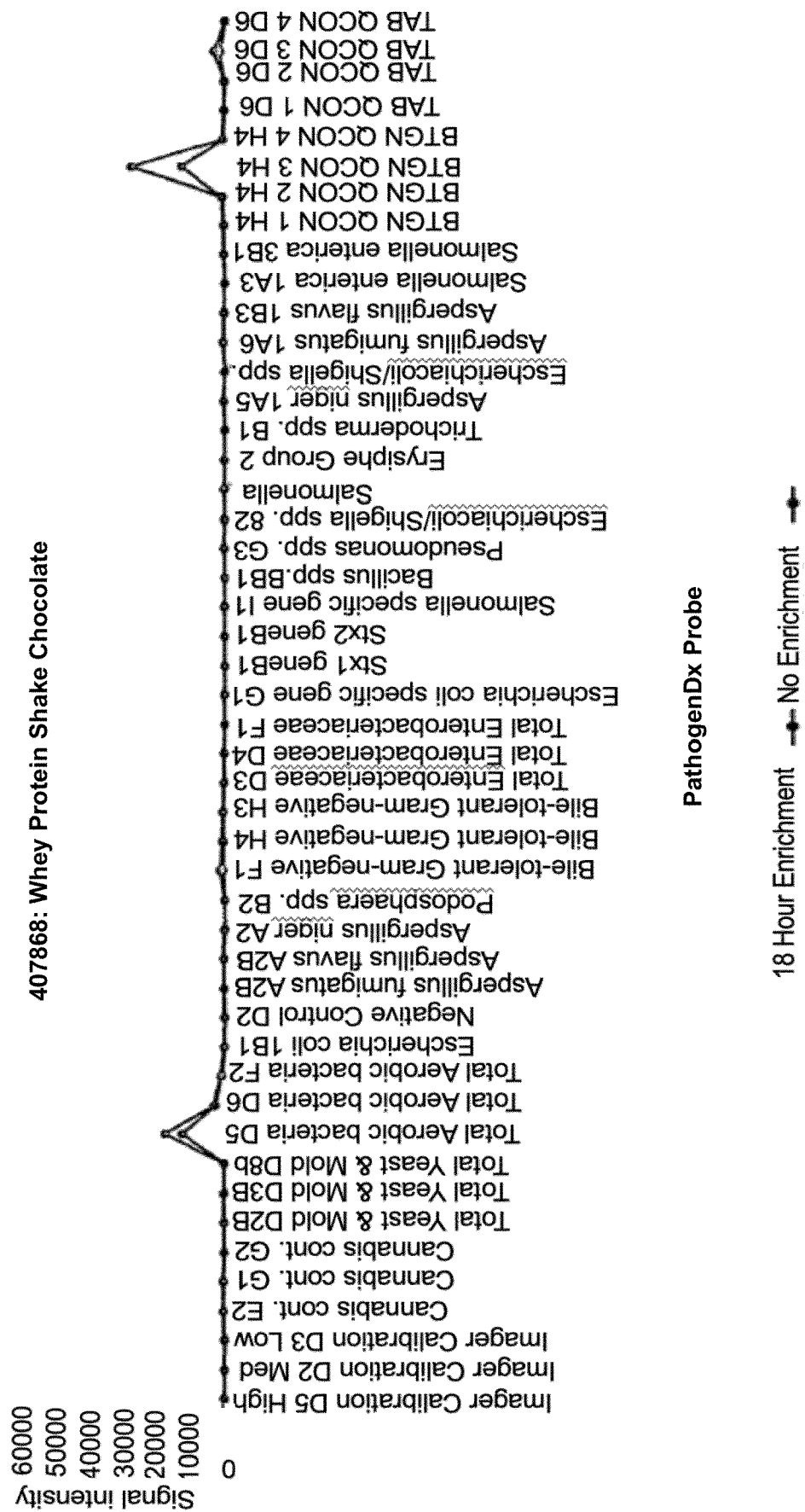
Figure 16C:
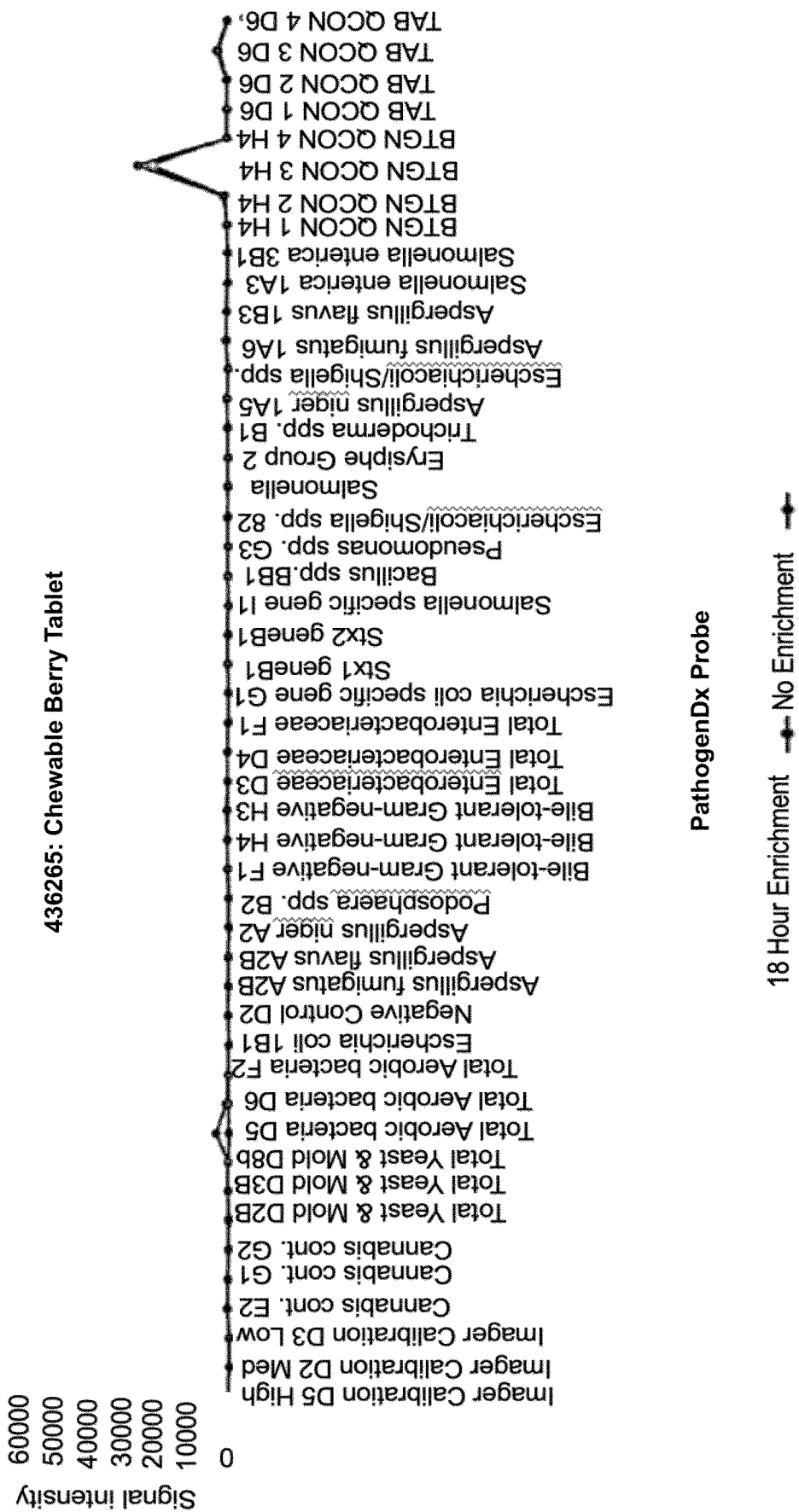
Figure 16D:
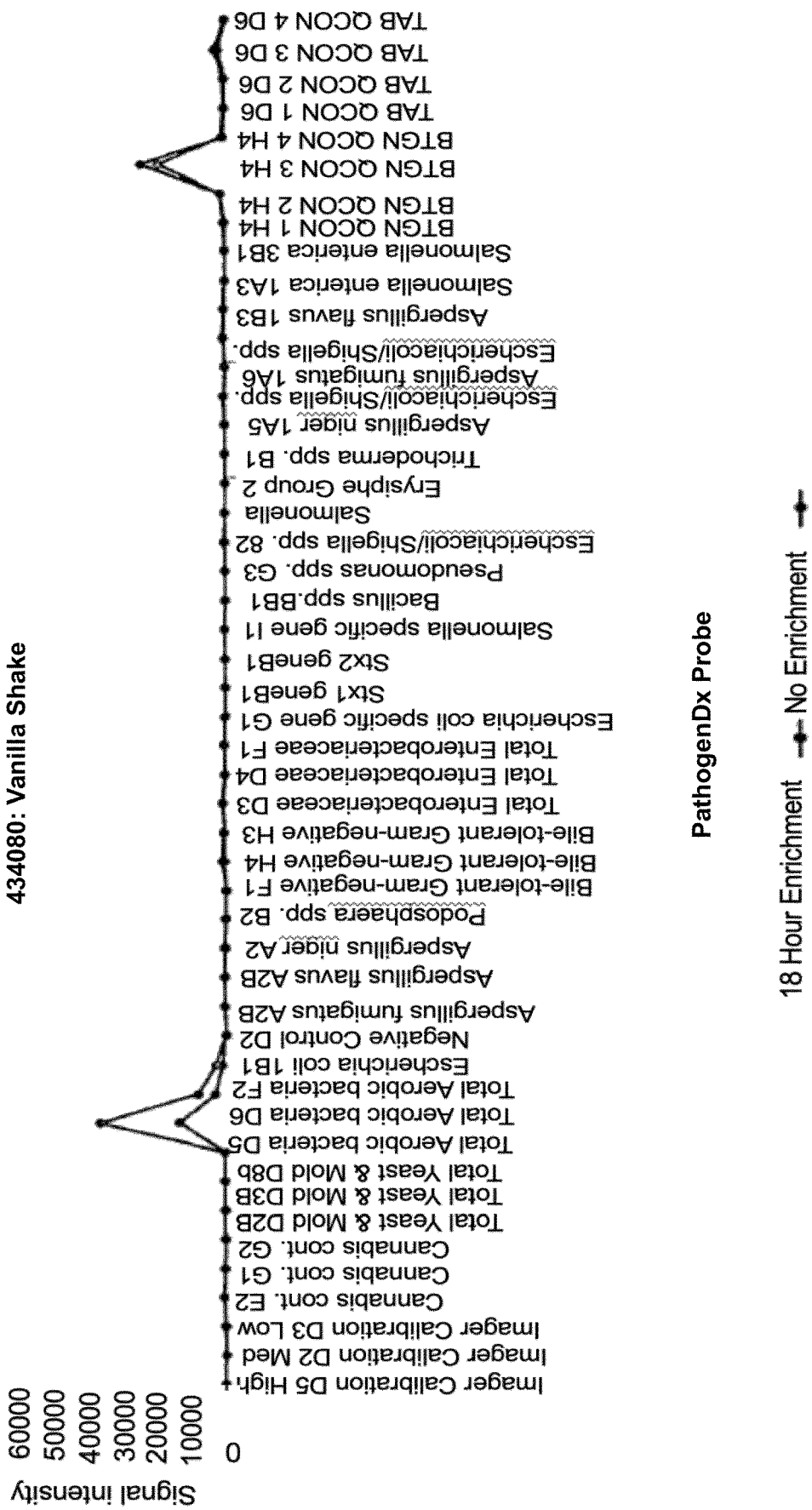
Figure 16E:
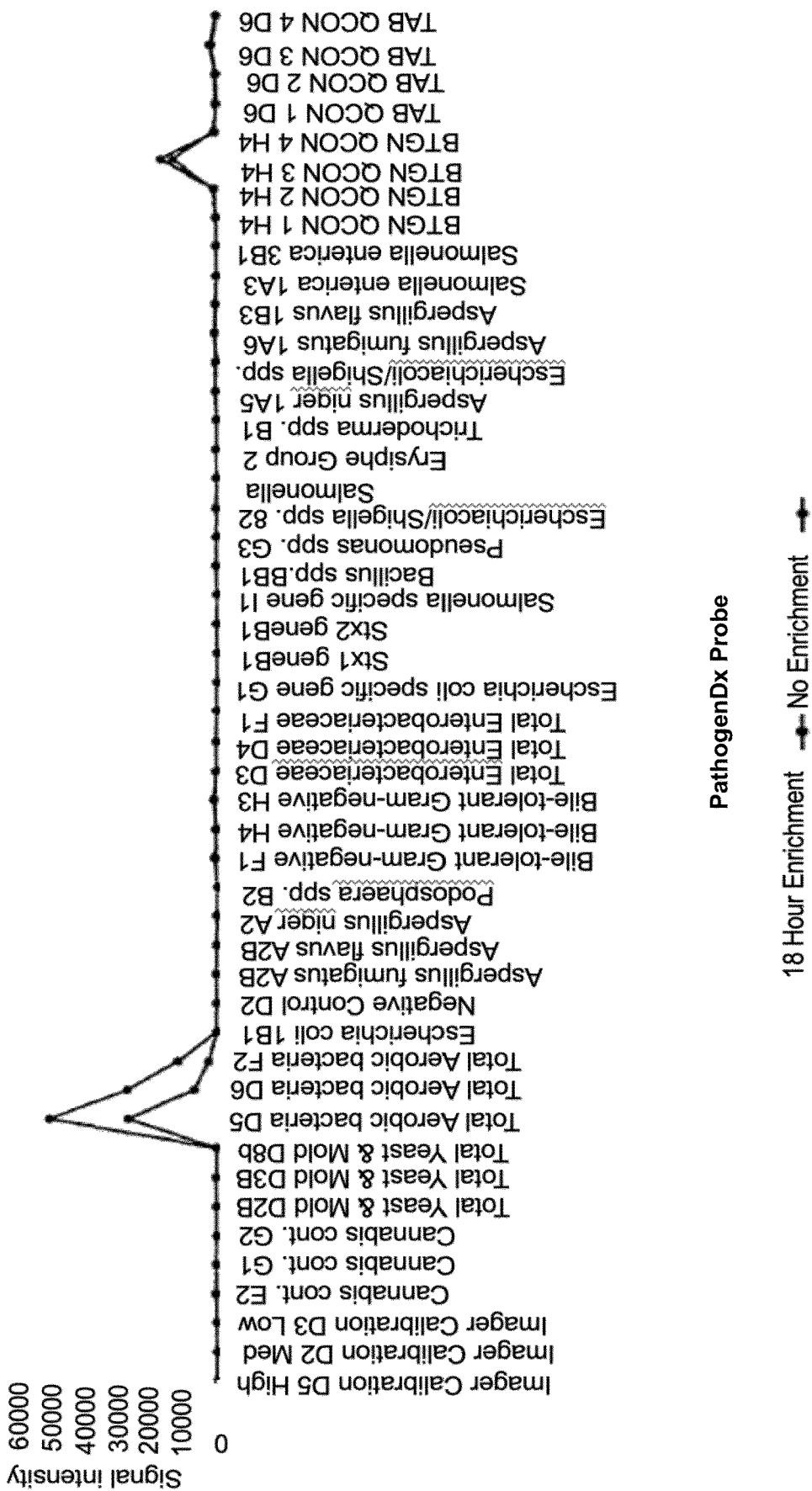
Figure 16F:
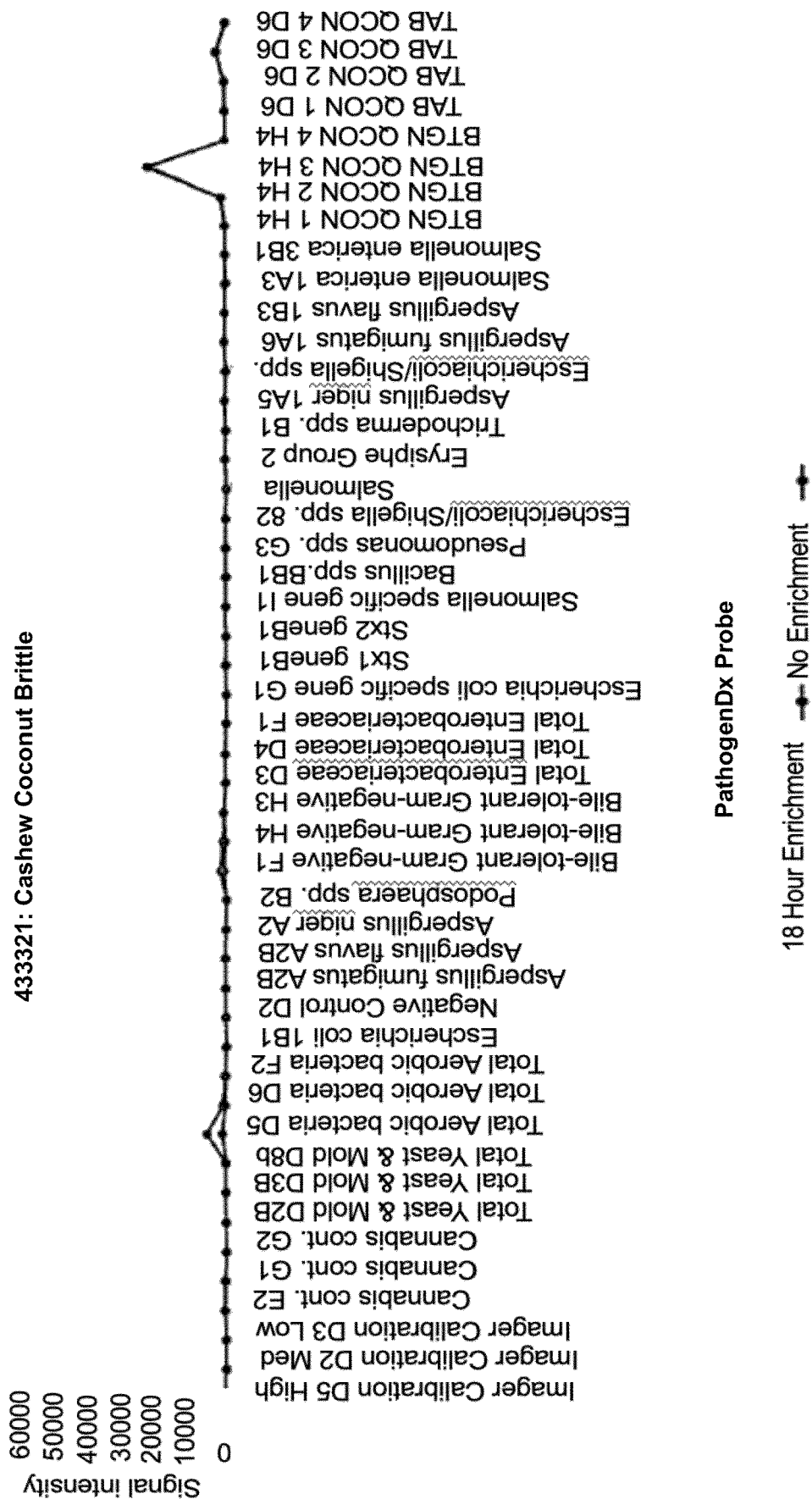
Figure 16G:
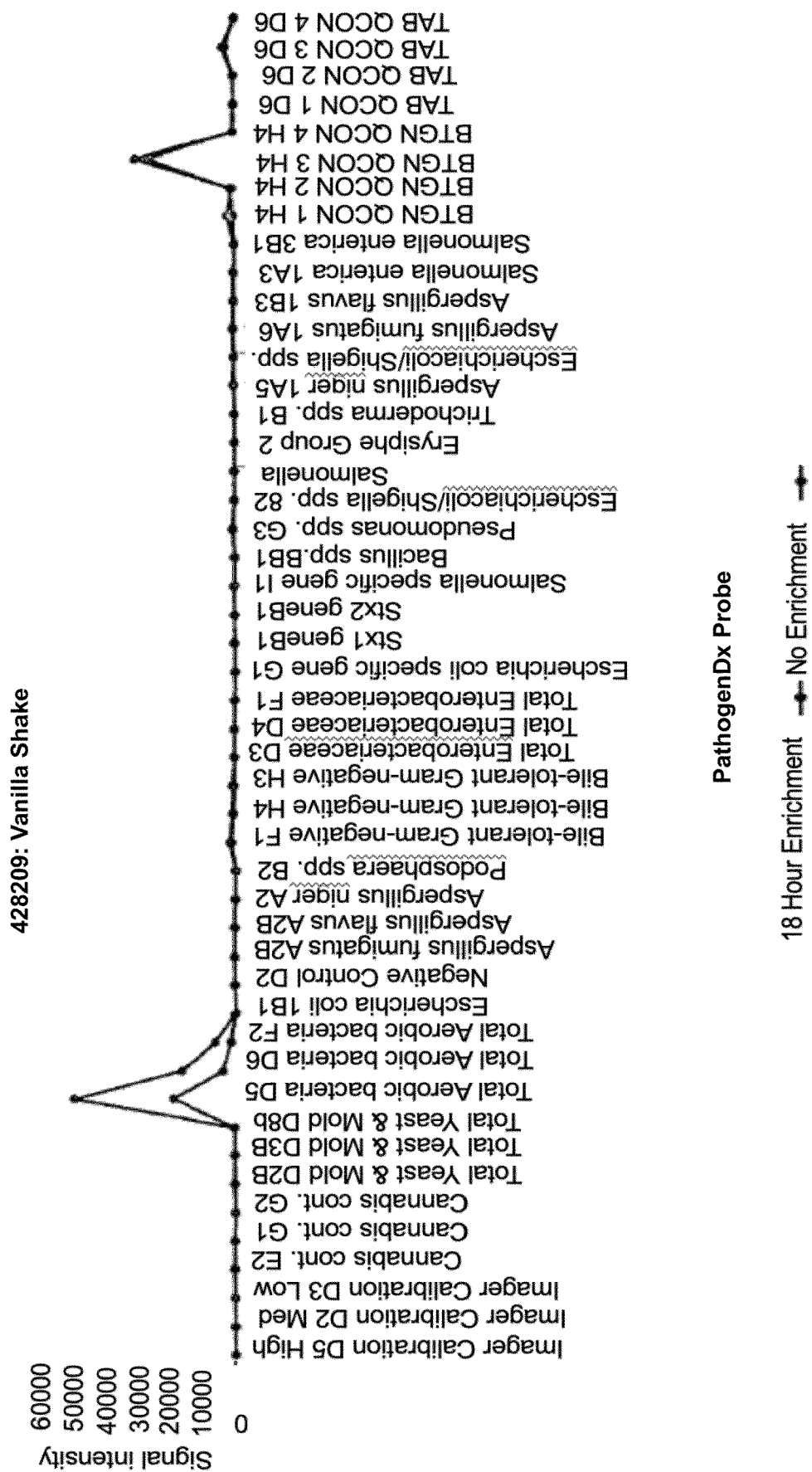
Figure 16H:
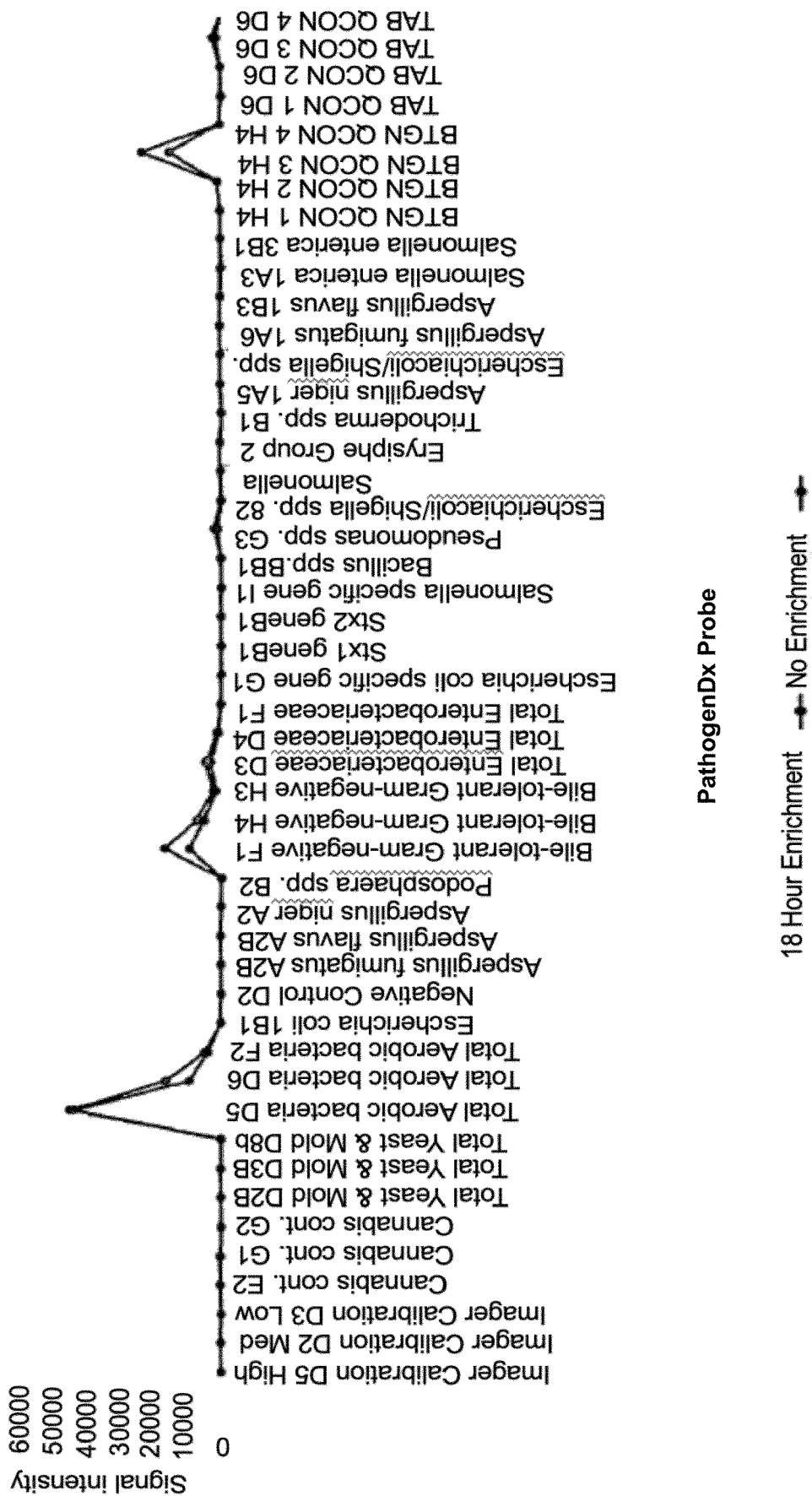
Figure 16I:
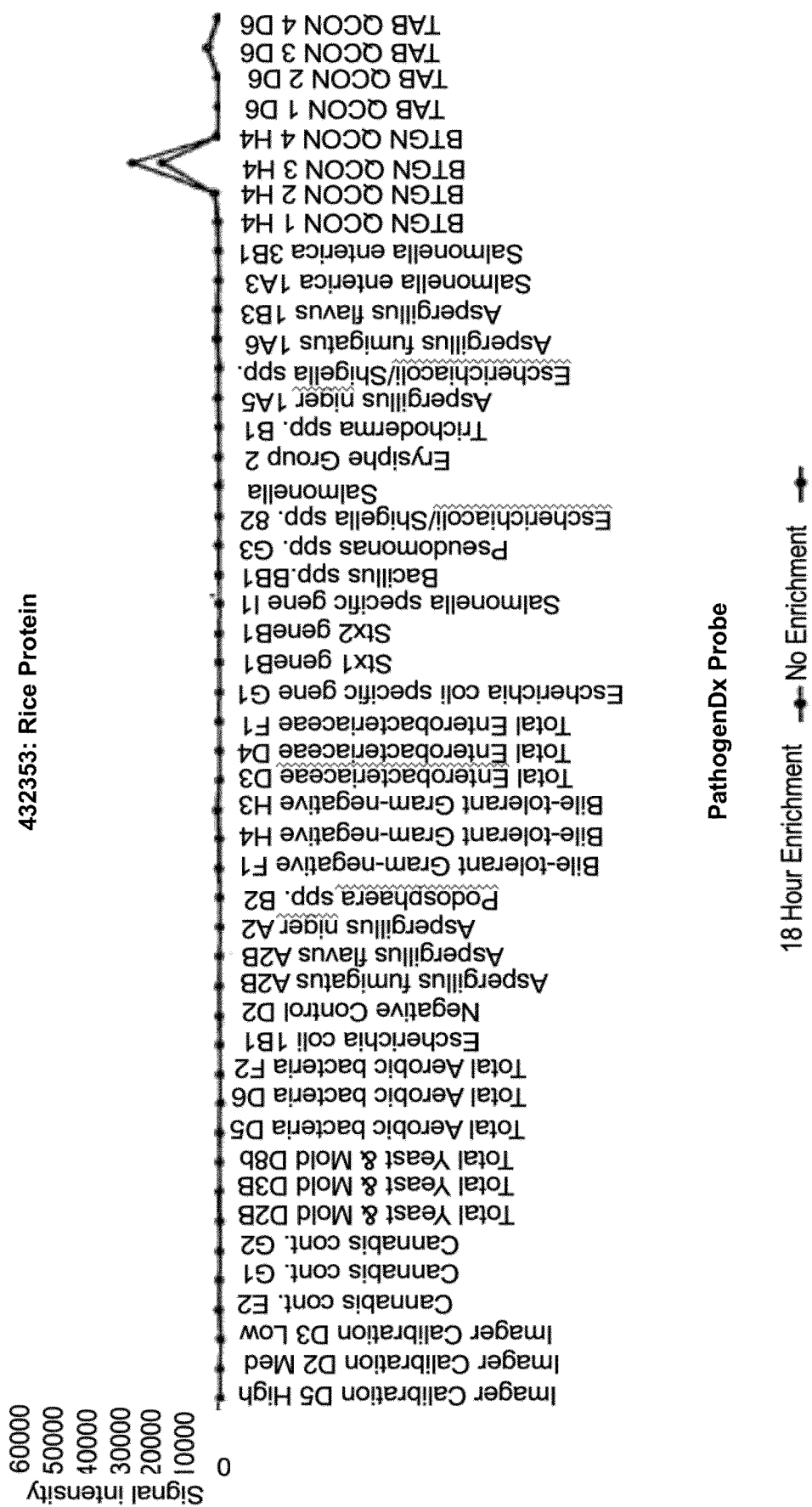
Figure 16J:
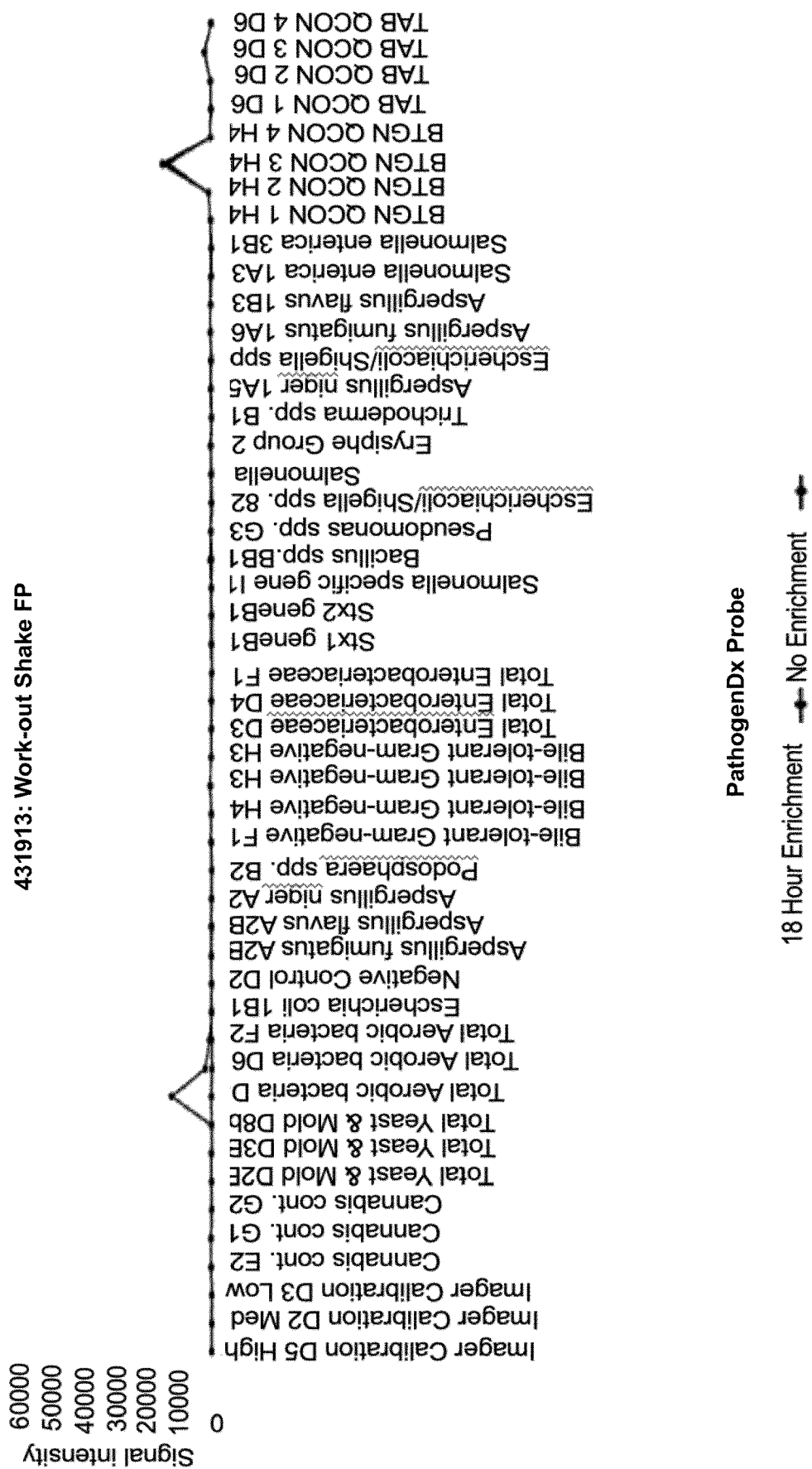
Figure 16K:
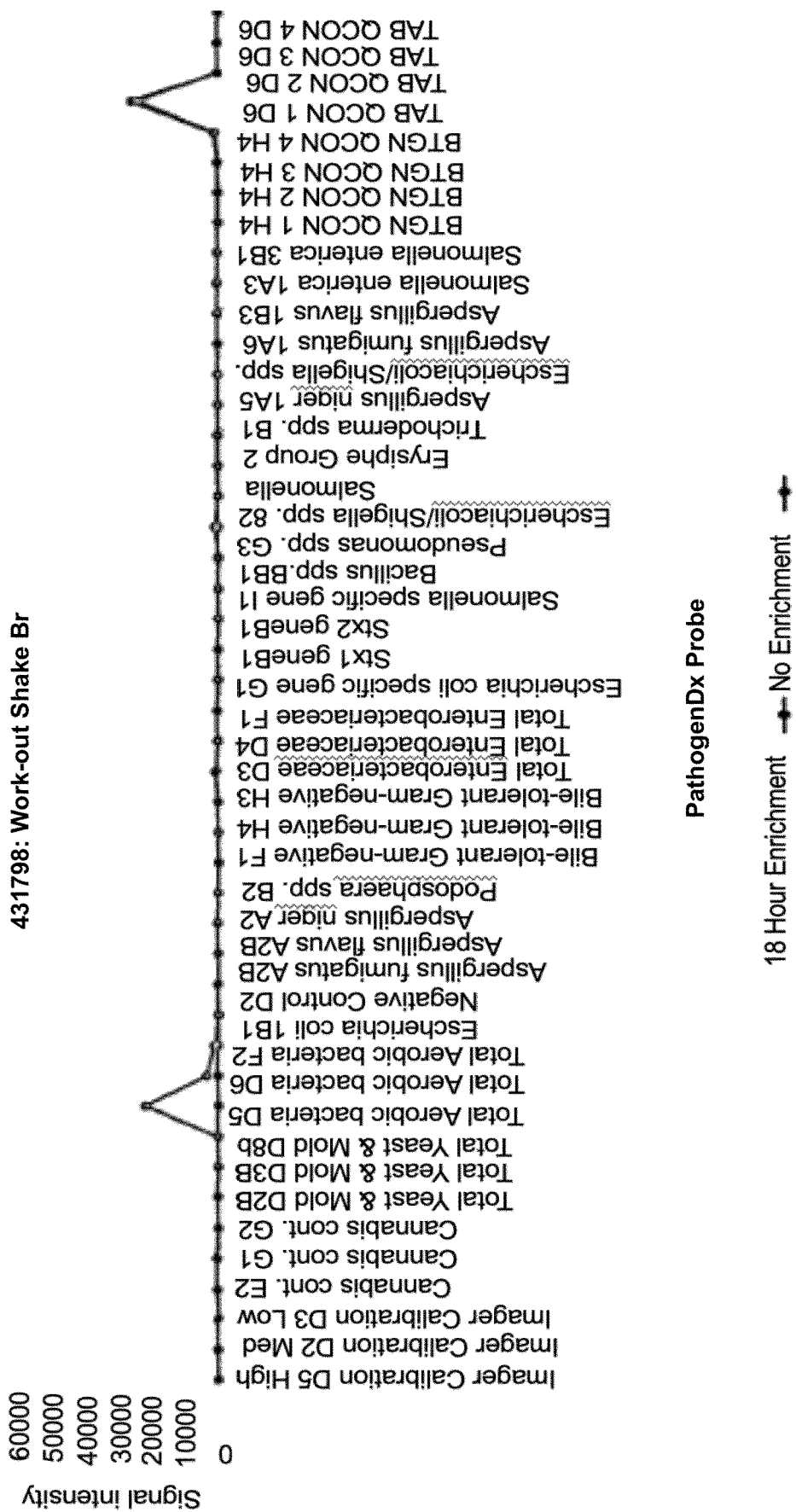
Figure 16L:
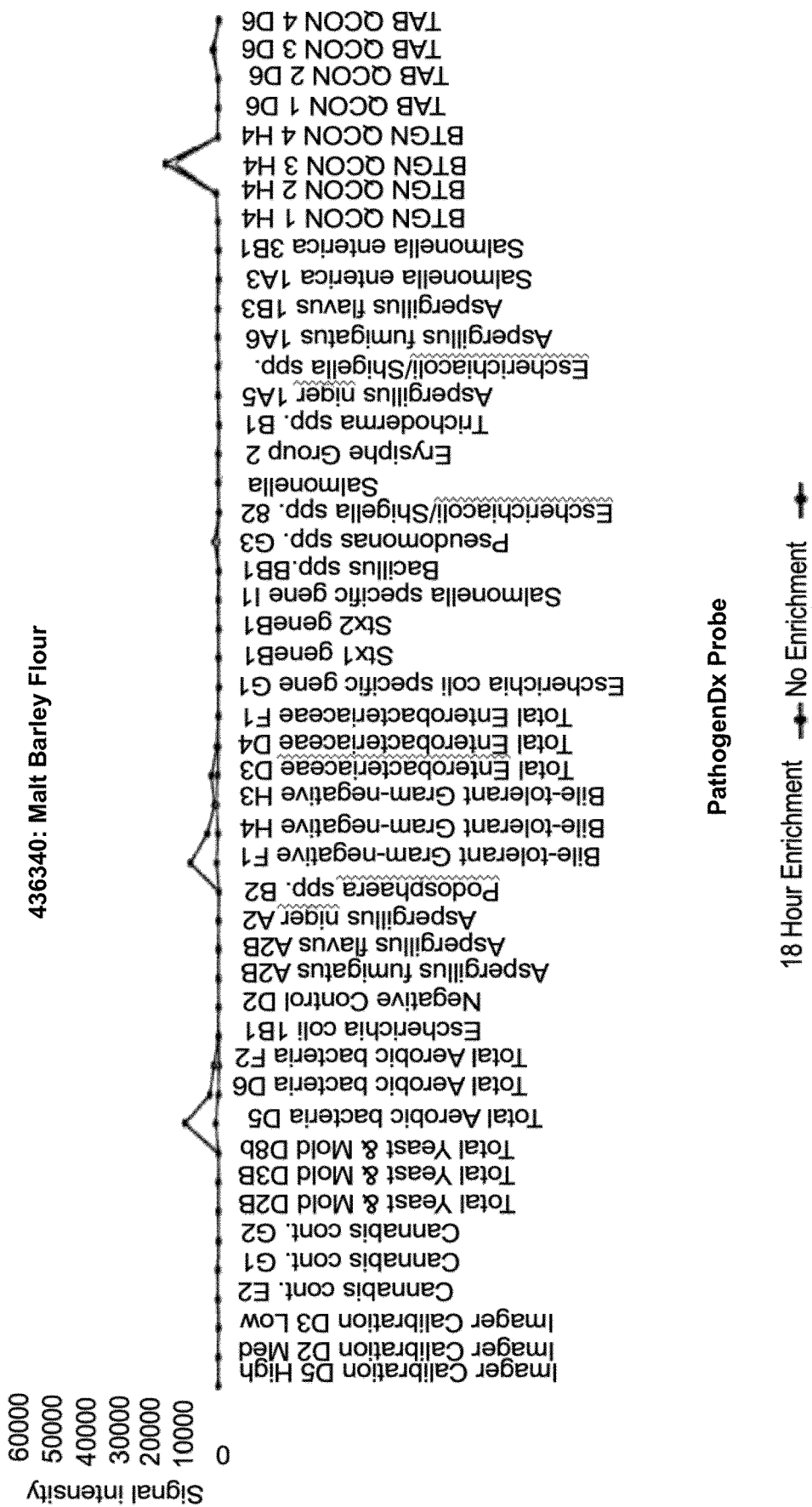
Figure 16M:
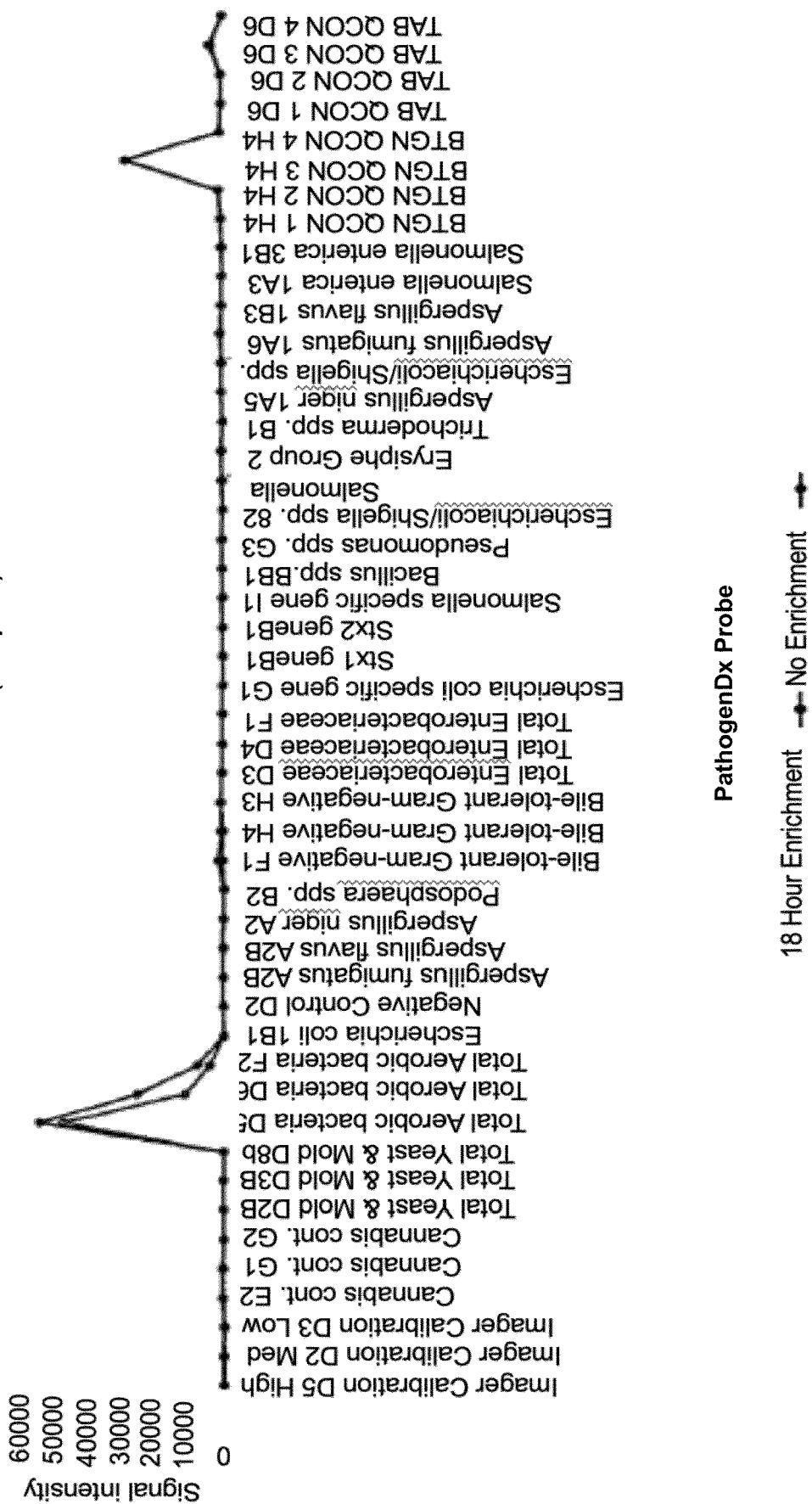
Figure 16N:
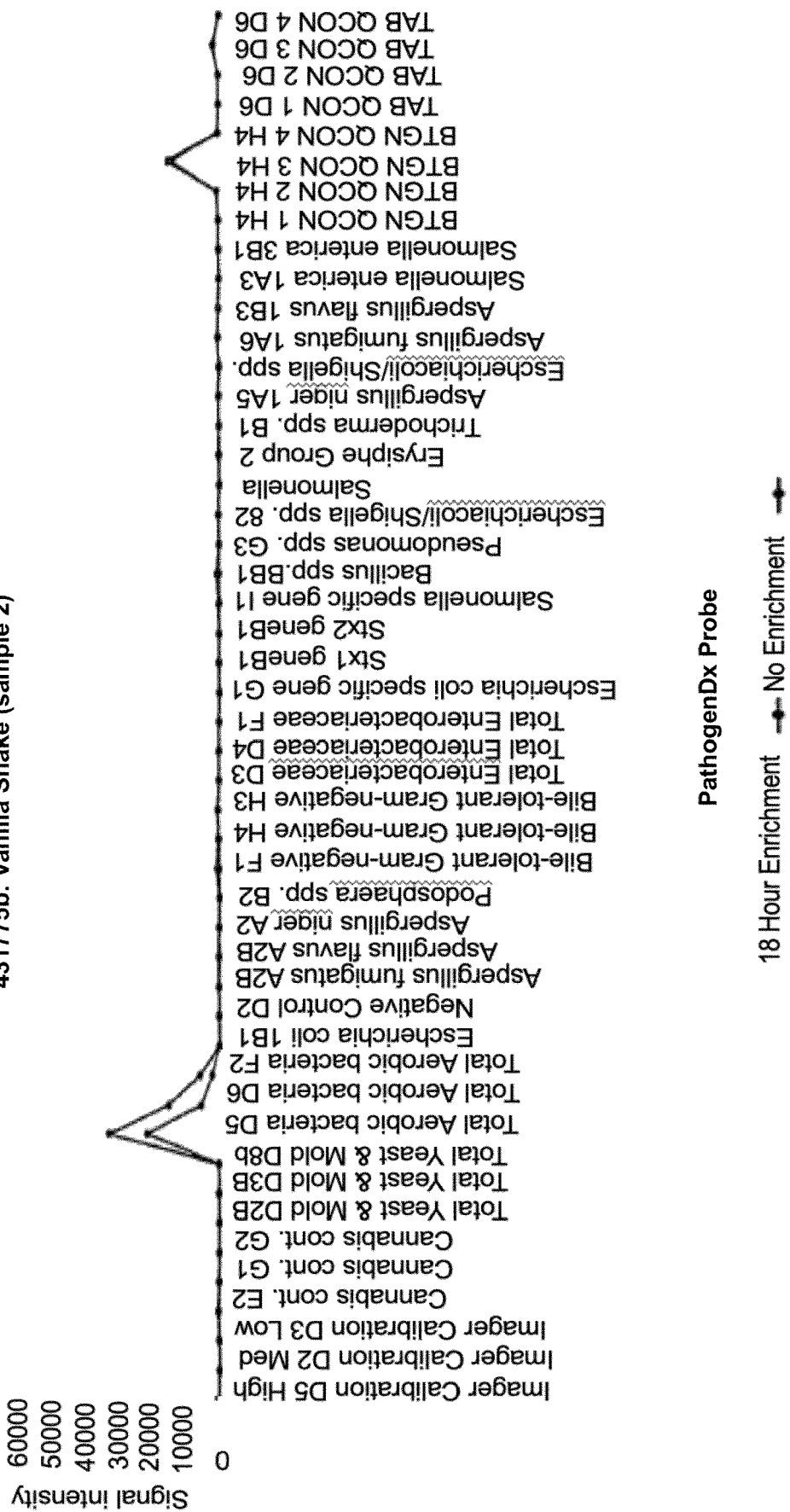
Figure 16O:
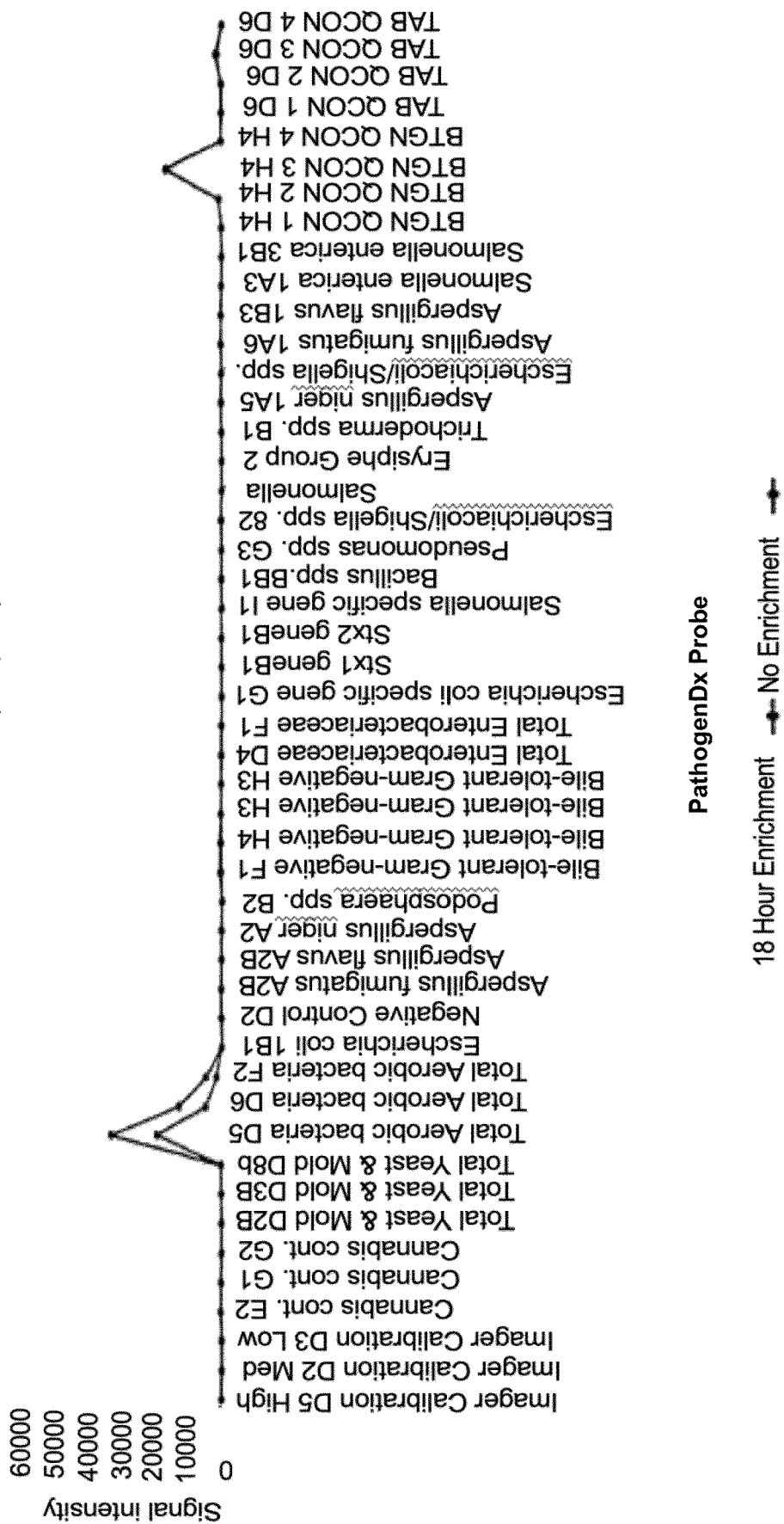
Figure 16P:
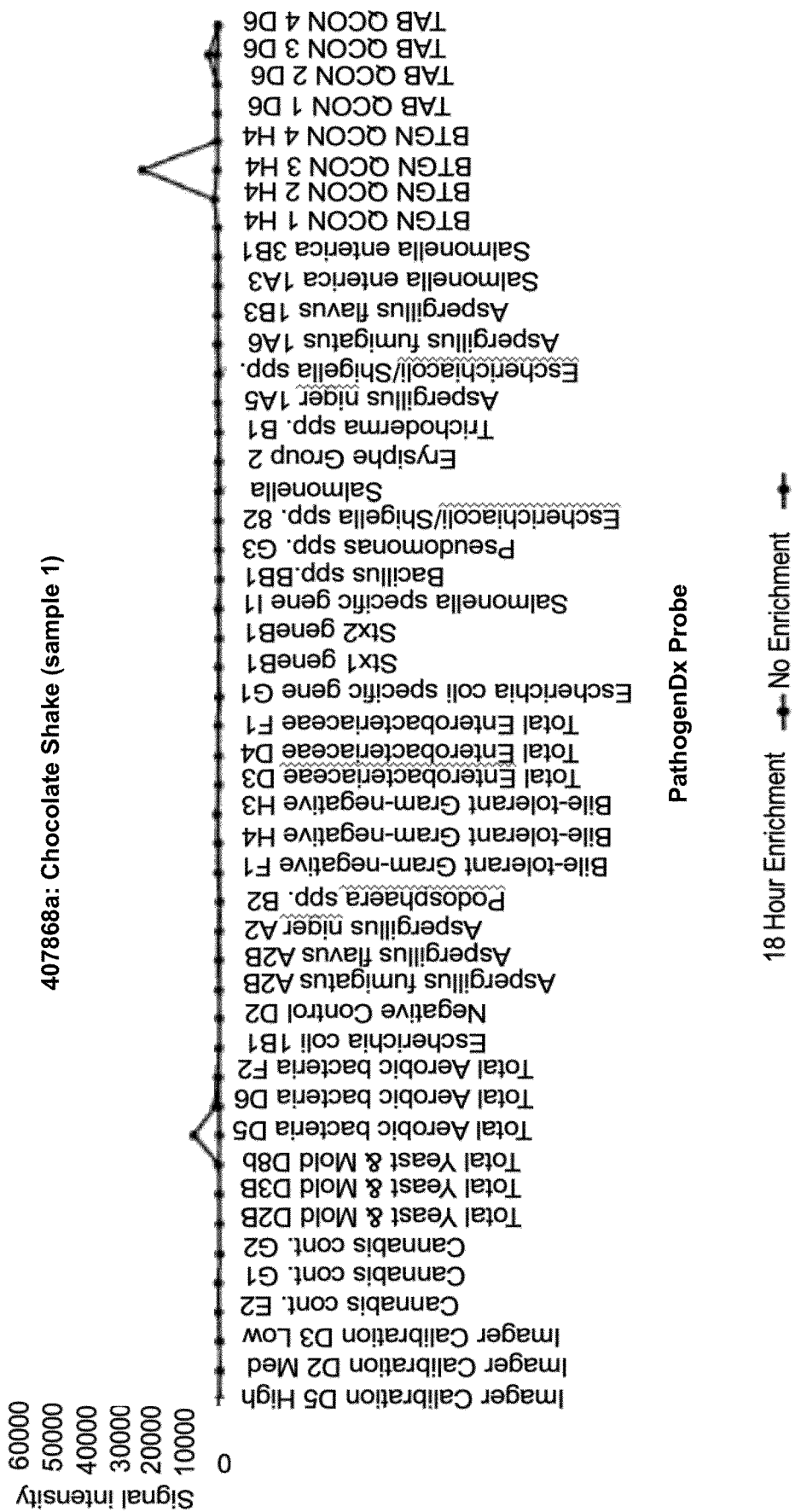
Figure 16Q:
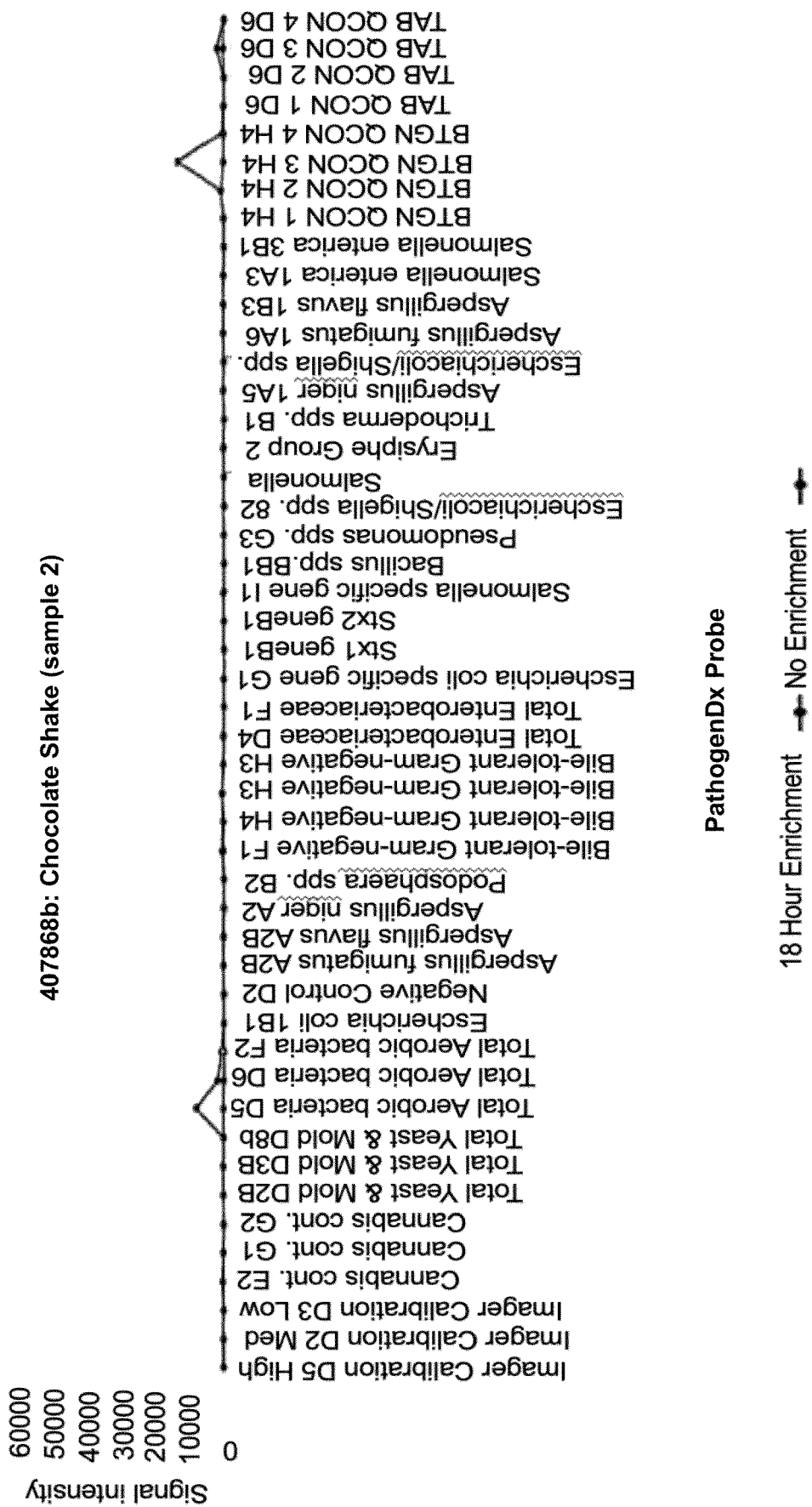
Figure 16R:
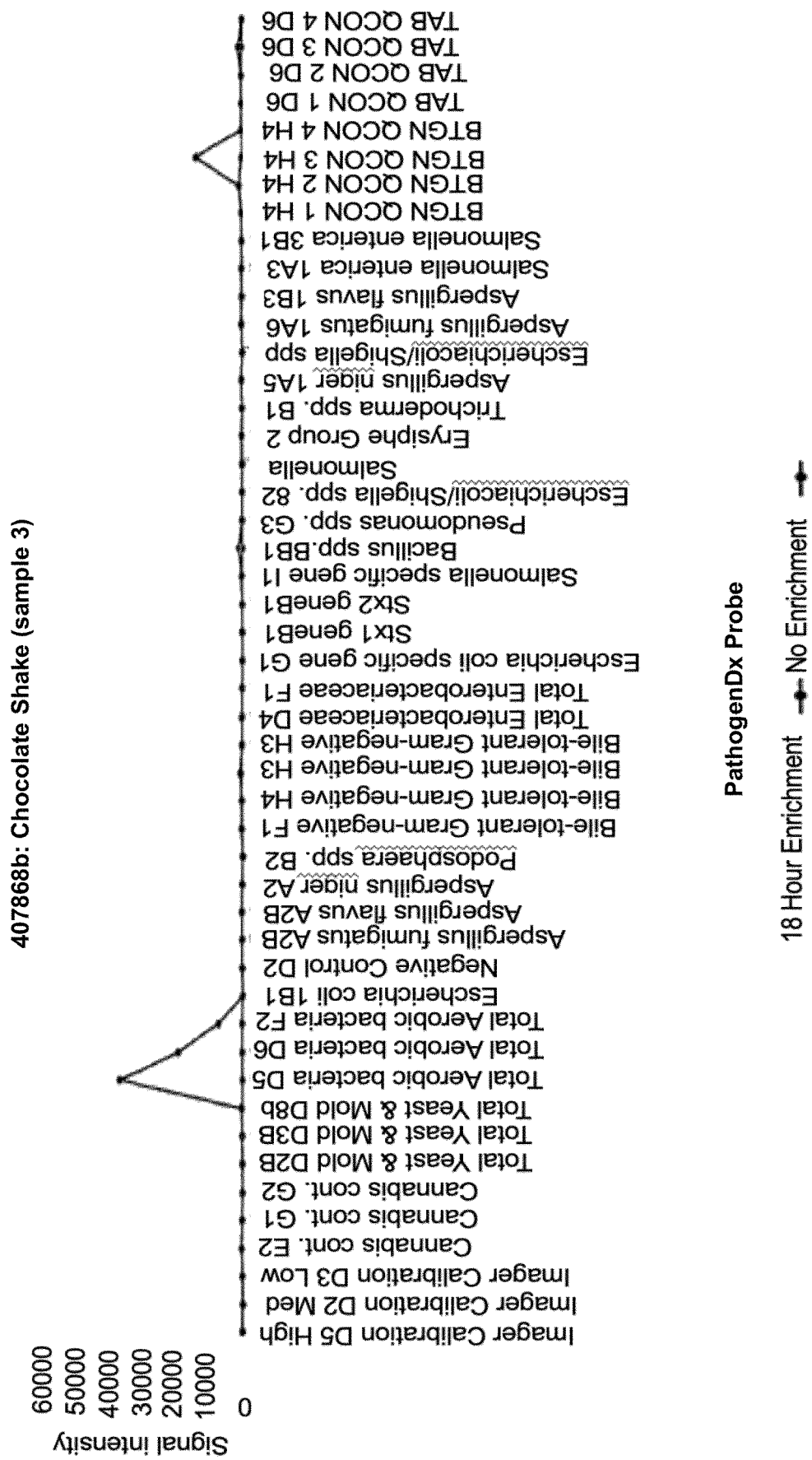
Figure 17A:
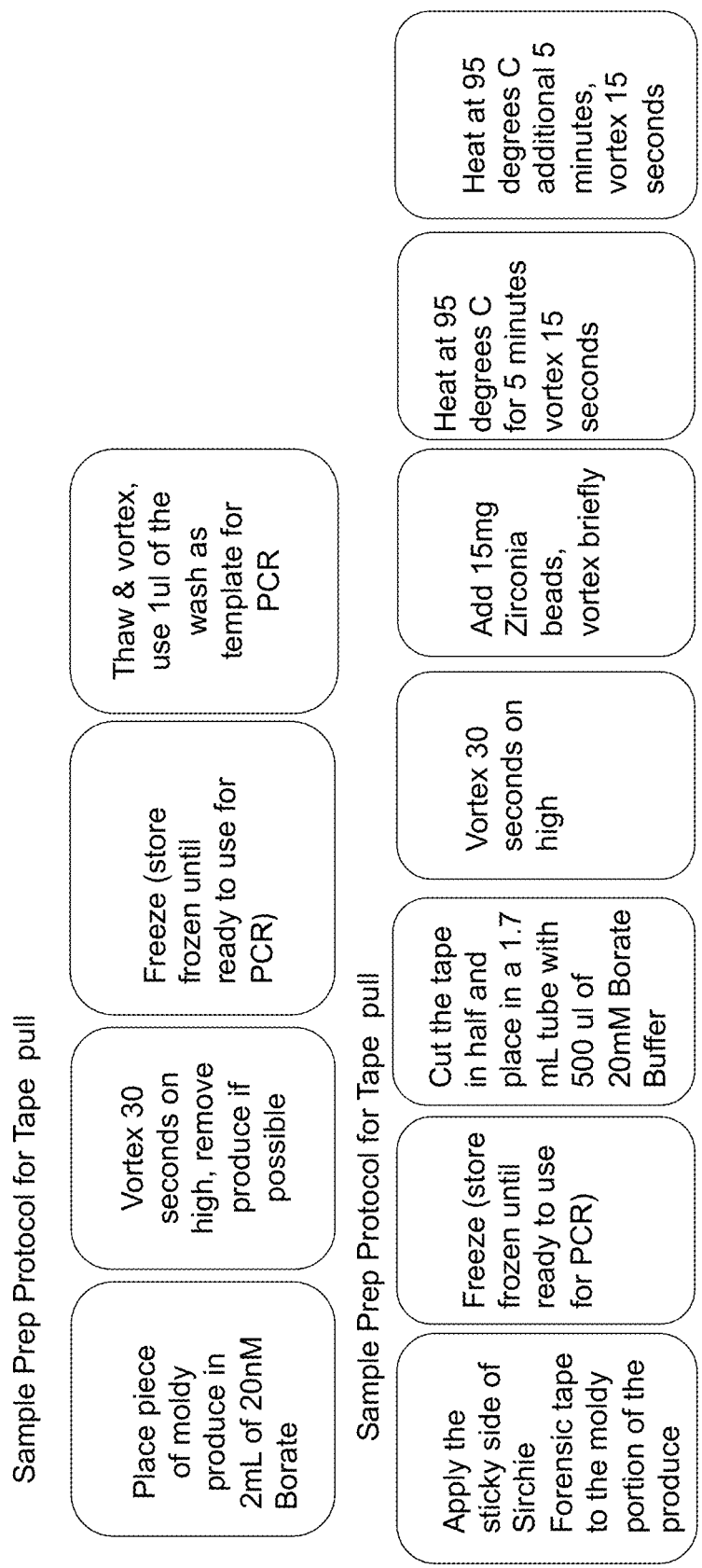
FIG. 17A shows diagrams for sample collection and preparation from two methods. Both the tape pull and wash method are used to process samples to provide a solution for microbial detection via microarray analysis.

FIGS. 16A-16R display an application of an embodiment to Processed Agricultural Products. The above teaching shows, by example, that unprocessed leaf and bud samples may be washed in an aqueous water solution, to yield a water-wash containing microbial pathogens which can then be analyzed via the present combination of RSG and microarrays. If such fresh leaf and bud materials were processed by drying, grinding or other ordinary processes, rather than analyzed when fresh, and if the microbial complement of the processed sample remained intact, then the present combination of RSG and microarray analysis would be capable of recovering and analyzing the DNA complement of those microbes in the processed material: just as it has been shown to do for fresh leaf material.

FIGS. 16A-16R display data from eighteen powdered dry food samples which were processed for analysis using the PathogenDx microarray assay system, as described above. For each sample which was already processed to be a powder, 10 g of sample was added to a Whirl-pak bag followed by 100 ml of the standard washing buffer to each bag. For those samples which were not yet a powder, they were ground with a pestle then processed. Each bag was manually stomached and then a 1 ml aliquot was removed as the "pre-enriched" sample for each food type. The bags were then placed in a 35° C. incubator for approximately 18 hours. After the enrichment, a 1 ml aliquot of the 18 hour incubation product was collected for each food type and labeled as the "enriched" sample. Both the pre-enriched and enriched aliquots were prepared for PCR amplifications followed by microarray analyses, exactly as described above. FIGS. 16A-16R comprise graphs of the raw data, for both pre-enriched and enriched samples for each of the food types are attached. There is also one graph for each of the Low, Medium, and High Total Aerobic, Bile Tolerant Gram Negative, and Total Yeast and Mold probes. Please note that the B3 marker (probes BTGN QCON3 and TABQCON3) is the positive control present at 5000 copies per reaction, which was doped into each specimen.

The data of FIGS. 16A-16R show that, for all specimens tested, the general combination of raw sample genotyping and microarray analysis, as described above, has successfully detected bacterial microbes in the processed food samples tested, with the exception of Rice Protein (FIG. 16I), which appears to be free of detectable bacterial contamination. It should be noted that in each case, the data obtained without any fluid phase enrichment, is as sensitive as that obtained with 18 hours of fluid phase enrichment at 37 C. Thus, the data of FIGS. 16A-16R show that an embodiment can detect bacterial contamination in processed foods without the need for pre-enrichment.

FIGS. 17A-17D are embodiments for the analysis of fruit, embodiments for the analysis of vegetables and embodiments for the analysis of other plant matter. The above teaching shows by example that unprocessed leaf and bud samples in *cannabis* and hops may be washed in an aqueous water solution, to yield a water-wash containing microbial pathogens which can then be analyzed via the present combination of RSG and microarrays. If fresh leaf, flower, stem or root materials from fruit and vegetables could also be washed in a water solution in that same way (when fresh or after drying and grinding or other types or processing) (FIG. 7A) so that the present combination of RSG and microarray analysis would be capable of recovering and analyzing the DNA complement of those microbes in those other materials.

At least two methods of sample collection are possible. A simple rinsing of the fruit, exactly as described for *cannabis*, above. Another method of sample collection is a "tape pull", wherein a piece of standard forensic tape is applied to the surface of the fruit, then pulled off. Upon pulling, the tape is then soaked in the standard wash buffer described above, to suspend the microbes attached to the tape. Subsequent to the tape-wash step, all other aspects of the processing and analysis (i.e. raw sample genotyping, PCR, then microarray analysis) are exactly as described above.

The data of FIG. 17B demonstrates that simple washing of the fruit and tape pull sampling of the fruit generate similar microbial data. The blueberry sample is shown to be positive for *Botrytis*, as expected, since *Botrytis* is a well-known fungal contaminant on blueberries. The lemon sample is shown to be positive for *Penicillium*, as expected, since *Penicillium* is a well-known fungal contaminant for lemons.

The data embodied in FIGS. 17C-17D, demonstrates the use of an embodiment, for the recovery and analysis of yeast microbes on the surface of fruit (blueberries and lemons in this case), but an embodiment could be extended to other fruits and vegetables for the analysis of both bacterial and fungal contamination.

FIGS. 18A-18B show embodiments for the analysis of environmental water samples/specimens. The above teaching shows by example that unprocessed leaf and bud samples in *cannabis* and hops may be washed in an aqueous water solution, to yield a water-wash containing microbial pathogens which can then be analyzed via the present combination of RSG and microarrays. If a water sample containing microbes were obtained from environmental sources (such as well water, or sea water, or soil runoff or the water from a community water supply) and then analyzed directly, or after ordinary water filtration to concentrate the microbial complement onto the surface of the filter, that the present combination of RSG and microarray analysis would be capable of recovering and analyzing the DNA complement of those microbes.

The data embodied in FIGS. 18A-18B were obtained from 5 well-water samples (named 2H, 9D, 21, 23, 25) along with 2 samples of milliQ laboratory water (obtained via reverse osmosis) referred to as "Negative Control". All samples were subjected to filtration on a sterile 0.4 um filter. Subsequent to filtration, the filters, with any microbial contamination that they may have captured, were then washed with the standard wash solution, exactly as described above for the washing of *cannabis* and fruit. Subsequent to that washing the suspended microbes in wash solution were then subjected to exactly the same combination of centrifugation (to yield a microbial pellet) then lysis and PCR of the unprocessed pellet-lysate (exactly as described above for *cannabis*), followed by PCR and microarray analysis: also as described for *cannabis*.

The data seen in FIGS. 18A-18B demonstrate that microbes collected on filtrates of environmental water samples can be analyzed via the same combination of raw sample genotyping, then PCR and microarray analysis used for *cannabis* and fruit washes. The shaded elements of the Tables in FIGS. 18A-18B demonstrate that the 5 unprocessed well-water samples all contain aerobic bacteria (upper shaded box) and bile tolerant gram negative bacteria (lower shaded box). The presence of both classes of bacteria is expected for unprocessed (raw) well water. Thus, the data of FIGS. 18A-18B demonstrate that an embodiment can be used for the analysis of environmentally derived water samples.

Embodiments for analysis of industrial washes derived from food processing. The above teaching shows by example that unprocessed leaf and bud samples in *cannabis* and hops may be washed in an aqueous water solution, to yield a water-wash containing microbial pathogens which can then be analyzed via the present combination of RSG and microarrays. The above data also show that environmentally-derived well water samples may be analyzed by an embodiment. Further, if a water sample containing microbes were obtained from industrial processing sources (such as the water effluent from the processing of fruit, vegetables, grain, meat) and then analyzed directly, or after ordinary water filtration to concentrate the microbial complement onto the surface of the filter, that the present combination of RSG and microarray analysis would be capable of recovering and analyzing the DNA complement of those microbes.

Embodiments for analysis of air filtrates. The above teaching shows by example that unprocessed leaf and bud samples in *cannabis* and hops may be washed in an aqueous water solution, to yield a water wash containing microbial pathogens which can then be analyzed via the present combination of RSG and microarrays. Further, if an air sample containing microbes as an aerosol or adsorbed to airborne dust were obtained by air filtration onto an ordinary air-filter (such as used in the filtration of air in an agricultural or food processing plant, or on factory floor, or in a public building or a private home) that such air-filters could then be washed with a water solution, as has been demonstrated for plant matter, to yield a microbe-containing filter eluate, such that the present combination of RSG and microarray analysis would be capable of recovering and analyzing the DNA complement of those microbes.

While the foregoing written description of an embodiments enables one of ordinary skill to make and use what is considered presently to be the best mode thereof, those of ordinary skill will understand and appreciate the existence of variations, combinations, and equivalents of the specific embodiment, method, and examples herein. The present disclosure should therefore not be limited by the above described embodiments, methods, and examples, but by all embodiments and methods within the scope and spirit of the present disclosure.

What is claimed is:

1. A method for identifying at least one bacteria in a sample, consisting of:
obtaining the sample as a raw, unpurified sample;
amplifying, in a first PCR reaction DNA in the raw, unpurified sample using primer pairs selective for at least one bacterial DNA to generate a first amplified product;
amplifying, in a second PCR reaction, the first amplified product using fluorescent labeled primer pairs to generate a fluorescent labeled second amplified product; wherein said primer pairs for the first PCR reaction and the second PCR reaction are at least two nucleotide sequence pairs selected from the group consisting of SEQ ID NOS: 1 and 2, SEQ ID NOS: 3 and 4, SEQ ID NOS: 5 and 6, SEQ ID NOS: 7 and 8, SEQ ID NOS: 9 and 10, SEQ ID NOS: 11 and 12, SEQ ID NOS: 13 and 14, SEQ ID NOS: 15 and 16, SEQ ID NOS: 17 and 18, SEQ ID NOS: 19 and 20, SEQ ID NOS: 29 and 30, SEQ ID NOS: 31 and 32, SEQ ID NOS: 117 and 118, and SEQ ID NOS: 119 and 120;
applying the fluorescent labeled second amplified product directly to a microarray containing hybridization probes affixed thereto that are complementary to selected microbial DNA sequences; wherein said hybridization probes consist of the nucleotide sequences of SEQ ID NOS: 37-79;
hybridizing the fluorescent second amplified product to the hybridization probes at room temperature and washing the microarray;
analyzing optically hybridization of the fluorescent second amplified product to the hybridization probes to produce microarray binding data; and
analyzing the microarray binding data to identify the at least one bacteria in the sample.

2. The method of claim 1, wherein the sample is an environmental water sample, an industrial water sample or an air sample.

3. The method of claim 2, wherein the sample is obtained from water-rinsing plant materials during an industrial process.

4. The method of claim 2, wherein the sample is obtained from water-rinsing animal materials during an industrial process.

5. The method of claim 2, wherein the sample is obtained from water-rinsing an air filter.

6. The method of claim 1, wherein the bacteria is from soil, from air, from water, from a soil-less growth media, or from a hydroponic growth media.

7. A method for identifying at least one fungus in a sample, consisting of:
obtaining the sample as a raw, unpurified sample;
amplifying, in a first PCR reaction DNA in the raw, unpurified sample using primer pairs selective for at least one fungal DNA to generate a first amplified product;
amplifying, in a second PCR reaction, the first amplified product using fluorescent labeled primer pairs to generate a fluorescent labeled second amplified product; wherein said primer pairs for the first PCR reaction and the second PCR reaction comprising at least two nucleotide sequence pairs selected from the group consisting of SEQ ID NOS: 21 and 22, SEQ ID NOS: 23 and 24, SEQ ID NOS: 33 and 34, and SEQ ID NOS: 35 and 36;

applying the fluorescent labeled second amplified product directly to a microarray containing hybridization probes affixed thereto that are complementary to selected microbial DNA sequences; wherein said hybridization probes consist of the nucleotide sequences of SEQ ID NOS: 80-116;

hybridizing the fluorescent second amplified product to the hybridization probes at room temperature and washing the microarray;

analyzing optically hybridization of the fluorescent second amplified product to the hybridization probes to produce microarray binding data; and analyzing the microarray binding data to identify the at least one fungus in the sample.

8. The method of claim 7, wherein the sample is an environmental water sample, an industrial water sample or an air sample.

9. The method of claim 8, wherein the sample is obtained from water-rinsing plant materials during an industrial process.

10. The method of claim 8, wherein the sample is obtained from water-rinsing animal materials during an industrial process.

11. The method of claim 8, wherein the sample is obtained from water-rinsing an air filter.

12. The method of claim 7, wherein the fungus is from soil, from air, from water, from a soil-less growth media, or from a hydroponic growth media.

\* \* \* \* \*

SEQUENCE LISTING

<160> NUMBER OF SEQ ID NOS: 121

<210> SEQ ID NO 1
<211> LENGTH: 23
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 1
tttcacaytg gractgagac acg                                             23

<210> SEQ ID NO 2
<211> LENGTH: 27
<212> TYPE: DNA
<213> ORGANISM: Artificial Sequence
<220> FEATURE:
<223> OTHER INFORMATION: Reverse primer for amplification of the 16S
      rDNA HV3 locus in all bacteria

<400> SEQUENCE: 2
tttgactacc agggtatcta atcctgt                                         27

<210> SEQ ID NO 3
<211> LENGTH: 24
<212> TYPE: DNA
<213> ORGANISM: Artificial Sequence
<220> FEATURE:
<223> OTHER INFORMATION: Forward primer for amplification of the 16S
      rDNA HV3 locus in all bacteria

<400> SEQUENCE: 3
tttactgaga cacggyccar actc                                              24

<210> SEQ ID NO 4
<211> LENGTH: 24
<212> TYPE: DNA
<213> ORGANISM: Artificial Sequence
<220> FEATURE:
<223> OTHER INFORMATION: Reverse primer for amplification of the 16S
      rDNA HV3 Locus in all bacteria

<400> SEQUENCE: 4
tttgtattac cgcggctgct ggca                                              24

<210> SEQ ID NO 5
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 5
tttataatct acggcttatt gttgaacg                                          28

<210> SEQ ID NO 6
<211> LENGTH: 29
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 6
tttggtatag ctactgtcac cagacaatg                                         29

<210> SEQ ID NO 7
<211> LENGTH: 28
<212> TYPE: DNA
<213> ORGANISM: Artificial Sequence
<220> FEATURE:
<223> OTHER INFORMATION: Forward primer for amplification of the Stx1
      locus in pathogenic Escherichia coli

<400> SEQUENCE: 7
tttatgtgac aggatttgtt aacaggac                                          28

<210> SEQ ID NO 8
<211> LENGTH: 28
<212> TYPE: DNA
<213> ORGANISM: Artificial Sequence
<220> FEATURE:
<223> OTHER INFORMATION: Reverse primer for amplification of the Stx1
      locus in pathogenic Escherichia coli

<400> SEQUENCE: 8
tttctgtcac cagacaatgt aaccgctg                                          28

<210> SEQ ID NO 9
<211> LENGTH: 26
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 9
tttgatgcat ccagagcagt tctgcg                                    26

<210> SEQ ID NO 10
<211> LENGTH: 27
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 10
tttgtgaggt ccacgtctcc cggcgtc                                   27

<210> SEQ ID NO 11
<211> LENGTH: 23
<212> TYPE: DNA
<213> ORGANISM: Artificial Sequence
<220> FEATURE:
<223> OTHER INFORMATION: Forward primer for amplification of the Stx2
      locus in pathogenic Escherichia coli

<400> SEQUENCE: 11
ttttgtcact gtcacagcag aag                                       23

<210> SEQ ID NO 12
<211> LENGTH: 25
<212> TYPE: DNA
<213> ORGANISM: Artificial Sequence
<220> FEATURE:
<223> OTHER INFORMATION: Reverse primer for amplification of the Stx2
      locus in pathogenic Escherichia coli

<400> SEQUENCE: 12
tttgcgtcat cgtatacaca ggagc                                     25

<210> SEQ ID NO 13
<211> LENGTH: 28
<212> TYPE: DNA
<213> ORGANISM: Artificial Sequence
<220> FEATURE:
<223> OTHER INFORMATION: Forward primer for amplification of the InvA
      locus in all Salmonella

<400> SEQUENCE: 13
tttattatcg ccacgttcgg gcaattcg                                  28

<210> SEQ ID NO 14
<211> LENGTH: 28
<212> TYPE: DNA
<213> ORGANISM: Artificial Sequence
<220> FEATURE:
<223> OTHER INFORMATION: Reverse primer for amplification of the InvA
      locus in all Salmonella

<400> SEQUENCE: 14
tttcttcatc gcaccgtcaa aggaaccg                                  28

```
<210> SEQ ID NO 15
<211> LENGTH: 26
<212> TYPE: DNA
<213> ORGANISM: Artificial Sequence
<220> FEATURE:
<223> OTHER INFORMATION: Forward primer for amplification of the InvA
      locus in all Salmonella us

<400> SEQUENCE: 15
ttttatcgtt attaccaaag gttcag                                        26

<210> SEQ ID NO 16
<211> LENGTH: 28
<212> TYPE: DNA
<213> ORGANISM: Artificial Sequence
<220> FEATURE:
<223> OTHER INFORMATION: Reverse primer for amplification of the InvA
      locus in all Salmonella

<400> SEQUENCE: 16
tttcctttcc agtacgcttc gccgttcg                                      28

<210> SEQ ID NO 17
<211> LENGTH: 26
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 17
tttcagagtg ggaagcgaaa atcctg                                        26

<210> SEQ ID NO 18
<211> LENGTH: 26
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 18
tttacgccag tacaggtaga cttctg                                        26

<210> SEQ ID NO 19
<211> LENGTH: 25
<212> TYPE: DNA
<213> ORGANISM: Artificial Sequence
<220> FEATURE:
<223> OTHER INFORMATION: Forward primer for amplification of the tuf
      locus in all Escherichia coli

<400> SEQUENCE: 19
tttgttgtta ccggtcgtgt agaac                                         25

<210> SEQ ID NO 20
<211> LENGTH: 28
<212> TYPE: DNA
<213> ORGANISM: Artificial Sequence
<220> FEATURE:
<223> OTHER INFORMATION: Reverse primer for amplification of the tuf
      locus in all Escherichia coli

<400> SEQUENCE: 20
tttcttctga gtctctttga taccaacg                                      28

<210> SEQ ID NO 21
```

```
<211> LENGTH: 26
<212> TYPE: DNA
<213> ORGANISM: Artificial Sequence
<220> FEATURE:
<223> OTHER INFORMATION: Forward primer for amplification of the ITS2
      locus in all yeast and mold/fungi

<400> SEQUENCE: 21
tttactttya acaayggatc tcttgg                                          26

<210> SEQ ID NO 22
<211> LENGTH: 26
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 22
tttcttttcc tccgcttatt gatatg                                          26

<210> SEQ ID NO 23
<211> LENGTH: 23
<212> TYPE: DNA
<213> ORGANISM: Artificial Sequence
<220> FEATURE:
<223> OTHER INFORMATION: Forward primer for amplification of the ITS2
      locus in all yeast and mold/fungi

<400> SEQUENCE: 23
tttgcatcga tgaagarcgy agc                                             23

<210> SEQ ID NO 24
<211> LENGTH: 22
<212> TYPE: DNA
<213> ORGANISM: Artificial Sequence
<220> FEATURE:
<223> OTHER INFORMATION: Reverse primer for amplification of the ITS2
      locus in all yeast and mold/fungi

<400> SEQUENCE: 24
tttcctccgc ttattgatat gc                                              22

<210> SEQ ID NO 25
<211> LENGTH: 25
<212> TYPE: DNA
<213> ORGANISM: Artificial Sequence
<220> FEATURE:
<223> OTHER INFORMATION: Forward primer for amplification of the ITS1
      locus in Cannabis/plant

<400> SEQUENCE: 25
tttgcaacag cagaacgacc cgtga                                           25

<210> SEQ ID NO 26
<211> LENGTH: 25
<212> TYPE: DNA
<213> ORGANISM: Artificial Sequence
<220> FEATURE:
<223> OTHER INFORMATION: Reverse primer for amplification of the ITS1
      locus in Cannabis/plant

<400> SEQUENCE: 26
tttcgataaa cacgcatctc gattg                                           25

<210> SEQ ID NO 27
<211> LENGTH: 27
```

```
<212> TYPE: DNA
<213> ORGANISM: Artificial Sequence
<220> FEATURE:
<223> OTHER INFORMATION: Forward primer for amplification of the ITS1
      locus in Cannabis/plant

<400> SEQUENCE: 27
tttcgtgaac acgttttaaa cagcttg                                            27

<210> SEQ ID NO 28
<211> LENGTH: 24
<212> TYPE: DNA
<213> ORGANISM: Artificial Sequence
<220> FEATURE:
<223> OTHER INFORMATION: Reverse primer for amplification of the ITS1
      locus in Cannabis/plant

<400> SEQUENCE: 28
tttccaccgc acgagccacg cgat                                               24

<210> SEQ ID NO 29
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 29
ttaccttcgg gcctcttgcc atcrgatgtg                                         30

<210> SEQ ID NO 30
<211> LENGTH: 33
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 30
ttggaattct acccccctct acragactca agc                                     33

<210> SEQ ID NO 31
<211> LENGTH: 30
<212> TYPE: DNA
<213> ORGANISM: Artificial Sequence
<220> FEATURE:
<223> OTHER INFORMATION: Forward primer for amplification of the 16S
      rDNA HV3 locus in Enterobacteriaceae

<400> SEQUENCE: 31
ttatattgca caatgggcgc aagcctgatg                                         30

<210> SEQ ID NO 32
<211> LENGTH: 25
<212> TYPE: DNA
<213> ORGANISM: Artificial Sequence
<220> FEATURE:
<223> OTHER INFORMATION: Reverse primer for amplification of the 16S
      rDNA HV3 locus in Enterobacteriaceae

<400> SEQUENCE: 32
ttttgtatta ccgcggctgc tggca                                              25

<210> SEQ ID NO 33
<211> LENGTH: 28
<212> TYPE: DNA
```

```
<213> ORGANISM: Artificial Sequence
<220> FEATURE:
<223> OTHER INFORMATION: Forward primer for amplification of the ITS2
      locus in Aspergillus spp

<400> SEQUENCE: 33
tttaaaggca gcggcggcac cgcgtccg                                        28

<210> SEQ ID NO 34
<211> LENGTH: 27
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 34
ttttcttttc ctccgcttat tgatatg                                         27

<210> SEQ ID NO 35
<211> LENGTH: 26
<212> TYPE: DNA
<213> ORGANISM: Artificial Sequence
<220> FEATURE:
<223> OTHER INFORMATION: Forward primer for amplification of the ITS2
      locus in Aspergillus spp

<400> SEQUENCE: 35
tttcctcgag cgtatggggc tttgtc                                          26

<210> SEQ ID NO 36
<211> LENGTH: 24
<212> TYPE: DNA
<213> ORGANISM: Artificial Sequence
<220> FEATURE:
<223> OTHER INFORMATION: Reverse primer for amplification of the ITS2
      locus in Aspergillus spp

<400> SEQUENCE: 36
tttttcctcc gcttattgat atgc                                            24

<210> SEQ ID NO 37
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 37
tttttttgtt gtggttaata accgattttt                                      30

<210> SEQ ID NO 38
<211> LENGTH: 30
<212> TYPE: DNA
<213> ORGANISM: Artificial Sequence
<220> FEATURE:
<223> OTHER INFORMATION: Probe sequence for the 16S locus in Salmonella
      enterica

<400> SEQUENCE: 38 ttttttaac cgcagcaatt gactcttttt                                       30

<210> SEQ ID NO 39
<211> LENGTH: 30
<212> TYPE: DNA
<213> ORGANISM: Artificial Sequence
```

```
<220> FEATURE:
<223> OTHER INFORMATION: Probe sequence for the 16S locus in Salmonella
      enterica

<400> SEQUENCE: 39 tttttctgt taataaccgc agctttttt                                          30

<210> SEQ ID NO 40
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli/Shigella

<400> SEQUENCE: 40
ttttctaata cctttgctca ttgactcttt                                        30

<210> SEQ ID NO 41
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli/Shigella

<400> SEQUENCE: 41 tttttaagg gagtaaagtt aatatttttt                                         30

<210> SEQ ID NO 42
<211> LENGTH: 30
<212> TYPE: DNA
<213> ORGANISM: Artificial Sequence
<220> FEATURE:
<223> OTHER INFORMATION: Probe sequence for the 16S locus in Escherichia
      coli/Shigella

<400> SEQUENCE: 42
ttttctcctt tgctcattga cgttattttt                                        30

<210> SEQ ID NO 43
<211> LENGTH: 29
<212> TYPE: DNA
<213> ORGANISM: Artificial Sequence
<220> FEATURE:
<223> OTHER INFORMATION: Probe sequence for the 16S locus in Pseudomonas
      spp.

<400> SEQUENCE: 43
tttttgttac cracagaata agcatttttt                                        29

<210> SEQ ID NO 44
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      spp.

<400> SEQUENCE: 44 tttttaagc actttaagtt gggattttt                                          30

<210> SEQ ID NO 45
<211> LENGTH: 30
<212> TYPE: DNA
<213> ORGANISM: Artificial Sequence
<220> FEATURE:
```

<223> OTHER INFORMATION: Probe sequence for the 16S locus in Salmonella
      bongori

<400> SEQUENCE: 45
tttttttaat aaccttgttg attgttttttt                                    30

<210> SEQ ID NO 46
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      aeruginosa

<400> SEQUENCE: 46
tttttgcagt aagttaatac cttgtctttt                                     30

<210> SEQ ID NO 47
<211> LENGTH: 30
<212> TYPE: DNA
<213> ORGANISM: Artificial Sequence
<220> FEATURE:
<223> OTHER INFORMATION: Probe sequence for the 16S locus in Pseudomonas
      cannabina

<400> SEQUENCE: 47
tttttttacg tatctgtttt gactcttttt                                     30

<210> SEQ ID NO 48
<211> LENGTH: 30
<212> TYPE: DNA
<213> ORGANISM: Artificial Sequence
<220> FEATURE:
<223> OTHER INFORMATION: Probe sequence for the 16S locus in Xanthamonas
      spp.

<400> SEQUENCE: 48 tttttttgtta atacccgatt gttctttttt                                    30

<210> SEQ ID NO 49
<211> LENGTH: 30
<212> TYPE: DNA
<213> ORGANISM: Artificial Sequence
<220> FEATURE:
<223> OTHER INFORMATION: Probe sequence for the 16S locus in Listeria
      spp.

<400> SEQUENCE: 49
ttttctaagt actgttgtta gagaatttttt                                    30

<210> SEQ ID NO 50
<211> LENGTH: 30
<212> TYPE: DNA
<213> ORGANISM: Artificial Sequence
<220> FEATURE:
<223> OTHER INFORMATION: Probe sequence for the 16S locus in
      Campylobacter spp.

<400> SEQUENCE: 50 tttttttatga cacttttcgg agctcttttt                                    30

<210> SEQ ID NO 51
<211> LENGTH: 30
<212> TYPE: DNA
<213> ORGANISM: Artificial Sequence
<220> FEATURE:
<223> OTHER INFORMATION: Probe sequence for the 16S locus in Aeromonas -continued salmonicida/hydrophilia

<400> SEQUENCE: 51
tttttgccta atacgtrtca actgcttttt                                              30

<210> SEQ ID NO 52
<211> LENGTH: 30
<212> TYPE: DNA
<213> ORGANISM: Artificial Sequence
<220> FEATURE:
<223> OTHER INFORMATION: Probe sequence for the 16S locus in Aeromonas
      spp.

<400> SEQUENCE: 52
ttattttctg tgacgttact cgcttttatt                                              30

<210> SEQ ID NO 53
<211> LENGTH: 30
<212> TYPE: DNA
<213> ORGANISM: Artificial Sequence
<220> FEATURE:
<223> OTHER INFORMATION: Probe sequence for the 16S locus in Vibrio spp.

<400> SEQUENCE: 53 tttttgaag gtggttaagc taattttttt                                               30

<210> SEQ ID NO 54
<211> LENGTH: 30
<212> TYPE: DNA
<213> ORGANISM: Artificial Sequence
<220> FEATURE:
<223> OTHER INFORMATION: Probe sequence for the 16S locus in
      Staphylococcus aureus

<400> SEQUENCE: 54 tttttcata tgtgtaagta actgttttt                                                30

<210> SEQ ID NO 55
<211> LENGTH: 30
<212> TYPE: DNA
<213> ORGANISM: Artificial Sequence
<220> FEATURE:
<223> OTHER INFORMATION: Probe sequence for the 16S locus in Bacillus
      spp. Group 1

<400> SEQUENCE: 55
tttttcagtt gaataagctg gcactctttt                                              30

<210> SEQ ID NO 56
<211> LENGTH: 30
<212> TYPE: DNA
<213> ORGANISM: Artificial Sequence
<220> FEATURE:
<223> OTHER INFORMATION: Probe sequence for the 16S locus in Bacillus
      spp. Group 2

<400> SEQUENCE: 56 tttttcaag taccgttcga atagttttt                                                30

<210> SEQ ID NO 57
<211> LENGTH: 30
<212> TYPE: DNA
<213> ORGANISM: Artificial Sequence
<220> FEATURE:
<223> OTHER INFORMATION: Probe sequence for the 16S locus in
      Alkanindiges spp.

<400> SEQUENCE: 57
tttttaggct actgrtacta atatctttt                                30

<210> SEQ ID NO 58
<211> LENGTH: 30
<212> TYPE: DNA
<213> ORGANISM: Artificial Sequence
<220> FEATURE:
<223> OTHER INFORMATION: Probe sequence for the 16S locus in Citrobacter
      spp. Gtoup 1

<400> SEQUENCE: 58 tttttttcctt agccattgac gttattttt                                30

<210> SEQ ID NO 59
<211> LENGTH: 30
<212> TYPE: DNA
<213> ORGANISM: Artificial Sequence
<220> FEATURE:
<223> OTHER INFORMATION: Probe sequence for the 16S locus in Clostridium
      spp.

<400> SEQUENCE: 59
ttttctggam gataatgacg gtacagtttt                                30

<210> SEQ ID NO 60
<211> LENGTH: 30
<212> TYPE: DNA
<213> ORGANISM: Artificial Sequence
<220> FEATURE:
<223> OTHER INFORMATION: Probe sequence for the 16S locus in Ysernia
      pestis

<400> SEQUENCE: 60
tttttttgag tttaatacgc tcaacttttt                                30

<210> SEQ ID NO 61
<211> LENGTH: 30
<212> TYPE: DNA
<213> ORGANISM: Artificial Sequence
<220> FEATURE:
<223> OTHER INFORMATION: Probe sequence for the 16S locus in Panteoa
      agglomerans

<400> SEQUENCE: 61 tttttaacc ctgtcgattg acgccttttt                                 30

<210> SEQ ID NO 62
<211> LENGTH: 30
<212> TYPE: DNA
<213> ORGANISM: Artificial Sequence
<220> FEATURE:
<223> OTHER INFORMATION: Probe sequence for the 16S locus in Panteoa
      stewartii

<400> SEQUENCE: 62 tttttaacc tcatcaattg acgccttttt                                 30

<210> SEQ ID NO 63
<211> LENGTH: 30
<212> TYPE: DNA
<213> ORGANISM: Artificial Sequence
<220> FEATURE:
<223> OTHER INFORMATION: Probe sequence for the 16S locus in Hafnia spp.

<400> SEQUENCE: 63 tttttctaa ccgcagtgat tgatctttt        30

<210> SEQ ID NO 64
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      pneumoniae

<400> SEQUENCE: 64 tttttctaa ccttggcgat tgatctttt        30

<210> SEQ ID NO 65
<211> LENGTH: 34
<212> TYPE: DNA
<213> ORGANISM: Artificial Sequence
<220> FEATURE:
<223> OTHER INFORMATION: Probe sequence for the 16S locus in Serratia
      spp.

<400> SEQUENCE: 65
tttattctgt gaacttaata cgttcatttt tatt        34

<210> SEQ ID NO 66
<211> LENGTH: 30
<212> TYPE: DNA
<213> ORGANISM: Artificial Sequence
<220> FEATURE:
<223> OTHER INFORMATION: Probe sequence for the 16S locus in Klebsiella
      oxytoca

<400> SEQUENCE: 66 tttttctaa ccttattcat tgatctttt        30

<210> SEQ ID NO 67
<211> LENGTH: 34
<212> TYPE: DNA
<213> ORGANISM: Artificial Sequence
<220> FEATURE:
<223> OTHER INFORMATION: Probe sequence for the 16S locus in
      Chromobacterium spp.

<400> SEQUENCE: 67
ttttattttc ccgctggtta ataccctta tttt        34

<210> SEQ ID NO 68
<211> LENGTH: 34
<212> TYPE: DNA
<213> ORGANISM: Artificial Sequence
<220> FEATURE:
<223> OTHER INFORMATION: Probe sequence for the 16S locus in Bacillus
      pumulis

<400> SEQUENCE: 68
tttatttaag tgcragagta actgctattt tatt        34

<210> SEQ ID NO 69
<211> LENGTH: 34
<212> TYPE: DNA
<213> ORGANISM: Artificial Sequence
<220> FEATURE:
<223> OTHER INFORMATION: Probe sequence for the 16S locus in
      Streptomyces spp.

<400> SEQUENCE: 69
ttttatttta agaagcgaga gtgactttta tttt        34

<210> SEQ ID NO 70
<211> LENGTH: 34
<212> TYPE: DNA
<213> ORGANISM: Artificial Sequence
<220> FEATURE:
<223> OTHER INFORMATION: Probe sequence for the 16S locus in Legionella
      spp.

<400> SEQUENCE: 70
tttattctga taggttaaga gctgatcttt attt                                 34

<210> SEQ ID NO 71
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with high sensitivity

<400> SEQUENCE: 71
tttttttttc ctacgggagg cagttttttt                                     30

<210> SEQ ID NO 72
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with medium sensitivity

<400> SEQUENCE: 72
ttttttttcc ctacgggagg cattttttt                                      30

<210> SEQ ID NO 73
<211> LENGTH: 30
<212> TYPE: DNA
<213> ORGANISM: Artificial Sequence
<220> FEATURE:
<223> OTHER INFORMATION: Probe sequence for the 16S locus for total
      aerobic bacteria with low sensitivity

<400> SEQUENCE: 73
tttattttcc ctacgggagg cttttatttt                                     30

<210> SEQ ID NO 74
<211> LENGTH: 38
<212> TYPE: DNA
<213> ORGANISM: Artificial Sequence
<220> FEATURE:
<223> OTHER INFORMATION: Probe sequence for the 16S locus in bile-
      tolerant gram negative bacteria with high sensitivity

<400> SEQUENCE: 74
cttttttcta tgcagtcatg ctgtgtgtrt gtcttttt                            38

<210> SEQ ID NO 75
<211> LENGTH: 33
<212> TYPE: DNA
<213> ORGANISM: Artificial Sequence
<220> FEATURE:
<223> OTHER INFORMATION: Probe sequence for the 16S locus in bile-
      tolerant gram negative bacteria with medium sensitivity

<400> SEQUENCE: 75
tttttctagc agccatgctg tgtgtrtttt ttt                                 33

<210> SEQ ID NO 76
<211> LENGTH: 34
<212> TYPE: DNA
<213> ORGANISM: Artificial Sequence
<220> FEATURE:
<223> OTHER INFORMATION: Probe sequence for the 16S locus in bile-
      tolerant gram negative bacteria with low sensitivity

<400> SEQUENCE: 76
tttttctatg cagtcatgct gcgtgtrttt tttt                              34

<210> SEQ ID NO 77
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with high sensitivity

<400> SEQUENCE: 77 tttttttctat tgacgttacc cgcttttttt                                  30

<210> SEQ ID NO 78
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with medium sensitivity

<400> SEQUENCE: 78 tttttttctat tgacgttacc cgttttttt                                   30

<210> SEQ ID NO 79
<211> LENGTH: 30
<212> TYPE: DNA
<213> ORGANISM: Artificial Sequence
<220> FEATURE:
<223> OTHER INFORMATION: Probe sequence for the 16S locus in
      Enterobacteriaceae with low sensitivity

<400> SEQUENCE: 79
tttattctat tgacgttacc catttatttt                                   30

<210> SEQ ID NO 80
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 80
tttttttgcc agccgacacc cattcttttt                                   30

<210> SEQ ID NO 81
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus fumigatus

<400> SEQUENCE: 81
tttcttttcg acacccaact ttatttcctt attt                              34

```
<210> SEQ ID NO 82
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus flavus

<400> SEQUENCE: 82 tttttcgca aatcaatctt tttccagtct tttt                          34

<210> SEQ ID NO 83
<211> LENGTH: 40
<212> TYPE: DNA
<213> ORGANISM: Artificial Sequence
<220> FEATURE:
<223> OTHER INFORMATION: Probe sequence for the ITS2 locus in
      Aspergillus flavus

<400> SEQUENCE: 83
tttttttctt gccgaacgca aatcaatctt tttttttttt                   40

<210> SEQ ID NO 84
<211> LENGTH: 34
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 84 tttttttcg acgttttcca accatttctt tttt                          34

<210> SEQ ID NO 85
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus niger

<400> SEQUENCE: 85
tttttttcgc cgacgttttc caatttttt                               30

<210> SEQ ID NO 86
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus terreus

<400> SEQUENCE: 86
tttttcgacg catttatttg caacccttt                               30

<210> SEQ ID NO 87
<211> LENGTH: 30
<212> TYPE: DNA
<213> ORGANISM: Artificial Sequence
<220> FEATURE:
<223> OTHER INFORMATION: Probe sequence for the ITS2 locus in
      Aspergillus nidulans

<400> SEQUENCE: 87 tttttggcg tctccaacct tacccttttt                               30

<210> SEQ ID NO 88
```

<210> SEQ ID NO 88
<211> LENGTH: 40
<212> TYPE: DNA
<213> ORGANISM: Artificial Sequence
<220> FEATURE:
<223> OTHER INFORMATION: Probe sequence for the ITS2 locus in Botrytis
      spp.

<400> SEQUENCE: 88
tttttttcat ctctcgttac aggttctcgg ttctttttttt                           40

<210> SEQ ID NO 89
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium spp.

<400> SEQUENCE: 89 tttttttcaac ccaaatttt atccaggcct tttt                                  34

<210> SEQ ID NO 90
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium paxilli

<400> SEQUENCE: 90 tttttttcccc tcaatcttta accaggcctt tttt                                 34

<210> SEQ ID NO 91
<211> LENGTH: 34
<212> TYPE: DNA
<213> ORGANISM: Artificial Sequence
<220> FEATURE:
<223> OTHER INFORMATION: Probe sequence for the ITS2 locus in
      Penicillium oxalicum

<400> SEQUENCE: 91 tttttttacac catcaatctt aaccaggcct tttt                                 34

<210> SEQ ID NO 92
<211> LENGTH: 34
<212> TYPE: DNA
<213> ORGANISM: Artificial Sequence
<220> FEATURE:
<223> OTHER INFORMATION: Probe sequence for the ITS2 locus in Fusarium
      solani

<400> SEQUENCE: 92
ttttttttaa cacctcgcra ctggagattt tttt                                  34

<210> SEQ ID NO 93
<211> LENGTH: 30
<212> TYPE: DNA
<213> ORGANISM: Artificial Sequence
<220> FEATURE:
<223> OTHER INFORMATION: Probe sequence for the ITS2 locus in Mucor spp.

<400> SEQUENCE: 93
ttttctccaw tgagyacgcc tgtttctttt                                       30

<210> SEQ ID NO 94
<211> LENGTH: 34
<212> TYPE: DNA

-continued

<213> ORGANISM: Artificial Sequence
<220> FEATURE:
<223> OTHER INFORMATION: Probe sequence for the ITS2 locus in Histoplasma capsulatum

<400> SEQUENCE: 94
tttatttttg tcgagttccg gtgccctttt attt 34

<210> SEQ ID NO 95
<211> LENGTH: 34
<212> TYPE: DNA
<213> ORGANISM: Artificial Sequence
<220> FEATURE:
<223> OTHER INFORMATION: Probe sequence for the ITS2 locus in Monocillium spp.

<400> SEQUENCE: 95
tttcttttga gcgacgacgg gcccaatttt cttt 34

<210> SEQ ID NO 96
<211> LENGTH: 34
<212> TYPE: DNA
<213> ORGANISM: Artificial Sequence
<220> FEATURE:
<223> OTHER INFORMATION: Probe sequence for the ITS2 locus in Trichoderma spp.

<400> SEQUENCE: 96
tttttcctcc tgcgcagtag tttgcacatc tttt 34

<210> SEQ ID NO 97
<211> LENGTH: 34
<212> TYPE: DNA
<213> ORGANISM: Artificial Sequence
<220> FEATURE:
<223> OTHER INFORMATION: Probe sequence for the ITS2 locus in Chaetomium spp.

<400> SEQUENCE: 97
tttcttttgg ttccggccgt taaaccattt tttt 34

<210> SEQ ID NO 98
<211> LENGTH: 34
<212> TYPE: DNA
<213> ORGANISM: Artificial Sequence
<220> FEATURE:
<223> OTHER INFORMATION: Probe sequence for the ITS2 locus in Stachybotrys spp.

<400> SEQUENCE: 98
tttcttctgc atcggagctc agcgcgtttt attt 34

<210> SEQ ID NO 99
<211> LENGTH: 34
<212> TYPE: DNA
<213> ORGANISM: Artificial Sequence
<220> FEATURE:
<223> OTHER INFORMATION: Probe sequence for the ITS2 locus in Alternaria spp.

<400> SEQUENCE: 99
ttttttcaaa ggtctagcat ccattaagtt tttt 34

<210> SEQ ID NO 100
<211> LENGTH: 34
<212> TYPE: DNA
<213> ORGANISM: Artificial Sequence

```
<220> FEATURE:
<223> OTHER INFORMATION: Probe sequence for the ITS2 locus in
      Phoma/Epicoccum ssp.

<400> SEQUENCE: 100
tttttttgca gtacatctcg cgctttgatt tttt                              34

<210> SEQ ID NO 101
<211> LENGTH: 33
<212> TYPE: DNA
<213> ORGANISM: Artificial Sequence
<220> FEATURE:
<223> OTHER INFORMATION: Probe sequence for the ITS2 locus in Erysiphe
      spp.

<400> SEQUENCE: 101 tttttttac gattctcgcg acagagtttt ttt                                33

<210> SEQ ID NO 102
<211> LENGTH: 34
<212> TYPE: DNA
<213> ORGANISM: Artificial Sequence
<220> FEATURE:
<223> OTHER INFORMATION: Probe sequence for the ITS2 locus in
      Podosphaera spp.

<400> SEQUENCE: 102 tttttttag tcaygtatct cgcgacagtt tttt                               34

<210> SEQ ID NO 103
<211> LENGTH: 34
<212> TYPE: DNA
<213> ORGANISM: Artificial Sequence
<220> FEATURE:
<223> OTHER INFORMATION: Probe sequence for the ITS2 locus in
      Podosphaera macularis

<400> SEQUENCE: 103 tttttttgacc tgccaaaacc cacataccat tttt                             34

<210> SEQ ID NO 104
<211> LENGTH: 34
<212> TYPE: DNA
<213> ORGANISM: Artificial Sequence
<220> FEATURE:
<223> OTHER INFORMATION: Probe sequence for the ITS2 locus in
      Oidiodendron spp.

<400> SEQUENCE: 104
tttttttgcg tagtacatct ctcgctcatt tttt                              34

<210> SEQ ID NO 105
<211> LENGTH: 34
<212> TYPE: DNA
<213> ORGANISM: Artificial Sequence
<220> FEATURE:
<223> OTHER INFORMATION: Probe sequence for the ITS2 locus in
      Rhodoturula spp.

<400> SEQUENCE: 105 tttttttctcg ttcgtaatgc attagcactt tttt                             34

<210> SEQ ID NO 106
<211> LENGTH: 34
<212> TYPE: DNA
<213> ORGANISM: Artificial Sequence
<220> FEATURE:
```

<223> OTHER INFORMATION: Probe sequence for the ITS2 locus in
Cladosporium spp.

<400> SEQUENCE: 106
ttttttttgt ggaaactatt cgctaaagtt tttt                          34

<210> SEQ ID NO 107
<211> LENGTH: 34
<212> TYPE: DNA
<213> ORGANISM: Artificial Sequence
<220> FEATURE:
<223> OTHER INFORMATION: Probe sequence for the ITS2 locus in Fusarum
oxysporum

<400> SEQUENCE: 107 ttttttctc gttactggta atcgtcgttt tttt                           34

<210> SEQ ID NO 108
<211> LENGTH: 34
<212> TYPE: DNA
<213> ORGANISM: Artificial Sequence
<220> FEATURE:
<223> OTHER INFORMATION: Probe sequence for the ITS2 locus in Candida
spp. Group 1

<400> SEQUENCE: 108 ttttttgtt tggtgttgag cratacgtat tttt                           34

<210> SEQ ID NO 109
<211> LENGTH: 35
<212> TYPE: DNA
<213> ORGANISM: Artificial Sequence
<220> FEATURE:
<223> OTHER INFORMATION: Probe sequence for the ITS2 locus in Candida
spp. Group 2

<400> SEQUENCE: 109
ttttactgtt tggtaatgag tgatactctc atttt                         35

<210> SEQ ID NO 110
<211> LENGTH: 34
<212> TYPE: DNA
<213> ORGANISM: Artificial Sequence
<220> FEATURE:
<223> OTHER INFORMATION: Probe sequence for the ITS2 locus in Candida
albicans

<400> SEQUENCE: 110 ttttttttg aaagacggta gtggtaagtt tttt                           34

<210> SEQ ID NO 111
<211> LENGTH: 34
<212> TYPE: DNA
<213> ORGANISM: Artificial Sequence
<220> FEATURE:
<223> OTHER INFORMATION: Probe sequence for the ITS2 locus in Isaria
spp.

<400> SEQUENCE: 111 tttattttc cgcggcgacc tctgctcttt attt                           34

<210> SEQ ID NO 112
<211> LENGTH: 34
<212> TYPE: DNA
<213> ORGANISM: Artificial Sequence
<220> FEATURE:
<223> OTHER INFORMATION: Probe sequence for the ITS2 locus in -continued Myrothecium spp.

<400> SEQUENCE: 112
tttattttcg gtggccatgc cgttaaattt tatt                                34

<210> SEQ ID NO 113
<211> LENGTH: 34
<212> TYPE: DNA
<213> ORGANISM: Artificial Sequence
<220> FEATURE:
<223> OTHER INFORMATION: Probe sequence for the ITS2 locus in Phythium
      oligandrum

<400> SEQUENCE: 113
ttttatttaa aggagacaac accaattttt attt                                34

<210> SEQ ID NO 114
<211> LENGTH: 38
<212> TYPE: DNA
<213> ORGANISM: Artificial Sequence
<220> FEATURE:
<223> OTHER INFORMATION: Probe sequence for the ITS2 locus in total
      yeast and mole with high sensitivity

<400> SEQUENCE: 114
ttttttttga atcatcgart ctttgaacgc attttttt                            38

<210> SEQ ID NO 115
<211> LENGTH: 36
<212> TYPE: DNA
<213> ORGANISM: Artificial Sequence
<220> FEATURE:
<223> OTHER INFORMATION: Probe sequence for the ITS2 locus in total
      yeast and mole with medium sensitivity

<400> SEQUENCE: 115
ttttttttga atcatcgart ctttgaacgt tttttt                              36

<210> SEQ ID NO 116
<211> LENGTH: 31
<212> TYPE: DNA
<213> ORGANISM: Artificial Sequence
<220> FEATURE:
<223> OTHER INFORMATION: Probe sequence for the ITS2 locus in total
      yeast and mole with low sensitivity

<400> SEQUENCE: 116
ttttttttga atcatcgart ctccttttt t                                    31

<210> SEQ ID NO 117
<211> LENGTH: 30
<212> TYPE: DNA
<213> ORGANISM: Artificial Sequence
<220> FEATURE:
<223> OTHER INFORMATION: Probe sequence for bacterial stx1 gene

<400> SEQUENCE: 117
tttttctttt ccaggtacaa cagcttttt                                      30

<210> SEQ ID NO 118
<211> LENGTH: 30
<212> TYPE: DNA
<213> ORGANISM: Artificial Sequence
<220> FEATURE:
<223> OTHER INFORMATION: Probe sequence for bacterial stx2 gene

<400> SEQUENCE: 118

```
tttttgcac tgtctgaaac tgcctttttt                                        30

<210> SEQ ID NO 119
<211> LENGTH: 34
<212> TYPE: DNA
<213> ORGANISM: Artificial Sequence
<220> FEATURE:
<223> OTHER INFORMATION: Probe sequence for bacterial InvA gene

<400> SEQUENCE: 119
tttttttatt gatgccgatt tgaaggcctt tttt                                  34

<210> SEQ ID NO 120
<211> LENGTH: 30
<212> TYPE: DNA
<213> ORGANISM: Artificial Sequence
<220> FEATURE:
<223> OTHER INFORMATION: Probe sequence for bacterial tuf gene

<400> SEQUENCE: 120 tttttgatg ccgatttgaa ggcctttttt                                        30

<210> SEQ ID NO 121
<211> LENGTH: 34
<212> TYPE: DNA
<213> ORGANISM: Artificial Sequence
<220> FEATURE:
<223> OTHER INFORMATION: Probe sequence for ITS1 locus in Cannabis
      species

<400> SEQUENCE: 121 tttttaatc tgcgccaagg aacaatattt tttt                                   34
```